United States Patent
Choi et al.

(10) Patent No.: US 7,598,279 B2
(45) Date of Patent: Oct. 6, 2009

(54) NEUROTHERAPEUTIC AZOLE COMPOUNDS

(75) Inventors: Yong Moon Choi, Pinebrook, NJ (US); Choon-Gil Kim, Daejon (KR); Han-Ju Yi, Daejeon (KR); Young-Sun Kang, Daejeon (KR); Hyun-Seok Lee, Daejeon (KR)

(73) Assignee: SK Holdings Co., Ltd., Seoul (KR)

( * ) Notice: Subject to any disclaimer, the term of this patent is extended or adjusted under 35 U.S.C. 154(b) by 558 days.

(21) Appl. No.: 11/407,526

(22) Filed: Apr. 20, 2006

(65) Prior Publication Data

US 2006/0258718 A1 Nov. 16, 2006

Related U.S. Application Data

(60) Provisional application No. 60/674,530, filed on Apr. 22, 2005.

(51) Int. Cl.
*A61K 31/445* (2006.01)
*C07D 401/12* (2006.01)
*C07D 249/08* (2006.01)
*C07D 249/04* (2006.01)

(52) U.S. Cl. .......... 514/359; 514/281; 514/283; 548/250; 548/255; 548/262.2

(58) Field of Classification Search .......... 514/259, 514/281, 283; 548/250, 255, 262, 2
See application file for complete search history.

(56) References Cited

U.S. PATENT DOCUMENTS

| 3,415,840 A | 12/1968 | Wolf |
| 5,100,916 A | 3/1992 | Johansson et al. |
| 6,770,659 B2 * | 8/2004 | Choi et al. .......... 514/326 |

FOREIGN PATENT DOCUMENTS

WO  WO 2006/112685  10/2006

OTHER PUBLICATIONS

International Search Report issued for the corresponding PCT application No. PCT/KR2006/001523.
Written Opinion of the International Search Report issued for the corresponding PCT application No. PCT/KR2006/001523.
Karakurt et al., "Synthesis of some 1-(2-naphthyl)-2-(imidazole-1-yl)ethanone oxime and oxime ether derivatives and their anticonvulsant and antimicrobial activities," Eur. J. Med. Chem. May 2001; 36(5): 421-433.

* cited by examiner

*Primary Examiner*—Golam M. M. Shameem
*Assistant Examiner*—Susannah Chung

(57) ABSTRACT

Azole compounds containing carbamoyl group and pharmaceutically useful salts thereof are described. The compounds are effective anticonvulsants which are used in the treatment of disorders of the central nervous system, especially as anxiety, depression, convulsion, epilepsy, migraine, bipolar disorder, drug abuse, smoking, ADHD, obesity, sleep disorder, neuropathic pain, stroke, cognitive impairment, neurodegeneration, stroke and muscle spasm.

60 Claims, No Drawings

NEUROTHERAPEUTIC AZOLE COMPOUNDS

CROSS-REFERENCE TO RELATED APPLICATION

This Application claims the benefit of Provisional Application Ser. No. 60/674,530, filed Apr. 22, 2005.

FIELD OF THE INVENTION

The present invention is directed to neurotherapeutic azole compounds containing a carbamoyl group which are useful as anticonvulsant agents.

DESCRIPTION OF THE PRIOR ART

Many reports have disclosed that arylalkyl azole compounds are effectively used as anticonvulsant, antimicrobial and hypoglycemic agents. One of the structurally distinct classes of antiepileptic drugs is the (arylalkyl) imidazoles.

J. Med. Chem., 24, 67 (1981) and J. Med. Chem., 24, 727 (1981) disclose Nafimidone (2-(1H-imidazole-1-yl)-1-(2-naphthalenyl)ethanone) and denzimol (α-(4-(2-phenylethyl)phenyl)-1H-imidazole-1-ethanol) are two independently discovered representatives of this group and protect mice and rats against maximal electroshock- or pentylenetetrazole-induced tonic seizures but do not antagonize clonic seizures induced by pentylenetetrazole, strychnine, bicuculline, or picrotoxin. These indicated that denzimol and nafimidone possess a profile of activity similar to that of phenytoin or carbamazepine but distinct from those of barbiturates or valproic acid. Moreover, both agents display acceptable therapeutic ratios and protective indices. Although formal accounts of carefully controlled clinical trials have not been reported, preliminary communications indicate these drugs are effective in epileptic patients. Structure-activity relationship studies show that anticonvulsant properties of this group are associated with the presence of a small oxygen functional group (such as carbonyl, ethylene dioxy, methoxy, acyloxy, and hydroxy substituents) in the alkylene bridge in addition to imidazole ring and lipophilic aryl portion facilitating penetration of the blood-brain barrier.

J. Med. Chem., 24, 67 (1981) discloses anticonvulsive 1-(naphthylalkyl)-1H-imidazole derivatives represented by the following general structural formula (I) and (II):

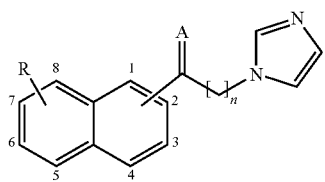

(I)

wherein, A is O, —OCH$_2$CH$_2$O—, —OCH$_2$CH$_2$CH$_2$O—, —OCH(CH$_3$)CH$_2$CH$_2$O—, —OCH$_2$C(CH$_3$)$_2$CH$_2$O—, (OCH$_3$)$_2$, —SCH$_2$CH$_2$S—, —SCH$_2$CH$_2$CH$_2$S—, (SCH$_3$)$_2$, (SC$_2$H$_5$)$_2$, (S-n-C$_3$H$_7$)$_2$, (S-i-C$_3$H$_7$)$_2$, (S-i-C$_4$H$_9$)$_2$, (SC$_6$H$_5$)$_2$, (SCH$_2$C$_6$H$_5$)$_2$, or (H)$_2$;

Alkyl chain is substituted at 1 or 2-position of the naphthalene ring;

R is H, 6-Cl, 6-Br, 6-CH$_3$, 6-C$_2$H$_5$, 6,7-(CH$_3$)$_2$, 6-OCH$_3$, 1-CH$_3$, 7-CH$_3$, 7-C$_3$H$_5$, 4-CH(CH$_3$)$_2$, or 6,7-(OCH$_3$)$_2$; and n is an integer from 0 to 2;

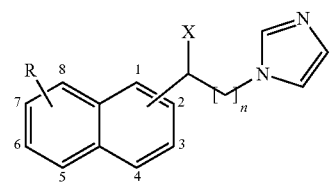

(II)

wherein, X is OH, OCH$_3$, OC$_3$H$_5$, O-n-C$_4$H$_9$, OC$_6$H$_5$, p-OC$_6$H$_4$Cl, o-OC$_6$H$_4$CH$_3$, OCOC$_2$H$_5$, OCOC$_6$H$_5$, SCH$_3$, SOCH$_3$, or SO$_2$CH$_3$;

Alkyl chain is substituted at 1 or 2-position of the naphthalene ring;

R is H, 6-Cl, 6-Br, 6-CH$_3$, 6-C$_2$H$_5$, 6,7-(CH$_3$)$_2$, 6-OCH$_3$, 1-CH$_3$, 7-CH$_3$, 7-C$_3$H$_5$, 4-CH(CH$_3$)$_2$, or 6,7-(OCH$_3$)$_2$; and n is an integer from 1 to 2.

J. Med. Chem., 24, 727 (1981) discloses anticonvulsant activity of N-(benzoylalkyl) imidazoles and N-(ω-phenyl-ω-hydroxyalkyl)imidazoles represented by the following general structural formula (III) and (IV):

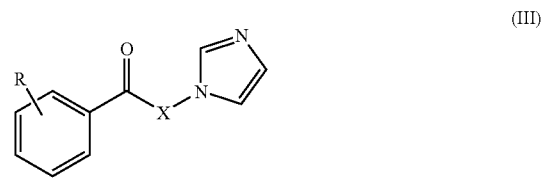

(III)

wherein, R is 3,4-(HO)$_2$, 4-HO, 4-NO$_2$, 4-NH$_2$, 4-CH$_3$CONH, 4-CH$_3$SO$_2$NH, 4-C$_6$H$_5$O, 4-(t-C$_4$H$_9$), 4-(s-C$_4$H$_9$), 4-(c-C$_6$H$_{11}$), 2-C$_6$H$_5$, 3-C$_6$H$_5$, or 4-C$_6$H$_5$CH$_2$CH$_2$; and X is CH$_2$, CHCH$_3$, CH$_3$CCH$_3$, CH$_2$CH$_2$, or CH(CH$_3$)CH$_2$;

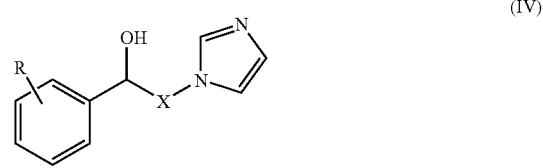

(IV)

wherein, R is 3,4-(HO)$_2$, 4-HO, 4-NO$_2$, 4-NH$_2$, 4-CH$_3$CONH, 4-CH$_3$SO$_2$NH, 4-C$_6$H$_5$O, 4-(t-C$_4$H$_9$), 4-(s-C$_4$H$_9$), 4-(c-C$_6$H$_{11}$), 2-C$_6$H$_5$, 3-C$_6$H$_5$, or 4-C$_6$H$_5$CH$_2$CH$_2$; and X is CH$_2$, CHCH$_3$, CH$_3$CCH$_3$, CH$_2$CH$_2$, or CH(CH$_3$)CH$_2$.

J. Med. Chem., 29, 1577 (1986) discloses structure-activity relationships of anticonvulsive (arylalkyl)imidazoles represented by the following general structural formula (V) and (VI):

(V)

wherein, Ar is benzo[b]thien-2-yl, benzo[b]thien-3-yl, benzofuran-2-yl, phenanthren-2-yl, 9,10-dihydrophenanthren-2-yl, 9,10-dihydrophenanthren-3-yl, naphthalen-2-yl, or naphthalene-3-yl; and X is O or (H, OH);

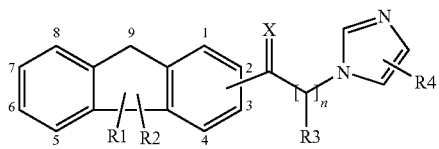

(VI)

wherein, X is O, (H, OH), (H, OCOPh), (CH$_3$, OH), —SCH$_2$CH$_2$S—, —OCH$_2$CH$_2$O—, —OCH$_2$CH$_2$CH$_2$O—, —OCH(CH$_3$)CH$_2$O—, —OCH$_2$C(CH$_3$)$_2$CH$_2$O—, or (H, H);

Alkyl chain is substituted at 1, 2, or 4-position of the fluorenyl ring;

R$_1$ is H, 9-CH$_3$, 7-CH$_3$, 7-C$_2$H$_5$ or 7-OCH$_3$, 7-(CH$_3$)$_2$CH, or 7-Br;

R$_2$ is H or 9-CH$_3$;

R$_3$ is H, α-CH$_3$, or α-C$_2$H$_5$;

R$_4$ is H, 2-CH$_3$, 2-C$_2$H$_5$, 4-CH$_3$, or 4-C$_6$H$_5$; and n is an integer from 1 to 3.

This series of imidazole anticonvulsants was highly selective; while many compounds displayed potent anti-electroshock activity, little or no activity was observed against pentylenetetrazole-induced clonic seizures or in the horizontal screen test for ataxia. All active compounds that we tested in this series, as well as denzimol and nafimidone, potentiated hexobarbital-induced sleeping time in mice, probably by imidazole-mediated inhibition of cytochrome P-450.

Eur. J. Med. Chem., 28, 749 (1993) discloses anticonvulsant activity of 1-(4-methylphenyl)-2-(1H-imidazol-1-yl) ethanol.

Eur. J. Med. Chem., 36, 421 (2001) discloses some 1-(2-naphtyl)-2-(imidazole-1-yl)ethanone oxime and oxime ether derivatives of the following general structural formula (VII) and pharmaceutical acceptable salts thereof possessing both anticonvulsant and antimicrobial activities:

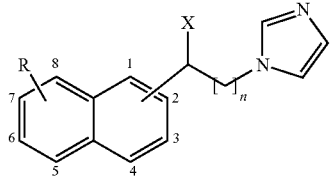

(VII)

wherein, R is selected from the group consisting of hydrogen, methyl, ethyl, propyl, allyl, cyclohexyl, benzyl, 4-chlorobenzyl, and 2,4-dichlorobenzyl.

U.S. Pat. No. 3,415,840 discloses pyrazole-1-ethanol derivatives of the following general structural formula (VIII) possessing useful pharmacological effects as hypoglycemic agents and anticonvulsant agents:

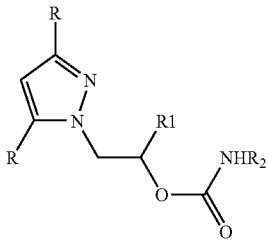

(VIII)

wherein, R stands for a member of the group consisting of hydrogen and methyl, R1 stands for a member of the group consisting of phenyl and phenoxymethyl while R2 represents a member of the group consisting of hydrogen and phenyl; and the non-toxic acid addition salts thereof.

Active research and development efforts have been and continues to be directed to the application of azole compounds containing carbamoyl group for the treatment of CNS disorders such as anxiety, depression, convulsion, epilepsy, migraine, bipolar disorder, drug abuse, smoking, ADHD, obesity, sleep disorder, neuropathic pain, cognitive impairment, stroke, neurodegeneration and muscle spasm.

SUMMARY OF THE INVENTION

This invention is directed to azole compounds containing carbamoyl group having formula (IX) and their pharmaceutically acceptable salts:

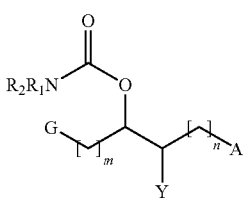

(IX)

wherein, G is a ring selected from the group consisting of piperonyl, indanyl, naphtyl, phenyl and phenoxy methyl which ring may be substituted with one or more identical or different substituents selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, perfluoroalkyl, phenoxy, phenylalkyloxy of 1 to 8 carbon atoms or phenoxyalkyl of 1 to 8 carbon atoms, wherein the phenyl moiety of phenoxy, phenoxyalkyl and phenylalkyloxy is unsubstituted or substituted with amino, mono- or di-substituted amino with lower alkyl of 1 to 8 carbon atoms, amido, sulfonamido, nitro, carboxyl, or perfluoroalkyl of 1 to 8 carbon atoms;

m is an integer from 0 to 6;

Y is selected from the group consisting of hydrogen, halogen, and lower alkyl of 1 to 8 carbon atoms;

n is an integer from 0 to 6;

A is azole group represented by the following structural formula (X-1) or (X-2):

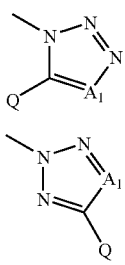

(X-1)

(X-2)

wherein, A1 is selected from the group consisting of nitrogen atom and CH;

Q is selected from the group consisting of hydrogen, perfluoroalkyl, halogen, amino, mono- or di-substituted alkyl amino with alkyl of 1 to 8 carbon atoms, amido, linear or branched alkyl of 1 to 8 carbon atoms, cycloalkyl of 3 to 8 carbon atoms, arylalkyl, morpholino, piperidino, pyrrolidino, thioalkoxy of 1 to 8 carbon atoms, benzylthio, thienyl, aminoalkyl, hydroxyalkyl, styryl, carboxylic, pyridyl, unsubstituted phenyl and phenyl substituted with one or more identical or different substituents selected from the group consisting of hydrogen, lower alkyl of 1 to 8 carbon atoms, arylalkyl, halogen, alkoxy containing 1 to 8 carbon atoms, phenoxy, amino, mono- or di-substituted amino with alkyl of 1 to 8 carbon atoms, nitro, hydroxy, thioalkoxy, furanyl, sulfonamido, and perfluoroalkyl;

$R_1$ and $R_2$ are independently selected from the group consisting of hydrogen, C(=O)NH$_2$, lower alkyl of 1 to 8 carbon atoms, non-substituted or substituted phenyl, and non-substituted or substituted phenylalkyl of 1 to 8 carbon atoms, or taken together with attached nitrogen form a imidazole, piperazine or phenyl piperazine ring or cyclic amine ring represented by the following structural formula (XI):

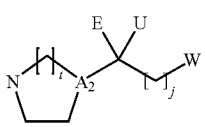

(XI)

wherein, $A_2$ is selected from the group consisting of nitrogen atom and carbon atom;

E and U may and are independently selected from the group consisting of hydrogen, hydroxy and O-carbamoyl or taken together form oxo;

W is selected from a ring consisting of piperonyl, indanyl, naphtyl, tetrazolyl, triazolyl, pyridyl and phenyl which ring may be substituted with one or more identical or different substituents selected from the group consisting of hydrogen, lower alkyl of 1 to 8 carbon atoms, halogen, alkoxy containing 1 to 8 carbon atoms, thioalkoxy containing 1 to 8 carbon atoms, phenoxy, phenylalkyloxy of 1 to 8 carbon atoms, phenoxyalkyl of 1 to 8 carbon atoms, where the phenyl moiety of phenoxy, phenylalkyloxy and phenoxyalkyl is unsubstituted or substituted with amino, mono- or di-substituted amino with alkyl of 1 to 8 carbon atoms, amido, sulfonamido, nitro, carboxyl, hydroxy, or perfluoroalkyl of 1 to 8 carbon atoms;

j is an integer from 0 to 4; and t is an integer from 0 to 4, preferably from 0 to 2.

In one embodiment, the compound containing carbamoyl group has the following structural formula (XVII):

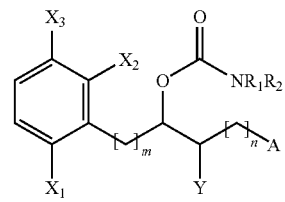

(XVII)

wherein, $X_1$ is selected from the group consisting of lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, or phenoxyalkyl of 1 to 8 carbon atoms wherein the phenyl moiety of phenoxy, phenylalkyloxy and phenoxyalkyl is unsubstituted or substituted with amino, mono- or di-substituted amino with lower alkyl of 1 to 8 carbon atoms, amido, sulfonamido, nitro, carboxyl, or perfluoroalkyl of 1 to 8 carbon atoms;

$X_2$ and $X_3$ may be the same with or different from each other and are independently selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, phenoxyalkyl of 1 to 8 carbon atoms wherein the phenyl moiety of phenoxy, phenylalkyloxy and phenoxyalkyl is unsubstituted or substituted with amino, mono- or di-substituted amino with lower alkyl of 1 to 8 carbon atoms, amido, sulfonamido, nitro, carboxyl, or perfluoroalkyl of 1 to 8 carbon atoms;

m is an integer from 0 to 6;

Y is selected from the group consisting of hydrogen and lower alkyl of 1 to 8 carbon atoms;

n is an integer from 0 to 6;

A is azole group represented by the following structural formula (X-1) or (X-2):

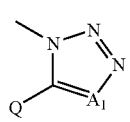

(X-1)

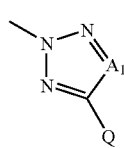

(X-2)

wherein, $A_1$ is selected from the group consisting of nitrogen atom and CH;

Q is as above; and $R_1$ and $R_2$ are as above.

In another embodiment, azole compound containing carbamoyl group has the following formula (XVIII):

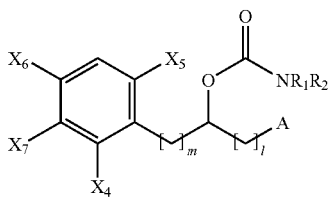

(XVIII)

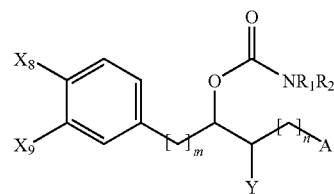

(XIX)

wherein, $X_4$ and $X_6$ are independently selected from the group consisting of lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, phenoxyalkyl of 1 to 8 carbon atoms wherein the phenyl moiety of phenoxy, phenylalkyloxy and phenoxyalkyl is unsubstituted or substituted with amino, mono- or di-substituted amino with alkyl of 1 to 8 carbon atoms, amido, sulfonamido, nitro, carboxyl, or perfluoroalkyl of 1 to 8 carbon atoms;

$X_5$ and $X_7$ may be the same with or different from each other and are independently selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, phenoxyalkyl of 1 to 8 carbon atoms wherein the phenyl moiety of phenoxy, phenylalkyloxy and phenoxyalkyl is unsubstituted or substituted with, amino, mono- or di-substituted amino with alkyl of 1 to 8 carbon atoms, amido, sulfonamido, nitro, carboxyl, or perfluoroalkyl of 1 to 8 carbon atoms;

m is an integer from 0 to 6;

l is an integer from 1 to 6;

A is azole group represented by the following structural formula (X-1) or (X-2):

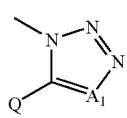

(X-1)

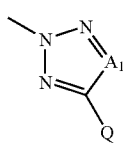

(X-2)

wherein, $A_1$ is selected from the group consisting of nitrogen atom and CH; and Q, $R_1$ and $R_2$ are as above.

In another embodiment, the azole compound containing carbamoyl group has the following structural formula (XIX):

wherein, $X_8$ and $X_9$ are independently selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms or phenoxyalkyl of 1 to 8 carbon atoms wherein the phenyl moiety of phenoxy, phenylalkyloxy and phenoxyalkyl is unsubstituted or substituted with, amino, mono- or di-substituted amino with alkyl of 1 to 8 carbon atoms, amido, sulfonamido, nitro, carboxyl, or perfluoroalkyl of 1 to 8 carbon atoms;

m is an integer from 0 to 6;

Y is selected from the group consisting of hydrogen and lower alkyl of 1 to 8 carbon atoms;

n is an integer from 0 to 6; and

A, $R_1$ and $R_2$ are as above.

In another embodiment, the azole compound containing carbamoyl group has the following structural formula (XX):

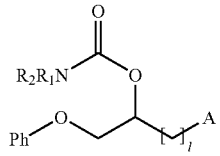

(XX)

wherein, Ph is phenyl, piperonyl, indanyl or naphtyl which may be substituted with one or more identical or different substituents selected from the group consisting of hydrogen, lower alkyl of 1 to 8 carbon atoms, halogen, alkoxy containing 1 to 8 carbon atoms, thioalkoxy containing 1 to 8 carbon atoms, phenoxy, phenylalkyloxy of 1 to 8 carbon atoms, phenoxyalkyl of 1 to 8 carbon atoms, wherein the phenyl moiety of phenoxy, phenylalkyloxy and phenoxyalkyl is unsubstituted or substituted with amino, mono- or di-substituted amino with alkyl of 1 to 8 carbon atoms, amido, sulfonamido, nitro, carboxyl, hydroxy, or perfluoroalkyl of 1 to 8 carbon atoms;

l is an integer from 1 to 6; and

A, $R_1$ and $R_2$ are as above.

In another embodiment compound containing carbamoyl group is structural formula (XXI):

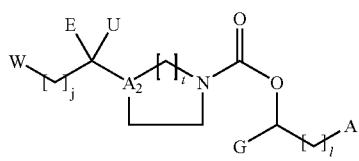

(XXI)

wherein, E, U, W, $A_2$, A, G, j and t are as above and l is an integer from 1 to 4;

and pharmaceutically useful salts thereof.

The compounds of this invention includes all optical and stereo isomeric including mixture racemates as well as substantially pure enantiomers such as the R and S enantiomers. With respect to pure enantiomers, preferably the optical purity of these enantiomers of the containing carbamoyl group represented by the following general structural formula (IX) and their pharmaceutically acceptable salts is greater than $60\%_{ee}$, more preferably greater than $95\%_{ee}$, and most preferably greater than $98\%_{ee}$. The term "ee" means enantiomeric excess. For instance, one enantiomer of a specific compound is present in a mixture of the enantiomers for that compound at a greater amount relative to the other enantiomer. An enantiomerically enriched form may include a mixture of enantiomers of a specific compound in which the concentration of a single enantiomer of that compound is greater than 50%, more typically greater than 60%, 70%, 80%, or 90%, or higher (e.g., >95%, >97%, >99%, >99.5%), relative to the other enantiomer of that compound.

These compounds represented by the formula (IX) are active as anticonvulsive agents. Such agents are utilized in the treatment of central nervous system diseases, particularly, as anxiety, depression, convulsion, epilepsy, migraine, bipolar disorder, drug abuse, smoking, ADHD, obesity, sleep disorder, neuropathic pain, cognitive impairment, stroke, neurodegeneration and centrally acting muscle spasm.

DETAILED DESCRIPTION OF THE INVENTION

In accordance with the present invention, the compound represented by the general formula (IX) and their pharmaceutically acceptable salts thereof can be prepared by the following steps starting from the racemic or enantiomerically enriched alcohol compounds represented by the following general structural formula (XII):

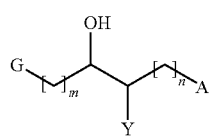

(XII)

wherein, G, m, Y, n and A are as above.

The two methods for preparing the alcohol compounds represented by the general structural formula (XII) will be described below in detail.

Method I

Reacting an epoxide of by the following general structural formula (XIII);

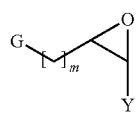

(XIII)

wherein, G, m and Y are as above with azole of the formula (XIV);

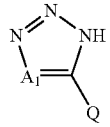

(XIV)

wherein, $A_1$ and Q are as above to synthesize the racemic or enantiomerically enriched alcohol compounds represented by the general structural formula (XII):

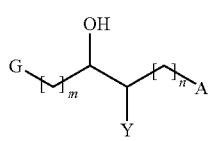

(XII)

wherein, G, Y, A, m and n are as above.

It should be noted that the stereochemistry of the product represented by the general formula (IX) depends on that of the starting material represented by the general structural formula (XIII) and intermediates represented by the general structural formula (XII); a starting material represented by the general structural formula (XIII) with an (R)-configuration yields only a alcohol compound represented by the general structural formula (XII) with (R)-configuration and a starting material represented by the general structural formula (XIII) with an (S)-configuration yields only a intermediate represented by the general structural formula (XII) with (S)-configuration. In the preparation of azole compounds containing carbamoyl group represented by the general structural formula (IX) (Reaction Scheme 1 and 2), alcohol intermediates represented by the general structural formula (XII) with an (R)-configuration yields only a product represented by the general structural formula (IX) with (R)-configuration and alcohol intermediates represented by the general structural formula (XII) with an (S)-configuration yields only a product represented by the general structural formula (IX) with (S)-configuration.

Details of the reaction conditions described in Method I are as follows. To a solution of azole derivative of the general structural formula (XIV) (0.5~10 equiv) and base such as sodium hydride, sodium methoxide, sodium ethoxide, sodium carbonate, potassium carbonate, calcium carbonate, lithium carbonate (0~100 equiv), pyridine, diethyl amine, diisopropylethyl amine, and triethylamine in organic solvent such as methyl alcohol, ethyl alcohol, isopropyl alcohol, DMSO, acetonitrile, DMF, NMP, acetone, methylene chloride, chloroform, MIBK, DME, ethyl acetate, THF, 1,4-dioxane, benzene, toluene, xylene, hexane, heptane and cyclohexane (0~10000 eq), racemic or enantiomerically enriched epoxide derivative of the general structural formula (XIII) was slowly added. The reaction was warmed to 40~189° C. for 0.1~240 hours and then cooled to 25° C. Organic solvent such as ethyl acetate, diethyl ether, benzene, toluene, xylene, methylene chloride, chloroform, heptane, cyclohexane and hexane was added to this mixture and organic layer was washed with brine. The resulting organic layer was dried and concentrated in vacuo. This residue was consisting of two regio-isomers, one is azol-1yl compound (hereinafter referred to as "1N-azole") and another is azol-2-yl compound (hereinafter referred to as "2N-azole"). They were separated by column chromatography, eluting with an increasing ratio of ethyl acetate in hexane.

Method II

Reacting Alkyl halide represented by the following general structural formula (XV);

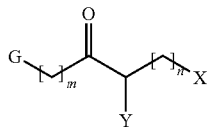

(XV)

wherein, G, Y and m are as above;
n is an integer from 0 to 6; and
X is halogen such as Cl, Br and I;

with azole represented by the general structural formula (XIV) and then treat with sodium borohydride to synthesize alcohol compounds represented by the general structural formula (XII).

Details of the reaction conditions described in Method II are as follows. To a solution of azole derivative of the general structural formula (XIV) (0.5~10 equiv) and base such as sodium hydride, sodium methoxide sodium ethoxide, sodium carbonate, potassium carbonate, calcium carbonate, lithium carbonate (0~100 equiv), pyridine, diethyl amine, diisopropylethyl amine, and triethylamine in organic solvent such as methyl alcohol, ethyl alcohol, isopropyl alcohol, DMSO, acetonitrile, DMF, NMP, acetone, methylene chloride, chloroform, MIBK, DME, ethyl acetate, THF, 1,4-dioxane, benzene, toluene, xylene, hexane, heptane and cyclohexane (0~10000 equiv), alkyl halide derivative of the general structural formula (XV) was slowly added. The reaction was warmed to 40~189° C. for 0.1~240 hours and then cooled to 25° C. Organic solvent such as ethyl acetate, diethyl ether, benzene, toluene, xylene, methylene chloride, chloroform, heptane, cyclohexane and hexane was added to this mixture and organic layer was washed with brine. The crude product was dissolved in methyl alcohol (1~10000 equiv) and then sodium borohydride (1~100 equiv) was added to this solution slowly. After 0.1~24 hours stirring at room temperature, the reaction mixture was concentrated in vacuo. Organic solvent such as ethyl acetate, diethyl ether, benzene, toluene, xylene, methylene chloride, chloroform, heptane, cyclohexane and hexane was added to this mixture and organic layer was washed with brine. The resulting organic layer was dried and concentrated in vacuo. This residue was consisting of 1N-azole and 2N-azole. They were separated by column chromatography, eluting with an increasing ratio of ethyl acetate in hexane.

There are several pathways to introduce carbamoyl group to alcohol compounds such as 1,1'-carbonyldiimidazole-amine, sodium cyanate-acid, carbamoyl chloride, chlorosulfamoyl isocyanate-water, disuccimidyl carbonate-amine, phosgene-amine, triphosgene-amine, chloroformate-amine, trichloroacetylchloride-amine, trichloroactylisocyanate, trimethylsilylisocyanate, 1-chlorocarbonylbenzotriazole-amine and so on. Some of pathways to prepare azole compounds containing carbamoyl group represented by the general structural formula (IX) are summarized as set forth in Reaction Scheme 1 and Reaction Scheme 2 below.

Reaction Scheme 1

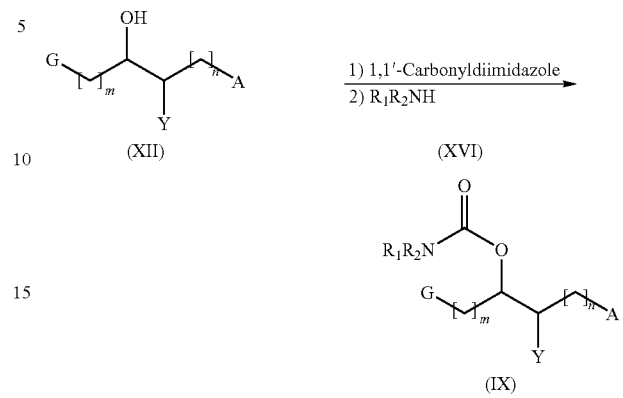

wherein, G, Y, A, $R_1$, $R_2$, m and n are as above.

The azole compounds containing carbamoyl group represented by the general structural formula (IX) were prepared by reacting alcohol compounds represented by the general structural formula (XII) with 1,1'-carbonyldiimidazole and then with amine base represented by the general structural formula (XVI);

$R_1R_2NH$ (XVI)

wherein,
$R_1$ and $R_2$ are as above.

Details of the reaction conditions described in Reaction Scheme I are as follows. For the conversion of the racemic or enantiomerically enriched alcohol compounds of the general structural formula (XII) to the racemic or enantiomerically enriched azole compounds containing carbamoyl group of the general structural formula (IX), the concentration of the alcohol compounds of the general structural formula (XII) is about 0.005 to 0.1 moles with 1,1'-carbonyldiimidazole ranging from about 1.0 to 3.5 equivalents. This reaction is preferably carried out at a temperature of −1.0 to 66° C. Without purification, the resulting intermediate is treated with 1 to 1,000 equivalents of amine base represented by the general structural formula (XVI) at a temperature of −10 to 30° C. to give the compound represented by the general structural formula (IX). For this carbamoylation, an ethereal solvent such as diethyl ether and tetrahydrofuran, a halogenated hydrocarbon solvent such as dichloromethane and chloroform, or the mixture thereof may be used.

Reaction Scheme 2

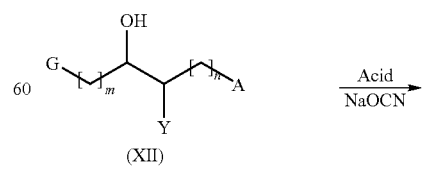

-continued

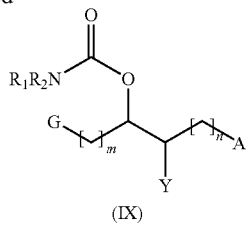

(IX)

wherein, G, Y, A, R$_1$, R$_2$, m and n are as above.

Details of the reaction conditions described in Reaction Scheme 2 are as follows. For the conversion of the racemic or enantiomerically enriched alcohol compounds represented by the general structural formula (XII) to the racemic or enantiomerically enriched azole compounds containing carbamoyl group represented by the general structural formula (IX), the concentration of alcohol compounds represented by the general structural formula (XII) is about 0.005 to 0.1 moles with sodium cyanate ranging from about 0.5 to 4.0 equivalents and acid ranging from about 0.5 to 4.0 equivalents. This reaction is preferably carried out at a temperature of −10 to 66° C. to give the compound represented by the general structural formula (IX). For this carbamoylation, an ethereal solvent such as diethyl ether and tetrahydrofuran, a halogenated hydrocarbon solvent such as dichloromethane and chloroform, or the mixture thereof may be used.

Among the preferred embodiments of the compounds of formula IX are included compounds of the formula:

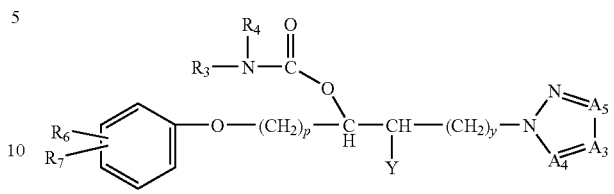

IX-A wherein, Y is as above;

A$_3$, A$_4$ and A$_5$ are independently selected from the group consisting of CH or N, with at least one of A$_3$, A$_4$ and A$_5$ being CH; and at least one of the other of A$_3$, A$_4$ and A$_5$ being N;

R$_6$ and R$_7$ are selected from the group consisting of hydrogen, halogen, perfluoroalkyl, alkyl of from 1 to 8 carbon atoms, thioalkoxy, and alkoxy;

R$_3$ and R$_4$ are alkyl, hydrogen,

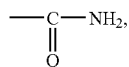

or taken together with the attached nitrogen atom form an imidazole, or phenyl piperazine ring; and y is an integer of from 0 to 4, preferably from 0 to 2 or pharmaceutically acceptable salts thereof;

a compound of the formula:

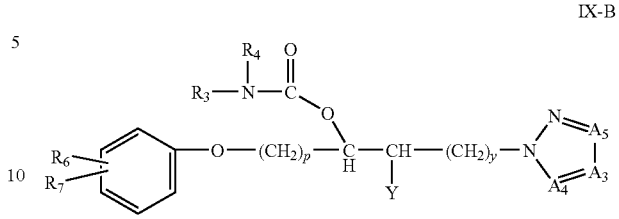

IX-B wherein R$_3$, R$_4$, R$_6$, R$_7$, Y, y, A$_3$, A$_4$ and A$_5$ are as above; and p is an integer of from 0 to 1;

or pharmaceutically acceptable salts thereof; and a compound of the formula:

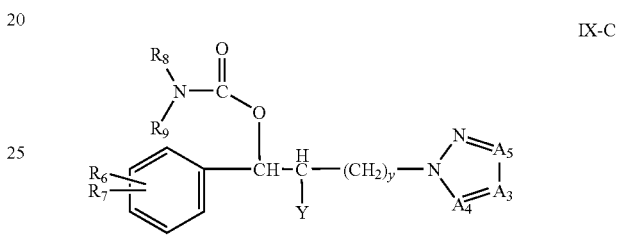

IX-C wherein R$_8$ and R$_9$ taken together with the attached nitrogen atom form a substituent of the formula:

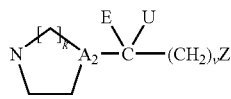

wherein E, U, A$_2$, A$_3$, A$_4$ and A$_5$ are as above;
k and v are an integer from 0 to 1;
Z is a phenyl, phenoxy, alkyl or phenylalkyloxy substitued where the phenyl moiety of said substitutent is unsubstituted or substituted with from one to three substituents selected from the group consisting of halogen, alkyl, perfluoroalkyl or alkoxy;
Y is a hydrogen, halogen or alkyl;
y is an integer of from 0 to 1;
R$_6$ and R$_7$ are selected from the group consisting of hydrogen, halogen, perfluoroalkyl, thioalkoxy, alkoxy and alkyl.

Another group of preferred compounds having the activity of the compound of formula IX are:

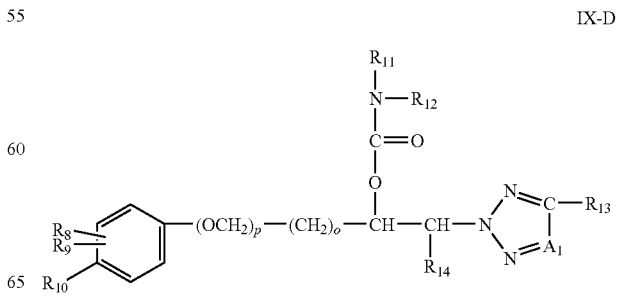

IX-D wherein $A_1$ is as above; $R_8$ and $R_9$ are hydrogen, halogen, lower alkoxy, lower alkyl, hydroxy, trifluromethyl, amino, mono or dilower alkyl amino, nitro or $R_8$ and $R_9$ when substituted on adjacent carbon atoms and when $R_{10}$ is hydrogen can be taken together to form a cyclolower alkyl, phenyl or heterocyclolower alkyl ring; $R_{10}$ is lower alkoxy, phenyloxy, phenylalkoxy, hydrogen, cycloloweralkyl, halogen, hydroxy, lower alkyl, nitro, trifluoromethyl, mono or lower dikalkyl amino or amino; $R_{11}$ is hydrogen, lower alkyl, phenyl or phenyl lower alkyl wherein the phenyl group can be unsubstituted or mono or disubstituted with a lower alkyl, hydroxy, lower alkoxy, or halo; $R_{12}$ is hydrogen or lower alkyl or $R_{12}$ taken together with $R_{11}$ and their attached nitrogen atom form a 4 to 6 membered heteroarmatic ring containing at most 3 additional hetero nitrogen atoms; $R_{14}$ is hydrogen, amino carbonyl, or lower alkyl: $R_{13}$ is hydrogen, lower alkyl, amino, mono or dilower alkylamino hetero aromatic, amino carbonyl or phenyl where the phenyl group can be unsubstituted or mono or disubstituted with a lower alkyl, hydroxy, lower alkoxy, or halo; and o and p are integers from 0-1.

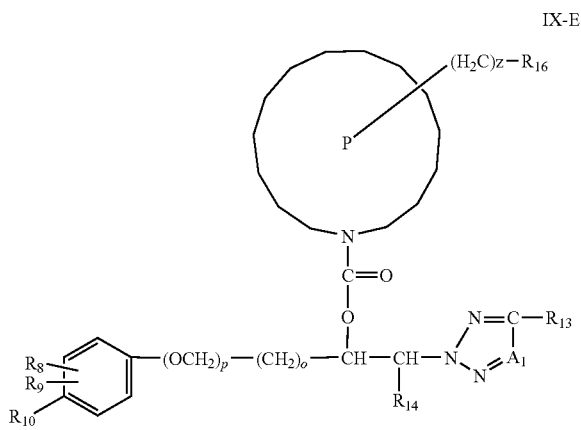

wherein

is a 4 to 6 membered a heterocycloalkyl ring containing at most 1 additional hetero nitrogen atom; $A_1$ is as above; $R_8$, $R_9$, $R_{10}$, $R_{13}$ and $R_{14}$ are as above o, z and p are integers from 0-1; $R_{16}$ is phenyl, phenyl carbonyl, a five or six membered hetero aromatic ring containing from 1 to 4 nitro heteroatoms, wherein said phenyl and heteroaromatic rings can be unsubstituted or mono or di-substituted with hydroxy, hydroxy lower alkyl, lower alkoxy, halogen, phenyl or trifloromethyl.

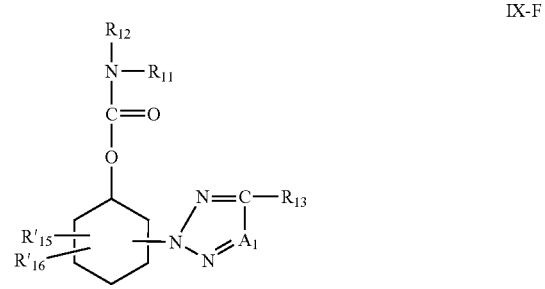

wherein $A_1$, is as above; $R_{11}$, $R_{12}$ and $R_{13}$ are as above; and $R'_{15}$ and $R'_{16}$ when taken together with their attached carbon atoms form a cycloalkyl or phenyl ring which can be unsubstituted or substituted with halo, lower alkyl, lower alkoxy, hydroxy, halogen or trifluoromethyl.

The compounds of IX-A, IX-B, IX-C, IX-D, IX-E and IX-F constitute preferred embodiments of the compound of formula IX. Particularly preferred embodiments of the compounds of formula IX-A, IX-B, IX-C, IX-D, IX-E and IX-F are those compounds where the nitrogen containing ring is a tetrazole or triazole ring. The triazoles are those compounds where one of $A_1$, $A_3$, $A_4$ and $A_5$ is nitrogen and the others are CH. The tetrazoles of the compounds of formula IX-A, IX-B, IX-C, IX-D, IX-E and IX-F are those compounds where two of $A_1$, $A_3$, $A_4$ and $A_5$ are nitrogen and the other is CH. Generally, among the triazoles and tetrazoles of the compounds of formula IX-A, IX-B and IX-C are those compounds where $R_6$ and $R_7$ are selected from the group consisting of hydrogen, halogen, perfluoroalkyl, alkyl and alkoxy. Where $R_1$ and $R_2$ in the compound of formula IX, are substituted phenyl or substituted phenylalkyl, the phenyl moiety can be substituted in one or more positions, preferably from one to three positions with amino, mono- or di-substituted alkyl amino, amido, alkyl, alkoxy and nitro.

The compounds of formula IX, IX-A, IX-B, IX-C, IX-D, IX-E and IX-F include all forms of these compounds including these stereo, geometric and optical isomeric forms. The compounds of formula IX, IX-A, IX-B, IX-C, IX-D, IX-E and IX-F can exist as a racemate, as well as any mixture of these stereo, geometric or optical isomeric forms. In accordance with a preferred embodiment of this invention, the compounds of IX, IX-A, IX-B, IX-C, IX-D, IX-E and IX-F exist in pure isomeric form substantially free of these other isomeric forms. By substantially free, it is meant, that the specific isomer exists in its pure isomeric form such as a pure enantiomer with at least 95% by weight with at most 5% by weight of the other isomeric forms such as its other enantiomer.

As used in the specification, the term "alkyl", alone or in combination, means a monovalent straight or branched-chain saturated hydrocarbon alkyl group containing from one to eight carbon atoms, preferably lower alkyl containing from one to six carbon atoms, such as methyl, ethyl, n-propyl, isopropyl, n-butyl, sec-butyl, isobutyl, tert-butyl, n-pentyl, n-hexyl and the like.

The term "alkoxy" means a straight or branched-chain alkoxy group formed from alkyl containing from one to eight carbon atoms, preferably from one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring such as phenyl or naphthyl, with phenyl being preferred.

The term "perfluoro-lower alkyl" means any lower alkyl group wherein all the hydrogens of the lower alkyl group are substituted or replaced by fluorine. Among the prefered perfluoro-lower alkyl groups are trifluoromethyl, pentafluroethyl, heptafluoropropyl, etc with trifluromethyl being especially preferred.

The term "cycloalkyl" means a cyclolower alkyl substituent which designates a monovalent unsubstituted 3- to 6-membered saturated carbocylic hydrocarbon ring. Among the preferred cycloalkyl substituents are cyclopropyl, cyclobutyl, cyclohexyl, etc.

The term "heterocycloalkyl" refers to a 4 to 6 membered monocyclic saturated ring containing 3 to 4 carbon atoms and one to three hetero nitrogen or oxygen atoms.

The term "heteroaromatic ring" refers to a monovalent 4 to 6 membered monocyclic heteroaromatic ring containing from 4 to 5 carbon atoms and from 1 to 4 hetero nitrogen.

The term "pharmaceutically acceptable salts" refers to conventional acid-addition salts or base-addition salts that retain the biological effectiveness and properties of the compounds of formulae IX, IX-A, IX-B, IX-C, IX-D, IX-E and IX-F are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

Representative examples of the racemic or enantiomerically enriched azole compounds containing carbamoyl group represented by the general structural formula (IX) are selected from the group consisting of

Compound Name
1 Carbamic acid 1-(2-chloro-phenyl)-2-[1,2,3]triazol-2-yl-ethyl ester
2 Carbamic acid 1-(2-chloro-phenyl)-2-tetrazol-2-yl-ethyl ester
3 Carbamic acid 1-(4-methoxy-phenyl)-2-tetrazol-2-yl-ethyl ester
4 Carbamic acid 1-phenyl-2-tetrazol-2-yl-ethyl ester
5 Carbamic acid 1-(4-chloro-phenyl)-2-tetrazol-2-yl-ethyl ester
6 Carbamic acid 1-(4-methoxy-phenyl)-2-[1,2,3]triazol-2-yl-ethyl ester
7 Carbamic acid 1-phenyl-2-[1,2,3]triazol-2-yl-ethyl ester
8 Carbamic acid 1-p-tolyl-2-[1,2,3]triazol-2-yl-ethyl ester
9 Carbamic acid 1-(3-chloro-phenyl)-2-[1,2,3]triazol-2-yl-ethyl ester
10 Carbamic acid 1-(4-chloro-phenyl)-2-[1,2,3]triazol-2-yl-ethyl ester
11 Carbamic acid 2-tetrazol-2-yl-1-p-tolyl-ethyl ester
12 Carbamic acid 1-o-tolyl-2-[1,2,3]triazol-2-yl-ethyl ester
13 Carbamic acid 1-(4-nitro-phenyl)-2-[1,2,3]triazol-2-yl-ethyl ester
14 Carbamic acid 1-(4-nitro-phenyl)-2-tetrazol-2-yl-ethyl ester
15 Carbamic acid 1-(4-fluoro-phenyl)-2-tetrazol-2-yl-ethyl ester
16 Carbamic acid 1-(4-fluoro-phenyl)-2-[1,2,3]triazol-2-yl-ethyl ester
17 Carbamic acid 1-(3-chloro-phenyl)-2-tetrazol-2-yl-ethyl ester
18 Carbamic acid 1-m-tolyl-2-[1,2,3]triazol-2-yl-ethyl ester
19 Carbamic acid 2-tetrazol-2-yl-1-m-tolyl-ethyl ester
20 Carbamic acid (R)-1-(2-chloro-phenyl)-2-tetrazol-2-yl-ethyl ester
21 Carbamic acid (S)-1-(2-chloro-phenyl)-2-tetrazol-2-yl-ethyl ester
22 Carbamic acid (R)-1-(2-chloro-phenyl)-2-tetrazol-1-yl-ethyl ester
23 Carbamic acid (S)-1-(2-chloro-phenyl)-2-tetrazol-1-yl-ethyl ester
24 Carbamic acid 2-tetrazol-2-yl-1-o-tolyl-ethyl ester
25 Carbamic acid 1-(3,4-dichloro-phenyl)-2-[1,2,3]triazol-2-yl-ethyl ester
26 Carbamic acid 1-(3,4-dichloro-phenyl)-2-tetrazol-2-yl-ethyl ester
27 Carbamic acid 2-tetrazol-2-yl-1-(3-trifluoromethyl-phenyl)-ethyl ester
28 Carbamic acid 2-[1,2,3]triazol-2-yl-1-(3-trifluoromethyl-phenyl)-ethyl ester
29 Carbamic acid 1-(2,4-dichloro-phenyl)-2-[1,2,3]triazol-2-yl-ethyl ester
30 Carbamic acid 1-(2,4-dichloro-phenyl)-2-tetrazol-2-yl-ethyl ester
31 Carbamic acid 2-tetrazol-2-yl-1-(4-trifluoromethyl-phenyl)-ethyl ester
32 Carbamic acid 2-[1,2,3]triazol-2-yl-1-(4-trifluoromethyl-phenyl)-ethyl ester
33 Carbamic acid (R)-1-(2-chloro-phenyl)-2-[1,2,3]triazol-2-yl-ethyl ester
34 Carbamic acid (S)-1-(2-chloro-phenyl)-2-[1,2,3]triazol-2-yl-ethyl ester
35 Carbamic acid 1-(2-chloro-phenyl)-2-tetrazol-1-yl-ethyl ester
36 Carbamic acid (R)-1-(2-chloro-phenyl)-2-[1,2,3]triazol-1-yl-ethyl ester
37 Carbamic acid (S)-1-(2-chloro-phenyl)-2-[1,2,3]triazol-1-yl-ethyl ester
38 Carbamic acid 1-(2-chloro-phenyl)-2-[1,2,3]triazol-1-yl-ethyl ester
39 Carbamic acid 2-[1,2,3]triazol-2-yl-1-(2-trifluoromethyl-phenyl)-ethyl ester
40 Carbamic acid 2-chloro-1-phenyl-2-tetrazol-1-yl-ethyl ester
41 Carbamic acid (S)-1-(4-chloro-phenyl)-2-tetrazol-2-yl-ethyl ester
42 Carbamic acid (R)-1-(4-chloro-phenyl)-2-tetrazol-2-yl-ethyl ester
43 Carbamic acid 1-(2-chloro-phenyl)-2-(5-methyl-tetrazol-2-yl)-ethyl ester
44 Carbamic acid 1-(2-chloro-phenyl)-2-(5-methyl-tetrazol-1-yl)-ethyl ester
45 Methyl-carbamic acid (R)-1-(2-chloro-phenyl)-2-tetrazol-2-yl-ethyl ester
46 Ethyl-carbamic acid (R)-1-(2-chloro-phenyl)-2-tetrazol-2-yl-ethyl ester
47 Phenyl-carbamic acid (R)-1-(2-chloro-phenyl)-2-tetrazol-2-yl-ethyl ester 48 Carbamic acid (R)-2-tetrazol-2-yl-1-(2-trifluoromethyl-phenyl)-ethyl ester
49 Carbamic acid (S)-2-tetrazol-2-yl-1-(2-trifluoromethyl-phenyl)-ethyl ester
50 Carbamic acid 1-(2-chloro-phenyl)-2-(5-phenyl-tetrazol-2-yl)-ethyl ester
51 Methyl-carbamic acid 1-(2-chloro-phenyl)-2-(5-phenyl-tetrazol-2-yl)-ethyl ester
52 Cyclopropyl-carbamic acid (R)-1-(2-chloro-phenyl)-2-tetrazol-2-yl-ethyl ester
53 Carbamic acid (R)-1-(2-chloro-phenyl)-2-(5-phenyl-tetrazol-2-yl)-ethyl ester
54 Methyl-carbamic acid (R)-1-(2-chloro-phenyl)-2-(5-phenyl-tetrazol-2-yl)-ethyl ester
55 Carbamic acid 1-phenyl-3-tetrazol-2-yl-propyl ester
56 Carbamic acid 1-(2-chloro-phenyl)-2-[5-(2,3-dichloro-phenyl)-tetrazol-2-yl]-ethyl ester
57 Methyl-carbamic acid 1-(2-chloro-phenyl)-2-[5-(2,3-dichloro-phenyl)-tetrazol-2-yl]-ethyl ester
58 Carbamic acid 1-(4-hydroxy-phenyl)-2-tetrazol-2-yl-ethyl ester
59 Carbamic acid (S)-1-(2-chloro-phenyl)-2-(5-phenyl-tetrazol-2-yl)-ethyl ester
60 Methyl-carbamic acid (S)-1-(2-chloro-phenyl)-2-(5-phenyl-tetrazol-2-yl)-ethyl ester
61 Carbamic acid (S)-1-(2-chloro-phenyl)-2-(5-phenyl-tetrazol-1-yl)-ethyl ester
62 Methyl-carbamic acid (S)-1-(2-chloro-phenyl)-2-(5-phenyl-tetrazol-1-yl)-ethyl ester
63 Carbamic acid 1-phenyl-3-tetrazol-1-yl-propyl ester
64 Carbamic acid 1-phenyl-3-tetrazol-1-yl-propyl ester
65 Carbamic acid 1-(2-chloro-phenyl)-2-[5-(2,3-dichloro-phenyl)-tetrazol-1-yl]-ethyl ester
66 Methyl-carbamic acid 1-(2-chloro-phenyl)-2-[5-(2,3-dichloro-phenyl)-tetrazol-1-yl]-ethyl ester
67 Carbamic acid 1-(3-chloro-phenyl)-2-tetrazol-2-yl-propyl ester
68 Methyl-carbamic acid 1-(3-chloro-phenyl)-2-tetrazol-2-yl-propyl ester
69 Carbamic acid 1-(3-chloro-phenyl)-2-tetrazol-1-yl-propyl ester
70 Carbamic acid 1-(2-chloro-phenyl)-3-[1,2,3]triazol-2-yl-propyl ester
71 Carbamic acid 1-(2-chloro-phenyl)-2-(5-pyridin-2-yl-tetrazol-2-yl)-ethyl ester
72 Carbamic acid 2-(5-amino-tetrazol-2-yl)-1-(2-chloro-phenyl)-ethyl ester
73 Carbamic acid 1-(3-chloro-phenyl)-2-[1,2,3]triazol-2-yl-propyl ester
74 Methyl-carbamic acid 1-(3-chloro-phenyl)-2-[1,2,3]triazol-2-yl-propyl ester
75 Ethyl-carbamic acid 1-(2-chloro-phenyl)-2-(5-pyridin-2-yl-tetrazol-2-yl)-ethyl ester
76 Carbamic acid 1-(4-chloro-phenyl)-2-tetrazol-2-yl-propyl ester
77 Methyl-carbamic acid 1-(4-chloro-phenyl)-2-tetrazol-2-yl-propyl ester
78 Carbamic acid 1-(4-chloro-phenyl)-2-tetrazol-1-yl-propyl ester
79 Methyl-carbamic acid 1-(4-chloro-phenyl)-2-tetrazol-1-yl-propyl ester
80 Carbamic acid 1-(3,4-dichloro-phenyl)-2-tetrazol-2-yl-propyl ester
81 Methyl-carbamic acid 1-(3,4-dichloro-phenyl)-2-tetrazol-2-yl-propyl ester
82 Carbamic acid 1-(3,4-dichloro-phenyl)-2-tetrazol-1-yl-propyl ester
83 Methyl-carbamic acid 1-(3,4-dichloro-phenyl)-2-tetrazol-1-yl-propyl ester
84 Carbamic acid 1-(3,4-dimethoxy-phenyl)-2-tetrazol-2-yl-ethyl ester
85 Carbamic acid (S)-1-(4-chloro-phenyl)-2-[1,2,3]triazol-2-yl-ethyl ester
86 Carbamic acid (R)-1-(4-chloro-phenyl)-2-[1,2,3]triazol-2-yl-ethyl ester
87 Carbamic acid (S)-1-(3,4-dichloro-phenyl)-2-[1,2,3]triazol-2-yl-ethyl ester
88 Carbamic acid (R)-1-(3,4-dichloro-phenyl)-2-tetrazol-2-yl-ethyl ester
89 Carbamic acid 1-(2,5-dichloro-phenyl)-2-tetrazol-2-yl-ethyl ester
90 Carbamic acid 1-(2,5-dichloro-phenyl)-2-tetrazol-1-yl-ethyl ester
91 Carbamic acid (R)-1-(3,4-dichloro-phenyl)-2-[1,2,3]triazol-2-yl-ethyl ester
92 Carbamic acid (R)-1-(3,4-dichloro-phenyl)-2-[1,2,3]triazol-1-yl-ethyl ester
93 Carbamic acid 1-(4-phenoxy-phenyl)-2-tetrazol-2-yl-ethyl ester
94 Carbamic acid 1-(4-phenoxy-phenyl)-2-tetrazol-1-yl-ethyl ester
95 Carbamic acid 1-(2,5-dichloro-phenyl)-2-[1,2,3]triazol-2-yl-ethyl ester
96 Carbamic acid (S)-1-(3,4-dichloro-phenyl)-2-tetrazol-2-yl-ethyl ester
97 Carbamic acid (S)-1-(3,4-dichloro-phenyl)-2-tetrazol-1-yl-ethyl ester
98 Carbamic acid 1-(2,6-dichloro-phenyl)-2-tetrazol-2-yl-ethyl ester
99 Carbamic acid 1-(2,6-dichloro-phenyl)-2-[1,2,3]triazol-2-yl-ethyl ester
100 Carbamic acid 1-(2,6-dichloro-phenyl)-2-[1,2,3]triazol-1-yl-ethyl ester
101 Carbamic acid 1-(2,4-dichloro-phenyl)-2-tetrazol-1-yl-ethyl ester
102 Carbamic acid 1-naphthalen-2-yl-2-tetrazol-2-yl-ethyl ester
103 Carbamic acid (R)-1-(2,4-dichloro-phenyl)-2-tetrazol-2-yl-ethyl ester
104 Carbamic acid 1-naphthalen-2-yl-2-tetrazol-1-yl-ethyl ester
105 Carbamic acid 2-tetrazol-2-yl-1-(2,3,4-trimethoxy-phenyl)-ethyl ester
106 Carbamic acid 2-tetrazol-1-yl-1-(2,3,4-trimethoxy-phenyl)-ethyl ester
107 Carbamic acid 2-tetrazol-2-yl-1-(3,4,5-trimethoxy-phenyl)-ethyl ester
108 Carbamic acid 1-benzo[1,3]dioxol-5-yl-2-tetrazol-2-yl-ethyl ester
109 Carbamic acid 1-benzo[1,3]dioxol-5-yl-2-tetrazol-1-yl-ethyl ester
110 Carbamic acid 1-(4-dimethylamino-phenyl)-2-tetrazol-2-yl-ethyl ester
111 Carbamic acid 2-tetrazol-2-yl-1-(2,4,6-trimethyl-phenyl)-ethyl ester
112 Carbamic acid 2-tetrazol-1-yl-1-(2,4,6-trimethyl-phenyl)-ethyl ester
113 Carbamic acid (S)-1-(2,4-dichloro-phenyl)-2-tetrazol-2-yl-ethyl ester
114 Carbamic acid (S)-1-(2,4-dichloro-phenyl)-2-[1,2,3]triazol-2-yl-ethyl ester
115 Carbamic acid (R)-1-(2,4-dichloro-phenyl)-2-[1,2,3]triazol-2-yl-ethyl ester 116 Carbamic acid 2-phenyl-1-tetrazol-2-ylmethyl-ethyl ester
117 Carbamic acid 2-phenyl-1-tetrazol-1-ylmethyl-ethyl ester
118 Carbamic acid 1-(4-tert-butyl-phenyl)-2-tetrazol-2-yl-ethyl ester
119 Carbamic acid 1-(4-tert-butyl-phenyl)-2-tetrazol-1-yl-ethyl ester
120 Carbamic acid 1-(4-chloro-3-trifluoromethyl-phenyl)-2-[1,2,3]triazol-2-yl-ethyl ester
121 Carbamic acid 1-(4-chloro-3-trifluoromethyl-phenyl)-2-[1,2,3]triazol-1-yl-ethyl ester
122 Carbamic acid (S)-1-(2,6-dichloro-phenyl)-2-tetrazol-1-yl-ethyl ester
123 Carbamic acid (R)-1-(2,6-dichloro-phenyl)-2-tetrazol-1-yl-ethyl ester
124 Carbamic acid 1-indan-5-yl-2-tetrazol-1-yl-ethyl ester
125 Carbamic acid 1-indan-5-yl-2-tetrazol-2-yl-ethyl ester
126 Carbamic acid (R)-1-(2,6-dichloro-phenyl)-2-tetrazol-2-yl-ethyl ester
127 Carbamic acid (S)-1-(2,6-dichloro-phenyl)-2-tetrazol-2-yl-ethyl ester
128 Carbamic acid 2-(2,4-dichloro-phenoxy)-1-tetrazol-2-ylmethyl-ethyl ester
129 O-1-(2-Chloro-phenyl)-2-tetrazol-2-yl ethyl allophanate
130 Carbamic acid (R)-1-(2,4-dichloro-phenyl)-2-[1,2,3]triazol-1-yl-ethyl ester
131 Carbamic acid 1-phenyl-2-tetrazol-1-yl-ethyl ester
132 Carbamic acid 1-(3,4-difluoro-phenyl)-2-tetrazol-2-yl-ethyl ester
133 Carbamic acid 1-(3,4-difluoro-phenyl)-2-tetrazol-1-yl-ethyl ester
134 Carbamic acid 1-(3,4-difluoro-phenyl)-2-[1,2,3]triazol-2-yl-ethyl ester
135 Carbamic acid 1-(3,4-difluoro-phenyl)-2-[1,2,3]triazol-1-yl-ethyl ester
136 Carbamic acid 1-(2-fluoro-phenyl)-2-tetrazol-2-yl-ethyl ester
137 Carbamic acid 1-(2-fluoro-phenyl)-2-tetrazol-1-yl-ethyl ester
138 4-Benzyl-piperidine-1-carboxylic acid 1-(2-chloro-phenyl)-2-tetrazol-2-yl-ethyl ester
143 4-Phenyl-piperazine-1-carboxylic acid 1-(2-chloro-phenyl)-2-tetrazol-2-yl-ethyl ester
144 4-Phenyl-piperazine-1-carboxylic acid 1-(2-chloro-phenyl)-2-tetrazol-1-yl-ethyl ester
145 4-(4-Fluoro-benzoyl)-piperidine-1-carboxylic acid 1-(2-chloro-phenyl)-2-tetrazol-2-yl-ethyl ester
146 4-Benzyl-piperidine-1-carboxylic acid 1-(2-chloro-phenyl)-2-tetrazol-1-yl-ethyl ester
147 1-Benzyl-4-[1-(2-chloro-phenyl)-2-tetrazol-2-yl-ethoxycarbonyl]-piperazin-1-ium
148 Carbamic acid 2-(3,4-dichloro-phenoxy)-1-tetrazol-2-ylmethyl-ethyl ester
149 Imidazole-1-carboxylic acid 2-(3,4-dichloro-phenoxy)-1-tetrazol-1-ylmethyl-ethyl ester
150 Carbamic acid 2-(4-chloro-phenoxy)-1-tetrazol-1-ylmethyl-ethyl ester
151 Imidazole-1-carboxylic acid 2-(4-chloro-phenoxy)-1-tetrazol-1-ylmethyl-ethyl ester
152 Carbamic acid 2-(4-chloro-phenoxy)-1-tetrazol-2-ylmethyl-ethyl ester
153 4-Benzyl-piperidine-1-carboxylic acid 1-phenyl-2-tetrazol-1-yl-ethyl ester
154 4-Benzyl-piperidine-1-carboxylic acid 1-phenyl-2-tetrazol-2-yl-ethyl ester
155 Carbamic acid 2-(2-chloro-phenoxy)-1-tetrazol-2-ylmethyl-ethyl ester
156 4-Benzyl-piperidine-1-carboxylic acid 2-(2-chloro-phenoxy)-1-tetrazol-2-ylmethyl-ethyl ester
157 Carbamic acid 2-(2-chloro-phenoxy)-1-tetrazol-1-ylmethyl-ethyl ester
158 4-Benzyl-piperidine-1-carboxylic acid 2-(2-chloro-phenoxy)-1-tetrazol-1-ylmethyl-ethyl ester
161 Carbamic acid 1-(2,4-difluoro-phenyl)-2-tetrazol-2-yl-ethyl ester
162 Carbamic acid 1-(2,4-difluoro-phenyl)-2-tetrazol-1-yl-ethyl ester
163 4-Benzyl-piperidine-1-carboxylic acid (S)-1-(2-chloro-phenyl)-2-[1,2,3]triazol-2-yl-ethyl ester
164 4-Benzyl-piperidine-1-carboxylic acid (R)-1-(2-chloro-phenyl)-2-tetrazol-2-yl-ethyl ester
165 Carbamic acid 1-(2,4-dimethyl-phenyl)-2-[1,2,3]triazol-2-yl-ethyl ester
166 4-Benzyl-piperidine-1-carboxylic acid (S)-1-(2-chloro-phenyl)-2-tetrazol-2-yl-ethyl ester
167 [2-(3,4-Dihydroxy-phenyl)-ethyl]-carbamic acid 1-(2-chloro-phenyl)-2-tetrazol-2-yl-ethyl ester
168 [2-(3,4-Dihydroxy-phenyl)-ethyl]-carbamic acid 1-(2-chloro-phenyl)-2-tetrazol-1-yl-ethyl ester
169 4-Benzyl-piperidine-1-carboxylic acid (R)-1-(2-chloro-phenyl)-2-[1,2,3]triazol-2-yl-ethyl ester
170 Carbamic acid 2-(4-chloro-phenoxy)-1-[1,2,3]triazol-2-ylmethyl-ethyl ester
171 Carbamic acid 2-(4-chloro-phenoxy)-1-[1,2,3]triazol-1-ylmethyl-ethyl ester
172 4-Benzyl-piperidine-1-carboxylic acid 2-(4-chloro-phenoxy)-1-tetrazol-2-ylmethyl-ethyl ester
173 4-Benzyl-piperidine-1-carboxylic acid 2-(4-chloro-phenoxy)-1-tetrazol-1-ylmethyl-ethyl ester
174 4-(4-Methoxy-benzyl)-piperidine-1-carboxylic acid 1-(2-chloro-phenyl)-2-tetrazol-2-yl-ethyl ester
175 4-(3,4-Dichloro-benzyl)-piperidine-1-carboxylic acid 1-(2-chloro-phenyl)-2-tetrazol-2-yl-ethyl ester
176 4-Pyridin-4-ylmethyl-piperidine-1-carboxylic acid 1-(2-chloro-phenyl)-2-tetrazol-2-yl-ethyl ester
177 4-(4-Fluoro-benzyl)-piperidine-1-carboxylic acid 1-(2-chloro-phenyl)-2-tetrazol-2-yl-ethyl ester
178 3-(4-Fluoro-benzyl)-piperidine-1-carboxylic acid 1-(2-chloro-phenyl)-2-tetrazol-2-yl-ethyl ester
179 4-(4-Chloro-benzyl)-piperidine-1-carboxylic acid 1-(2-chloro-phenyl)-2-tetrazol-2-yl-ethyl ester
180 3-(4-Chloro-phenyl)-pyrrolidine-1-carboxylic acid 1-(2-chloro-phenyl)-2-tetrazol-2-yl-ethyl ester
181 3-Phenethyl-pyrrolidine-1-carboxylic acid 1-(2-chloro-phenyl)-2-tetrazol-2-yl-ethyl ester
182 4-[1,2,3]Triazol-2-ylmethyl-piperidine-1-carboxylic acid 1-(2-chloro-phenyl)-2-tetrazol-2-yl-ethyl ester
183 3-Tetrazol-2-ylmethyl-piperidine-1-carboxylic acid 1-(2-chloro-phenyl)-2-tetrazol-2-yl-ethyl ester
184 3-[1,2,3]Triazol-2-ylmethyl-piperidine-1-carboxylic acid 1-(2-chloro-phenyl)-2-tetrazol-2-yl-ethyl ester
185 4-Benzoyl-piperidine-1-carboxylic acid 1-(2-chloro-phenyl)-2-tetrazol-2-yl-ethyl ester
186 4-(4-Chloro-benzoyl)-piperidine-1-carboxylic acid 1-(2-chloro-phenyl)-2-tetrazol-2-yl-ethyl ester
187 4-(4-Methoxy-benzoyl)-piperidine-1-carboxylic acid 1-(2-chloro-phenyl)-2-tetrazol-2-yl-ethyl ester
188 4-[1,2,3]Triazol-1-ylmethyl-piperidine-1-carboxylic acid 1-(2-chloro-phenyl)-2-tetrazol-2-yl-ethyl ester
189 4-Tetrazol-2-ylmethyl-piperidine-1-carboxylic acid 1-(2-chloro-phenyl)-2-tetrazol-2-yl-ethyl ester 190 4-[1,2,3]Triazol-2-yl-piperidine-1-carboxylic acid 1-(2-chloro-phenyl)-2-tetrazol-2-yl-ethyl ester
191 4-(3,4-Dichloro-benzyl)-piperidine-1-carboxylic acid 1-(2,5-dichloro-phenyl)-2-tetrazol-2-yl-ethyl ester
192 4-(5-Phenyl-tetrazol-2-yl)-piperidine-1-carboxylic acid 1-(2-chloro-phenyl)-2-tetrazol-2-yl-ethyl ester
193 4-[1,2,3]Triazol-1-yl-piperidine-1-carboxylic acid 1-(2-chloro-phenyl)-2-tetrazol-2-yl-ethyl ester
194 4-(3,4-Dichloro-benzyl)-piperidine-1-carboxylic acid 1-(2,4-dichloro-phenyl)-2-tetrazol-2-yl-ethyl ester
195 4-(3,4-Dichloro-benzyl)-piperidine-1-carboxylic acid 1-(3,4-dichloro-phenyl)-2-tetrazol-2-yl-ethyl ester
196 3-(4-Chloro-benzyl)-pyrrolidine-1-carboxylic acid 1-(2-chloro-phenyl)-2-tetrazol-2-yl-ethyl ester
197 4-(3,5-Bis-trifluoromethyl-benzyl)-piperidine-1-carboxylic acid 1-(2-chloro-phenyl)-2-tetrazol-2-yl-ethyl ester
198 3-(5-Methyl-tetrazol-2-ylmethyl)-piperidine-1-carboxylic acid 1-(2-chloro-phenyl)-2-tetrazol-2-yl-ethyl ester
199 4-(5-Methyl-tetrazol-2-ylmethyl)-piperidine-1-carboxylic acid 1-(2-chloro-phenyl)-2-tetrazol-2-yl-ethyl ester
200 4-(3,4-Dichloro-benzyl)-piperidine-1-carboxylic acid 1-(2-chloro-phenyl)-2-[1,2,3]triazol-2-yl-ethyl ester
201 4-(3,4-Dichloro-benzyl)-piperidine-1-carboxylic acid 1-(2-chloro-phenyl)-2-tetrazol-1-yl-ethyl ester
202 3-Phenethyl-pyrrolidine-1-carboxylic acid 1-(2,5-dichloro-phenyl)-2-tetrazol-2-yl-ethyl ester
203 3-Phenethyl-pyrrolidine-1-carboxylic acid 1-(2,4-dichloro-phenyl)-2-tetrazol-2-yl-ethyl ester
204 3-Phenethyl-pyrrolidine-1-carboxylic acid 1-(3,4-dichloro-phenyl)-2-tetrazol-2-yl-ethyl ester
205 3-Phenethyl-pyrrolidine-1-carboxylic acid 2-(2-chloro-phenoxy)-1-[1,2,3]triazol-2-ylmethyl-ethyl ester
206 3-Phenethyl-pyrrolidine-1-carboxylic acid 2-(2,4-dichloro-phenoxy)-1-[1,2,3]triazol-2-ylmethyl-ethyl ester
207 3-Phenethyl-pyrrolidine-1-carboxylic acid 2-(3,4-dichloro-phenoxy)-1-[1,2,3]triazol-2-ylmethyl-ethyl ester
208 3-Phenethyl-pyrrolidine-1-carboxylic acid 2-(2,5-dichloro-phenoxy)-1-tetrazol-2-ylmethyl-ethyl ester
209 Carbamic acid 2-(2-chloro-phenoxy)-1-[1,2,3]triazol-2-ylmethyl-ethyl ester
210 Carbamic acid 2-(3,4-dichloro-phenoxy)-1-[1,2,3]triazol-2-ylmethyl-ethyl ester
211 Carbamic acid 2-(2,4-dichloro-phenoxy)-1-[1,2,3]triazol-2-ylmethyl-ethyl ester
212 Carbamic acid 2-(2,5-dichloro-phenoxy)-1-tetrazol-2-ylmethyl-ethyl ester
213 4-(4-Fluoro-benzoyl)-piperidine-1-carboxylic acid 1-(3,4-dichloro-phenyl)-2-tetrazol-2-yl-ethyl ester
214 4-(4-Fluoro-benzoyl)-piperidine-1-carboxylic acid 1-(2,4-dichloro-phenyl)-2-tetrazol-2-yl-ethyl ester
215 4-(4-Fluoro-benzoyl)-piperidine-1-carboxylic acid 1-(2,5-dichloro-phenyl)-2-tetrazol-2-yl-ethyl ester
216 4-(3,4-Dichloro-benzyl)-piperidine-1-carboxylic acid 2-(2-chloro-phenoxy)-1-tetrazol-2-ylmethyl-ethyl ester
217 4-(3,4-Dichloro-benzyl)-piperidine-1-carboxylic acid 2-(2,4-dichloro-phenoxy)-1-tetrazol-2-ylmethyl-ethyl ester
218 4-(3,4-Dichloro-benzyl)-piperidine-1-carboxylic acid 2-(3,4-dichloro-phenoxy)-1-tetrazol-2-ylmethyl-ethyl ester
219 3-[2-(4-Methoxy-phenyl)-ethyl]-pyrrolidine-1-carboxylic acid 1-(2-chloro-phenyl)-2-tetrazol-2-yl-ethyl ester
220 4-(3,4-Dichloro-benzyl)-piperidine-1-carboxylic acid 1-phenyl-2-tetrazol-2-yl-ethyl ester
221 Carbamic acid 1-(4-benzyloxy-phenyl)-2-tetrazol-2-yl-ethyl ester
222 Carbamic acid 1-(4-benzyloxy-phenyl)-2-tetrazol-1-yl-ethyl ester
223 methyl-carbamic acid-1-(2-chloro-phenyl)-2-tetrazol-2-yl-ethyl ester
224 methyl-carbamic acid (S)-1-(2-chloro-phenyl)-2-tetrazol-2-yl-ethyl ester
225 4-benzyl-piperidine-1-carboxylic acid-1-(2-chloro-phenyl)-2-[1,2,3]triazol-2-yl-ethyl ester
226 4-benzyl-piperidine-1-carboxylic acid (S)-1-(2-chloro-phenyl)-2-[1,2,3]triazol-2-yl-ethyl ester In utilizing the compounds of the invention represented by the general structural formula (IX) for the treatment of diseases of the central nervous system, particularly the treatment of anxiety, depression, convulsion, epilepsy, migraine, bipolar disorder, drug abuse, smoking, ADHD, obesity, sleep disorder, neuropathic pain, cognitive impairment, smoke and muscle spasm, it is preferred to administer the compounds orally. For oral administration, the compounds of formula (IX) are preferably combined with a pharmaceutical carrier. The ratio of the carrier to a compound of formula (IX) is not critical to achieve the desired effects on the central nervous system of the host requiring such treatment, and can vary considerably, depending on whether the composition is to be filled into capsules or formed into tablets. In tableting, it is usually desirable to employ at least as much pharmaceutical carrier as the pharmaceutically active ingredients. Various pharmaceutical carriers or mixtures thereof can be used. Suitable carriers, for example, comprise mixtures of lactose, dibasic calcium phosphate and corn starch. Other pharmaceutically acceptable ingredients can be further added, including lubricants such as magnesium stearate.

The compounds of formula (IX) can be formulated, using conventional inert pharmaceutical adjuvant materials, into dosage forms that are suitable for oral or parenteral administration. Such dosage forms include tablets, suspensions, solutions, and the like. Furthermore, the compounds of the invention can be administered in the form of hard or soft capsules. Examples of suitable inert adjuvant materials that can be used in formulating the compounds of formula (IX) into oral and parenteral dosage forms will be immediately apparent to persons skilled in the art. These adjuvant materials include, for example, water, gelatin, lactose, starch, magnesium stearate, talc, vegetable oils, gums, polyalkylene glycols, and the like. Moreover, preservatives, stabilizers, wetting agents, emulsifying agents, salts for altering osmotic pressure, buffers, and the like, can be incorporated, if desired, into such formulations.

The therapeutic use of the racemic or enantiomerically enriched compounds of general structural formula (IX) and their pharmaceutically useful salts have been established by the following tests.

Light-Dark Box Test Methods

Light-Dark Box (LDB) test, one of the unconditioned conflict tests, was used to investigate anxiolytic activity for several drugs such as Diazepam, Buspirone, etc (Allikmets et al, 1996; Belzung and Griebel, 2001; Cutler and Aitken, 1991; Leyre et al, 2004). In the present study, anxiolytic effect of azole compounds containing carbamoyl group represented by general structural formula (IX) was investigated on the LDB test in mice.

The animals were treated with compound 30 min prior to testing. The light-dark box consisted of a plexiglas apparatus measuring 45 cm×27 cm×27 cm (L×W×H), and was partitioned into two compartments, one fully opaque (dark compartment made of black plexiglas: 18 cm of total length of apparatus), while the second was lit from the compartment ceiling by a 100 W bulb. A small opening (7×7 cm) in the partition wall allowed free passage between the light and dark compartments.

Animals were placed at the lit compartment first, and the latency for escape into dark was checked and tested in the LDB for 5 min after the first entering into dark box. The animal, which the latency was over 2 min, was excluded from the test. Total time spent in the light compartment was counted. Movement of animal was checked through the TV-CCD camera by an experienced observer blind to the conditions of the experiment. A mouse whose four paws were in the new box was considered as having changed box.

The compounds with a higher % duration value in the light box are more potent as anxiolytics.

Maximal Electro Shock-induced Tonic Seizure Test Methods

The "Maximal ElectroShock (MES)" test is a well-established pharmacological screening method for anticonvulsants against tonic-clonic seizures. The procedure employed in the MES test for anticonvulsants is as follows. The compounds to be tested were dissolved in 30% PEG400 and administered ip and po into animals. After the designated number of hours, maximal electroshock (50 mA, 60 Hz, 0.2 sec) was applied into animals via corneal electrodes using IITC Life Science model 11A Shocker. Anticonvulsant activity is demonstrated by the protection against MES-induced hindlimb tonic extension. Median efficacy dose (ED50) levels were determined using three different dose levels with at least 8 mice in each group. Compounds with smaller ED50 value and higher protection rate are more potent as anticonvulsants.

Pentylenetetrazol-induced Clonic Seizure Test Methods

The "Pentylenetetrazol (PTZ)" test for anticonvulsant and antianxiety activity was also carried out. Compounds that antagonize the effects of subcutaneous PTZ-induced clonic seizures are known to elevate the seizure threshold, hence are generally useful in preventing absence seizures.

The procedure employed in the PTZ test is as follows. The compounds to be tested were dissolved in 30% PEG400 and administered ip and po into animals. After the designated number of hours, each animal was injected subcutaneously with 100 mg/kg of PTZ (CD97 dose) and observed for up to 30 minutes for the presence or absence of clonic spasms over 5 seconds. Median efficacy dose (ED50) levels were determined using three different dose levels with 8 mice in each group. The compounds with a smaller ED50 value and higher protection rate are more potent as anticonvulsant and anxiolytics.

Forced Swimming Test Methods

The "Forced swimming test (FST)" for antidepressant activity was also carried out. The procedure employed in the FST for antidepressant is as follows. The compounds to be tested were dissolved in 30% PEG400 and administered ip and po into animals. 30 min later, the immobility time during post 4 minutes of 6 minutes experiment time was measured. The compounds with a higher reduction % value of immobility are more potent as antidepressants

GABA-A Receptor (TBPS Site) Binding Assay Methods

Compounds of the inventions were tested for specific binding to TBPS (t-butyl bicyclophosphorothionate) site, an allosteric modulator site of GABA-A receptor as modified from G. Maksay and M. Simonyi, Eur. J. Pharmacol. 1985, 117(2), 275. and Gee, K. W. et al., J. Pharm. Exp. Ther. 1988, 246, 803.

This binding assay was performed using [35S] TBPS as radioligand in washed crude membrane homogenate from rat brains. Membrane preparations were carried out according to procedure described below. Sprague-Dawley (SD) rat weighting 230 g were killed by decapitation and their whole brains were rapidly removed and its cerebellums were excluded. The dissected brains were homogenized for 30 sec in 10 volumes (W/V) of ice-cold 0.32 M Sucrose and 50 mM Tris-citrate buffer pH 7.4 using glass homogenate. The homogenate was centrifuged at 2,000×g for 5 min at 4° C. And the supernatant re-centrifuged at 50,000×g for 20 min at 4° C. The supernatant was discarded and the resulting pellets were resuspended in 10 volumes (W/V) of ice-cold 50 mM Tris-citrate buffer pH 7.4. And then the suspended pellet was centrifuged at 50,000×g for 20 min at 4° C. The resulting pellets were suspended again in 32 volumes (W/V) of ice-cold 50 mM Tris-citrate buffer pH 7.4 with 0.05% Triton X-100 and then incubated in 37° C. for 60 min using a water bath. The incubated suspension was centrifuged at 50,000×g for 20 min at 4° C. Resuspending and centrifugation step of the remained pellets were repeated twice at the same manner and final pellets were resuspended in 10 volumes (W/V) of ice-cold 50 mM Tris-citrate buffer pH 7.4 to enable distribution of 2 ml aliquot in microcentrifuge tube, which were used immediately or kept at −80° C. for no more than 1 month before use.

For TBPS site binding assay, 50 µl of the tested compound were added to 100 µg membrane protein suspended in 0.15 ml of 50 mM Tris-citrate buffer with 200 mM NaCl pH 7.4 in presence of 2 nM of [35S] TBPS. The incubation of mixtures were carried out for 1.5 hours at 25° C. and then rapidly filtered over Whatman GF/C glass fiber filters, followed by twice 4.5 ml rinses with ice-cold incubation buffer. The filters were placed in counting vials and 4 ml scintillation solution. The vials were counted in a Beckman scintillation counter. Non-specific binding was determined in parallel incubations with 100 µM picrotoxin.

IC50 values for TBPS site binding assay was calculated using Graphpad PRISM v.3.00. The compounds with a smaller IC50 value or higher inhibition % are more potent as GABA allosteric modulator.

Dopamine Transport Assay Methods (Measurement of Dopamine Uptake)

The "Dopamine Transport (DAT)" assay for dopamine uptake inhibition was also carried out. In order to test dopamine uptake inhibition, compounds of the inventions were assayed as modified from Zhaoping Liu et. al., Neuropharmacology, 2001, 41, 464.

Cultured CHO cells were infected with recombinant plasmid, DAT-pCDNA3, which encodes rat dopamine transporter. Several subclones were selected and assayed for [3H] dopamine uptake. The clone with the highest uptake, designated D8, was chosen for Dopamine transport assay of compounds.

For the Dopamine transport assay, D8 cells were cultured in 48-well plate using RMPI1640 containing 10% FCS. D8 cells, grown to 60,000 cells per well, each wells were rinsed once with phosphate buffered saline (PBS) and pre-incubated in 100 μl Hank's balanced salt solution (HBSS) for 10 min at room temperature. The buffer was then changed to 50 μl HBSS containing the tested compounds and 350 μl HBSS containing reaction components ([3H] dopamine, ascorbic acid and pargyline). Final concentrations of [3H] dopamine, ascorbic acid and pargyline are 151 nM, 100 μM and 100 μM, respectively. The cells were incubated for 20 min at room temperature and the reaction was terminated by aspiration of the buffer and washed three times with 1 ml cold BS. The cells were then solubilized in 2N NaOH and an aliquot was measured by liquid scintillation counting to quantify the uptake of [3H] dopamine. The compounds with higher inhibition % are more potent as dopamine uptake inhibitor.

Test results obtained with the compounds of general structural formula (IX) and pharmaceutically useful salts of the invention are set forth in Table I.

TABLE I

| Compound # | Mice LDB % Duration in the light box | Mice MES $ED_{50}$ or Protection % (mpk/peak time) | Mice PTZ $ED_{50}$ or Protection % (mpk/peak time) | Mice FST Reduction of immobility % | TBPS Inhibition % (At 100 μM) | DAT Inhibition % (At 10 μM) |
|---|---|---|---|---|---|---|
| 1 | N.T | 10.7/0.5 hr | 24.5/0.5 hr | N.S | 18.3% | 47.3% |
| 2 | 180% | 8.6/0.5 hr | 5.9/0.5 hr | N.S | 11.2% | N.T |
| 4 | N.T | 66.7% (30/0.5 hr) | N.T | 40.3% | −2.3% | 41.5% |
| 5 | N.T | 18.4/0.5 hr | N.T | 71.7% | 14.5% | N.T |
| 7 | N.T | 26.2/0.5 hr | N.T | N.T | 3.5% | −21.1% |
| 10 | N.T | 21.3/0.5 hr | N.T | 45.1% | 35.9% | N.T |
| 20 | 285% | 4.24/0.5 hr | 3.76/0.5 hr | −24.3% | 25.1% | 7.1% |
| 21 | N.T | 14.2/0.5 hr | 28.8/0.5 hr | N.T | 12.6% | 20.9% |
| 25 | N.T | 100% (50/0.5, 1, 4 hr) | N.T | 94.1% | 74.8% | 70.7% |
| 26 | N.T | 100% (50/0.5, 1, 2, 4 hr) | N.T | 97.5% | 66.3% | 88.2% |
| 29 | 288.5% | 14.4/1 hr | 16.8/1 hr | N.S | $IC_{50}$ = 8.1 μM | −27.5% |
| 30 | 143.6% | 14.9/1 hr | 12.2/1 hr | N.S | 74.9% | 15.1% |
| 33 | N.S | 9.72/0.5 hr | 8.18/0.5 hr | 26.2% | 48.2% | N.T |
| 39 | N.T | 12.5/0.5 hr | N.T | N.T | N.T | N.T |
| 42 | N.T | 18.2/0.5 hr | N.T | 44.1% | N.T | N.T |
| 45 | N.S | 4.88/0.5 hr | 5.81/0.5 hr | N.T | N.T | −58.1% |
| 80 | N.T | 33.3% (30/2, 4 hr) | N.T | 50.6% | 64.8% | N.T |
| 86 | N.T | 21.4/0.5 hr | N.T | N.S | 18.9% | N.T |
| 87 | N.S | 14.8/0.5 hr | N.T | 92.5% | 50.1% | 93.8% |
| 88 | N.T | 19.1/0.5 hr | N.T | 88.4% | 52.8% | N.T |
| 89 | 167.4% | 6.15/1 hr | 14.5/1 hr | N.S | 27.6% | N.T |
| 91 | N.T | 16.0/0.5 hr | N.T | 94.0% | N.T | N.T |
| 96 | N.T | 10.4/0.5 hr | N.T | 95.8% | N.T | 98.4% |
| 98 | N.T | 6.03/0.5 hr | 11.6/0.5 hr | 31.5% | 29.9% | N.T |
| 99 | N.T | 11.6/0.5 hr | 100% (30/0.5, 2 hr) | N.S | 23.6% | N.T |
| 103 | 277.8% | 19.2/1 hr | 5.14/1 hr | N.S | $IC_{50}$ = 13.4 μM | N.T |
| 113 | −172% | 13.0/1 hr | 20.7/1 hr | N.S | N.T | N.T |
| 114 | 172.5% | 33.9/1 hr | 16.9/1 hr | N.S | $IC_{50}$ = 107.4 μM | N.T |
| 115 | 245% (10 mpk, ip) | 12.7/0.25 hr | 8.43/1 hr | N.S | $IC_{50}$ = 4.3 μM | N.T |
| 116 | N.T | 100% (30/0.5, 1 hr) | 33.3% (30/0.5, 1, 2 hr) | 30.0% | N.T | N.T |
| 126 | 241.5% | 2.7/0.5 hr | 5.06/0.5 hr | 72.0% | 0.3% | N.T |
| 129 | N.T | 13.7/0.5 hr | 100% (30/1 hr) | N.S | 5.6% | N.T |
| 130 | N.S | 24.0/0.5 hr | 8.0/0.5 hr | 8.8% | 42.8% | N.T |
| 138 | N.T | 100% (30/2 hr) | 66.7% (30/4 hr) | 35.9% | 49.6% | N.T |
| 148 | N.T | 100% (30/0.5 hr) | 66.7% (30/0.5, 4 hr) | N.S | 76.1% | N.T |
| 175 | N.T | 20.2/0.5 hr | 66.7% (30/4 hr) | N.S | N.T | N.T |
| 181 | N.T | 12.1/0.5 hr | 33.3% (30/1, 2, 4 hr) | 30.6% | N.T | N.T |
| 191 | N.T | 66.7% (30/0.5, 1, 2, 4 hr) | >30 | 50.6% | N.T | N.T |
| 194 | N.T | 11.9/0.5 hr | 33.3% (30/2 hr) | 53.4% | N.T | N.T |
| 195 | N.T | 15.3/0.5 hr | 33.3% (30/0.5, 1 hr) | 31.9% | N.T | N.T |
| 196 | N.T | 15.3/0.5 hr | 33.3% (30/2, 4 hr) | N.S | N.T | N.T |
| 197 | N.T | 6.3/0.5 hr | 100% (30/0.5, 4 hr) | N.S | N.T | N.T |
| 200 | N.T | 100% (30/0.5, 4 hr) | N.T | 25.9% | N.T | N.T |
| 201 | N.T | 100% (30/1, 2, 4 hr) | N.T | 54.0% | N.T | N.T |
| 202 | N.T | 11.4/0.5 hr | 33.3% (30/1, 4 hr) | 81.2% | N.T | N.T |
| 203 | N.T | 100% (30/0.5, 1, 2, 4 hr) | N.T | 44.0% | N.T | N.T |
| 204 | N.T | 100% (30/0.5, 1, 2 hr) | N.T | 51.2% | N.T | N.T |
| 206 | N.T | 100% (30/0.5, 1, 2, 4 hr) | 66.7% (30/2, 4 hr) | 51.4% | N.T | N.T |
| 207 | N.T | 100% (30/0.5, 1, 4 hr) | N.T | 43.4% | N.T | N.T |
| 208 | N.T | 100% (30/0.5, 1, 4 hr) | 33.3% (30/4 hr) | 48.2% | N.T | N.T |

Protection % was evaluated using with 3 mice.
mpk: mg/kg
N.S: Not significant (p > 0.05)
N.T: Not tested As described hereinbefore, the racemic or enantiomerically enriched azole compounds containing carbamoyl group represented by the general structural formula (IX) and pharmaceutically useful salts thereof of the present invention were observed to have anxiolytic and anticonvulsant activity in the LDB test, MES test, PTZ test and TBPS assay. The compounds showing GABA-related activities can be applied to the treatment of sleep disorder or muscle spasms. Furthermore, the racemic or enantiomerically enriched azole compounds containing carbamoyl group represented by the general structural formula (IX) and pharmaceutically useful salts thereof of the present invention were also observed to have antidepressant activity and affinity to dopamine uptake inhibition. Also the compounds acting as dopamine reuptake inhibitors can be developed for the treatment of ADHD, obesity or abuse syndromes of drugs or smoking. The compounds with the anticonvulsant and/or antiepileptic activities may also be used for the treatment of bipolar disorders, migraine prophylaxis, and neuropathic pain as their additional indications. Accordingly the racemic or enantiomerically enriched azole compounds containing carbamoyl group represented by the general structural formula (IX) and pharmaceutically useful salts thereof of the present invention can be used in the treatment of disorders of the central nervous system, especially as anxiety, depression, convulsion, epilepsy, migraine, bipolar disorder, drug abuse, smoking, ADHD, obesity, sleep disorder, neuropathic pain, cognitive impairment, stroke, neurodegeneration and muscle spasm.

The amount of a compound of general structural formula (IX) and pharmaceutically useful salts thereof, which is present in any of the above-described dosage forms, is variable. In the systemic treatment of CNS diseases with an active amount of compounds of the general structural formula (IX) and pharmaceutically useful salts thereof, the dosage is typically from about 0.02 mg to about 250 mg/kg/day (0.001~12.5 g/day in a typical human weighing 50 kg) in single or divided doses, regardless of the route of administration. A more preferred dosage range is from about 0.15 mg/kg/day to about 250 mg/kg/day. Of course, depending upon the exact compound and the exact nature of the individual illness, doses outside this range may be prescribed by the attending physician.

The examples, which follow further, illustrate the invention. All parts are by weight and all temperatures are in degrees centigrade, unless otherwise mentioned. Moreover, unless otherwise stated, NMR spectra were obtained at 200 MHz.

A better understanding of the present invention may be obtained in light of following examples that are set forth to illustrate, but are not to be construed to limit, the present invention.

Preparation of azole compounds containing carbamoyl group of the general structural formula (IX).

EXAMPLE 1

Carbamic acid 1-(2-chloro-phenyl)-2-[1,2,3]triazol-2-yl-ethyl ester

To a solution of 2-bromo-2'-chloroacetophenone (2 mmol) and sodium carbonate (4 mmol) in toluene (100 ml), 1H-1,2,3-triazole (4 mmol) was added. The reaction was refluxed for 4 h and then cooled to 25° C. This solution was then concentrated on a rotary evaporator and diluted with ethyl acetate. This mixture was washed with brine. The resulting organic layer was dried and concentrated in vacuo. The crude product was dissolved in methanol (50 ml) and was added with sodium borohydride (8 mmol) slowly at 0° C. to give alcohol compound represented by the general formula (XII) where in, G is 2-chlorophenyl, m is 0, Y is hydrogen, n is 0 and A is 2N-1,2,3-triazole. After 1 h stirring at room temperature, this solution was concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 4 h, followed by the addition of excess ammonium hydroxide (50 ml). After 4 h stirring at room temperature, the organic layer was isolated and washed with brine. The resulting organic layer was dried and concentrated in vacuo. The residue was purified by column chromatography (ethyl acetate:hexane=1:2) and give carbamic acid 1-(2-chloro-phenyl)-2-[1,2,3]triazol-2-yl-ethyl ester.

$^1$H-NMR (CDCl$_3$) δ7.62 (s, 1H), 7.21-7.38 (m, 4H), 6.55 (m, 1H), 5.09 (br, 2H), 4.8 (m, 2H)

EXAMPLE 2

Carbamic acid 1-(4-methoxy-phenyl)-2-[1,2,3]triazol-2-yl-ethyl ester

The procedure given in Example 1 was followed using 2-bromo-4'methoxyacetophenone as a reactant, instead of 2-bromo-2'-chloroacetophenone, to give carbamic acid 1-(4-methoxy-phenyl)-2-[1,2,3]triazol-2-yl-ethyl ester.

$^1$H-NMR (Acetone-d$_6$) δ7.65 (s, 2H), 7.35 (d, 2H), 6.92 (d, 2H), 6.15 (m, 1H), 5.75-6.1 (br, 2H), 4.7 (m, 2H), 3.81 (s, 3H)

EXAMPLE 3

Carbamic acid 1-phenyl-2-[1,2,3]triazol-2-yl-ethyl ester

The procedure given in Example 1 was followed using 2-bromo acetophenone as a reactant, instead of 2-bromo-2'-chloroacetophenone, to give carbamic acid 1-phenyl-2-[1,2,3]triazol-2-yl-ethyl ester.

$^1$H-NMR (CDCl$_3$) δ7.62(s, 1H), 7.37(br, 5H), 6.21(m, 1H), 4.98(br, 2H), 4.8(m, 2H)

EXAMPLE 4

Carbamic acid 1-(3-chloro-phenyl)-2-[1,2,3]triazol-2-yl-ethyl ester

The procedure given in Example 1 was followed using 2-bromo-3'-chloroacetophenone as a reactant, instead of 2-bromo-2'-chloroacetophenone, to give carbamic acid 1-(3-chloro-phenyl)-2-[1,2,3]triazol-2-yl-ethyl ester $^1$H-NMR (Acetone-d$_6$) δ7.67(s, 2H), 7.6-7.2(m, 4H), 6.25 (m, 1H), 6.15(br, 2H), 4.81(m, 2H)

EXAMPLE 5

Carbamic acid 1-(4-nitro-phenyl)-2-[1,2,3]triazol-2-yl-ethyl ester

The procedure given in Example 1 was followed using 2-bromo-4'-nitroacetophenone as a reactant, instead of 2-bromo-2'-chloroacetophenone, to give carbamic acid 1-(4-nitro-phenyl)-2-[1,2,3]triazol-2-yl-ethyl ester.

$^1$H-NMR (DMSO-d$_6$) δ8.15(s, 2H), 7.5 (m, 4H), 6.19 (m, 3H), 4.6-4.95 (m, 2H)

EXAMPLE 6

Carbamic acid 1-(4-fluoro-phenyl)-2-[1,2,3]triazol-2-yl-ethyl ester

The procedure given in Example 1 was followed using 2-bromo-4'-fluoroacetophenone as a reactant, instead of 2-bromo-2'-chloroacetophenone, to give carbamic acid 1-(4-fluoro-phenyl)-2-[1,2,3]triazol-2-yl-ethyl ester.

$^1$H-NMR (Acetone-d$_6$) δ7.66(s, 2H), 7.2-7.5(m, 4H), 6.3 (m, 1H), 5.8-6.6(br, 2H), 4.7(m, 2H)

EXAMPLE 7

Carbamic acid 1-m-tolyl-2-[1,2,3]triazol-2-yl-ethyl ester

The procedure given in Example 1 was followed using 2-bromo-3'-methylacetophenone as a reactant, instead of 2-bromo-2'-chloroacetophenone, to give carbamic acid 1-m-tolyl-2-[1,2,3]triazol-2-yl-ethyl ester.

$^1$H-NMR (Acetone-d$_6$) δ7.67(s, 2H), 7.1-7.35(m, 4H), 6.2 (m, 1H), 5.7-6.3(br, 2H), 4.7(m, 2H)

EXAMPLE 8

Carbamic acid 1-(3,4-dichloro-phenyl)-2-[1,2,3]triazol-2-yl-ethyl ester

The procedure given in Example 1 was followed using 2-bromo-3',4'-dichloroacetophenone as a reactant, instead of 2-bromo-2'-chloroacetophenone, to give carbamic acid 1-(3,4-dichloro-phenyl)-2-[1,2,3]triazol-2-yl-ethyl ester.

$^1$H-NMR (Acetone-d$_6$) δ7.67(s, 2H), 7.57(m, 2H), 7.36(m, 1H), 6.19(m, 1H), 5.9-6.3(br, 2H), 4.8-4.9(m, 2H)

EXAMPLE 9

Carbamic acid 2-[1,2,3]triazol-2-yl-1-(3-trifluoromethyl-phenyl)-ethyl ester

The procedure given in Example 1 was followed using 2-bromo-3'-(trifluoromethyl)acetophenone as a reactant, instead of 2-bromo-2'-chloroacetophenone, to give carbamic acid 2-[1,2,3]triazol-2-yl-1-(3-trifluoromethyl-phenyl)-ethyl ester.

$^1$H-NMR (Acetone-d$_6$) δ7.67 (m, 6H), 6.30(m, 1H), 5.9-6.4(br, 2H), 4.87(m, 2H)

EXAMPLE 10

Carbamic acid 1-(2,4-dichloro-phenyl)-2-[1,2,3]triazol-2-yl-ethyl ester

The procedure given in Example 1 was followed using 2-bromo-2',4'-dichloroacetophenone as a reactant, instead of 2-bromo-2'-chloroacetophenone, to give carbamic acid 1-(2,4-dichloro-phenyl)-2-[1,2,3]triazol-2-yl-ethyl ester.

$^1$H-NMR (Acetone-d$_6$) δ7.68(s, 2H), 7.5(m, 3H), 6.50(m, 1H), 5.9-6.4(br, 2H), 4.8(m, 2H)

EXAMPLE 11

Carbamic acid 2-[1,2,3]triazol-2-yl-1-(4-trifluoromethyl-phenyl)-ethyl ester

The procedure given in Example 1 was followed using 2-bromo-4'-(trifluoromethyl)acetophenone as a reactant, instead of 2-bromo-2'-chloroacetophenone, to give carbamic acid 2-[1,2,3]triazol-2-yl-1-(3-trifluoromethyl-phenyl)-ethyl ester.

$^1$H-NMR (Acetone-d$_6$) δ7.72 (m, 6H), 6.29(m, 1H), 5.8-6.8(br, 2H), 4.8(m, 2H)

EXAMPLE 12

Carbamic acid 2-[1,2,3]triazol-2-yl-1-(2-trifluoromethyl-phenyl)-ethyl ester

The procedure given in Example 1 was followed using 2-bromo-2'-(trifluoromethyl)acetophenone as a reactant, instead of 2-bromo-2'-chloroacetophenone, to give carbamic acid 2-[1,2,3]triazol-2-yl-1-(2-trifluoromethyl-phenyl)-ethyl ester.

$^1$H-NMR (Acetone-d$_6$) δ7.7 (m, 6H), 6.64(m, 1H), 5.7-6.4 (br, 2H), 4.75(m, 2H)

EXAMPLE 13

Carbamic acid 1-(2-chloro-phenyl)-3-[1,2,3]triazol-2-yl-propyl ester

The procedure given in Example 1 was followed using methanesulfonic acid 3-(2-chloro-phenyl)-3-hydroxy-propyl ester as a reactant, instead of 2-bromo-2'-chloroacetophenone, to give carbamic acid 1-(2-chloro-phenyl)-3-[1,2,3]triazol-2-yl-propyl ester without carbonyl reduction.

$^1$H-NMR (Acetone-d$_6$) δ7.87 (d, 2H), 8-7(m, 4H), 6.27(br, 2H), 6.00(m, 1H), 4.64(m, 2H), 2.4(m, 2H)

EXAMPLE 14

Carbamic acid 1-(3-chloro-phenyl)-2-[1,2,3]triazol-2-yl-propyl ester

The procedure given in Example 1 was followed using 2-Bromo-1-(3-chloro-phenyl)-propan-1-one as a reactant, instead of 2-bromo-2'-chloroacetophenone, to give carbamic acid 1-(3-chloro-phenyl)-2-[1,2,3]triazol-2-yl-propyl ester.

$^1$H-NMR (Acetone-d$_6$) δ8.09(s, 1H), 7.68(s, 1H), 7.3(m, 4H), 5.9-6.6(br, 2H), 6.07(m, 1H), 5.2 (m, 1H), 1.57(d, 3H)

EXAMPLE 15

Methyl-carbamic acid 1-(3-chloro-phenyl)-2-[1,2,3]triazol-2-yl-propyl ester

The procedure given in Example 14 was followed using excess methylamine as a reactant, instead of excess ammonium hydroxide, to give methyl-carbamic acid 1-(3-chloro-phenyl)-2-[1,2,3]triazol-2-yl-propyl ester.

$^1$H-NMR (Acetone-d6) δ8.06(s, 1H), 7.65(s, 1H), 7.3(m, 4H), 6.5(br, 1H), 6.05(m, 1H), 5.2 (m, 1H), 2.66(m, 3H), 1.54(d, 3H)

EXAMPLE 16

Carbamic acid 1-(2,5-dichloro-phenyl)-2-[1,2,3]triazol-2-yl-ethyl ester

The procedure given in Example 1 was followed using 2-bromo-2',5'-dichloroacetophenone as a reactant, instead of 2-bromo-2'-chloroacetophenone, to give carbamic acid 1-(2,5-dichloro-phenyl)-2-[1,2,3]triazol-2-yl-ethyl ester.

$^1$H-NMR (Acetone-d6) δ7.69(s, 2H), 7.46(m, 3H), 6.35(m, 1H), 5.9-6.58(br, 2H), 4.84(m, 2H)

EXAMPLE 17

Carbamic acid 1-(2,6-dichloro-phenyl)-2-[1,2,3]triazol-2-yl-ethyl ester

The procedure given in Example 1 was followed using 2-bromo-2',6'-dichloroacetophenone as a reactant, instead of 2-bromo-2'-chloroacetophenone, to give carbamic acid 1-(2,6-dichloro-phenyl)-2-[1,2,3]triazol-2-yl-ethyl ester.

$^1$H-NMR (Acetone-d6) δ7.68(s, 2H), 7.37-7.6(m, 3H), 6.9 (m, 1H), 5.8-6.25(br, 2H), 4.96(m, 2H)

EXAMPLE 18

Carbamic acid 1-(4-chloro-3-trifluoromethyl-phenyl)-2-[1,2,3]triazol-2-yl-ethyl ester The procedure given in Example 1 was followed using 2-bromo-4'-chloro-3'-(trifluoromethyl)acetophenone as a reactant, instead of 2-bromo-2'-chloroacetophenone, to give carbamic acid 1-(4-chloro-3-trifluoromethyl-phenyl)-2-[1,2,3]triazol-2-yl-ethyl ester.

$^1$H-NMR (Acetone-d6) δ7.9-7.6 (m, 5H), 6.26(m, 1H), 6.2(br, 2H), 4.88(m, 2H)

EXAMPLE 19

Carbamic acid 1-(2,4-dimethyl-phenyl)-2-[1,2,3]triazol-2-yl-ethyl ester

The procedure given in Example 1 was followed using 2-bromo-2',4'-dimethylacetophenone as a reactant, instead of 2-bromo-2'-chloroacetophenone, to give carbamic acid 1-(2,4-dimethyl-phenyl)-2-[1,2,3]triazol-2-yl-ethyl ester.

$^1$H-NMR (Acetone-d$_6$) δ7.93(s, 1H), 7.63(s, 1H), 7.46 (d, 1H), 7.1(m, 2H), 5.35(br, 2H), 5.0(m, 1H), 4.55(m, 2H), 2.33(s, 3H), 2.30(s, 3H)

EXAMPLE 20

4-(3,4-Dichloro-benzyl)-piperidine-1-carboxylic acid 1-(2-chloro-phenyl)-2-[1,2,3]triazol-2-yl-ethyl ester The procedure given in Example 1 was followed using excess 4-(3,4-dichloro-benzyl)-piperidine as a reactant, instead of excess ammonium hydroxide, to give 4-(3,4-dichloro-benzyl)-piperidine-1-carboxylic acid 1-(2-chloro-phenyl)-2-[1,2,3]triazol-2-yl-ethyl ester.

$^1$H-NMR (Acetone-d6) δ7.9(s, 2H), 7.48(m, 3H), 7.36(s, 1H), 7.22(d, 2H), 7.02(s, 1H), 4.07(d, 2H), 3.15(t, 2H), 2.68 (d, 2H), 1.76(m, 4H), 1.33(m, 4H)

EXAMPLE 21

Carbamic acid 1-(2-chloro-phenyl)-2-[1,2,3]triazol-1-yl-ethyl ester

To a solution of 2-bromo-2'-chloroacetophenone (2 mmol) and sodium carbonate (4 mmol) in toluene (100 ml), 1H-1,2,3-triazole (4 mmol) was added. The reaction was refluxed for 4 h and then cooled to 250 C. This solution was then concentrated on a rotary evaporator and diluted with ethyl acetate. This mixture was washed with brine. The resulting organic layer was dried and concentrated in vacuo. The crude product was dissolved in methanol (50 ml) and was added with sodium borohydride (8 mmol) slowly at 0oC to give alcohol compound represented by the general formula (XII) where in, G is 2-chlorophenyl, m is 0, Y is hydrogen, n is 0 and A is 1N-1,2,3-triazole. After 1 h stirring at room temperature, this solution was concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 4 h, followed by the addition of excess ammonium hydroxide (50 ml). After 4 h stirring at room temperature, the organic layer was isolated and washed with brine. The resulting organic layer was dried and concentrated in vacuo.

The preparation procedure of 1N-azole is same as that of 2N-azole in example 1 except the ratio of mobile phase of column chromatography. 1N-Azole is more polar than 2N-azole in chromatographic condition and separated by eluting with an increasing ratio of ethyl acetate in hexane after elution of 2N-azole to give carbamic acid 1-(2-chloro-phenyl)-2-[1,2,3]triazol-1-yl-ethyl ester.

$^1$H-NMR (CDCl3) δ7.57(s, 1H), 7.53(s, 1H), 7.05-7.35(m, 4H), 6.20(m, 1H), 5.64(br, 2H), 4.66(m, 2H)

EXAMPLE 22

Carbamic acid 1-(2,6-dichloro-phenyl)-2-[1,2,3]triazol-1-yl-ethyl ester

The procedure given in Example 21 was followed using 2-bromo-2',6'-dichloroacetophenone as a reactant, instead of 2-bromo-2'-chloroacetophenone, to give carbamic acid 1-(2,6-dichloro-phenyl)-2-[1,2,3]triazol-1-yl-ethyl ester.

$^1$H-NMR (Acetone-d$_6$) δ8.05(s, 1H), 7.69(s, 1H), 7.40-7.89(m, 3H), 6.97(m, 1H), 5.82-6.64(br, 2H), 5.58-5.52 (m, 2H)

EXAMPLE 23

Carbamic acid 1-(4-chloro-3-trifluoromethyl-phenyl)-2-[1,2,3]triazol-1-yl-ethyl ester The procedure given in Example 21 was followed using 2-bromo-4'-chloro-3'-(trifluoromethyl)acetophenone as a reactant, instead of 2-bromo-2'-chloroacetophenone, to give carbamic acid 1-(4-chloro-3-trifluoromethyl-phenyl)-2-[1,2,3]triazol-1-yl-ethyl ester.

$^1$H-NMR (Acetone-d$_6$) δ7.99 (d, 1H), 7.81(s, 1H), 7.68-7.65(m, 3H), 6.20(m, 3H), 4.93(dd, 2H)

EXAMPLE 24

Carbamic acid 1-(2-chloro-phenyl)-2-tetrazol-2-yl-ethyl ester

To a solution of 2-bromo-2'-chloroacetophenone (2 mmol) and sodium carbonate (4 mmol) in toluene (100 ml), 1H-tetrazole (4 mmol) was added. The reaction was refluxed for 4 h and then cooled to 25° C. This solution was then concentrated on a rotary evaporator and diluted with ethyl acetate. This mixture was washed with brine. The resulting organic layer was dried and concentrated in vacuo. The crude product was dissolved in methanol (50 ml) and was added with sodium borohydride (8 mmol) slowly at 0° C. to give alcohol compound represented by the general formula (XII) where in, G is 2-chlorophenyl, m is 0, Y is hydrogen, n is 0 and A is 2N-tetrazole. After 1 h stirring at room temperature, this solution was concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 4 h, followed by the addition of excess ammonium hydroxide (50 ml). After 4 h stirring at room temperature, the organic layer was isolated and washed with brine. The resulting organic layer was dried and concentrated in vacuo. The residue was purified by column chromatography (ethyl acetate:hexane=1:2) and give carbamic acid 1-(2-chloro-phenyl)-2-tetrazol-2-yl-ethyl ester.

$^1$H-NMR (Acetone-$d_6$) δ8.71 (s, 1H), 7.32-7.51 (m, 4H), 6.56 (m, 1H), 6.18 (br, 2H), 5.09 (m, 2H)

EXAMPLE 25

Carbamic acid 1-(4-methoxy-phenyl)-2-tetrazol-2-yl-ethyl ester

The procedure given in Example 24 was followed using 2-bromo-4'-methoxyacetophenone as a reactant, instead of 2-bromo-2'-chloroacetophenone, to give carbamic acid 1-(4-methoxy-phenyl)-2-tetrazol-2-yl-ethyl ester.

$^1$H-NMR (Acetone-$d_6$) δ8.45 (s, 1H), 7.30 (d, 2H), 6.90 (d, 2H), 6.18 (m, 1H), 4.18-5.19 (m, 4H), 3.83 (s, 3H)

EXAMPLE 26

Carbamic acid 1-phenyl-2-tetrazol-2-yl-ethyl ester

The procedure given in Example 24 was followed using 2-bromo acetophenone as a reactant, instead of 2-bromo-2'-chloroacetophenone, to give carbamic acid 1-phenyl-2-tetrazol-2-yl-ethyl ester.

$^1$H-NMR (Acetone-$d_6$) δ8.55 (s, 1H), 7.41 (s, 5H), 6.15 (m, 1H), 4.9-5.1 (m, 2H), 4.7-4.95 (br, 2H)

EXAMPLE 27

Carbamic acid 1-(4-chloro-phenyl)-2-tetrazol-2-yl-ethyl ester

The procedure given in Example 24 was followed using 2-bromo-4'-chloroacetophenone as a reactant, instead of 2-bromo-2'-chloroacetophenone, to give carbamic acid 1-(4-chloro-phenyl)-2-tetrazol-2-yl-ethyl ester.

$^1$H-NMR (Acetone-$d_6$) δ8.73 (s, 1H), 7.47 (m, 4H), 6.3 (m, 1H), 5.8-6.3 (br, 2H), 5.13 (m, 2H)

EXAMPLE 28

Carbamic acid 2-tetrazol-2-yl-1-p-tolyl-ethyl ester

The procedure given in Example 24 was followed using 2-bromo-4'-methylacetophenone as a reactant, instead of 2-bromo-2'-chloroacetophenone, to give carbamic acid 2-tetrazol-2-yl-1-p-tolyl-ethyl ester.

$^1$H-NMR (Acetone-$d_6$) δ8.54(s, 1H), 7.15-7.4(m, 4H), 6.19(m, 1H), 4.95( )m, 2H), 4.6-5.2(br, 2H), 2.38(s, 3H)

EXAMPLE 29

Carbamic acid 1-(4-nitro-phenyl)-2-tetrazol-2-yl-ethyl ester

The procedure given in Example 24 was followed using 2-bromo-4'-nitroacetophenone as a reactant, instead of 2-bromo-2'-chloroacetophenone, to give carbamic acid 1-(4-nitro-phenyl)-2-tetrazol-2-yl-ethyl ester.

$^1$H-NMR (Acetone-$d_6$) δ8.77(s, 1H), 8.3(m, 2H), 7.75(m, 2H), 6.4(m, 1H), 6.0-6.6(br, 2H), 5.23(m, 2H)

EXAMPLE 30

Carbamic acid 1-(4-fluoro-phenyl)-2-tetrazol-2-yl-ethyl ester

The procedure given in Example 24 was followed using 2-bromo-4'-fluoroacetophenone as a reactant, instead of 2-bromo-2'-chloroacetophenone, to give carbamic acid 1-(4-fluoro-phenyl)-2-tetrazol-2-yl-ethyl ester.

$^1$H-NMR (Acetone-$d_6$) δ8.72(s, 1H), 7.51(m, 2H), 7.22(m, 2H), 6.35(m, 1H), 5.8-6.4(br, 2H), 5.13(m, 2H)

EXAMPLE 31

Carbamic acid 1-(3-chloro-phenyl)-2-tetrazol-2-yl-ethyl ester

The procedure given in Example 24 was followed using 2-bromo-3'-chloroacetophenone as a reactant, instead of 2-bromo-2'-chloroacetophenone, to give carbamic acid 1-(3-chloro-phenyl)-2-tetrazol-2-yl-ethyl ester.

$^1$H-NMR (Acetone-$d_6$) δ8.47(s, 1H), 7.12-7.38(m, 4H), 6.15(m, 1H), 5.2-5.4(br, 2H), 4.9(m, 2H)

EXAMPLE 32

Carbamic acid 2-tetrazol-2-yl-1-m-tolyl-ethyl ester

The procedure given in Example 24 was followed using 2-bromo-3'-methylacetophenone as a reactant, instead of 2-bromo-2'-chloroacetophenone, to give carbamic acid 2-tetrazol-2-yl-1-m-tolyl-ethyl ester.

$^1$H-NMR (Acetone-$d_6$) δ8.50(s, 1H), 7.16-7.29(m, 4H), 6.18(m, 1H), 4.8-5.2(br, 2H), 4.90(m, 2H)

EXAMPLE 33

Carbamic acid 2-tetrazol-2-yl-1-o-tolyl-ethyl ester

The procedure given in Example 24 was followed using 2-bromo 2'-methylacetophenone as a reactant, instead of 2-bromo-2'-chloroacetophenone, to give carbamic acid 2-tetrazol-2-yl-1-o-tolyl-ethyl ester.

$^1$H-NMR (CDCl$_3$) δ8.55(s, 1H), 7.25-7.43(m, 4H), 7.05 (br, 2H), 6.66(m, 1H), 5.25(m, 2H)

EXAMPLE 34

Carbamic acid 1-(3,4-dichloro-phenyl)-2-tetrazol-2-yl-ethyl ester

The procedure given in Example 24 was followed using 2-bromo-3',4'-dichloroacetophenone as a reactant, instead of 2-bromo-2'-chloroacetophenone, to give carbamic acid 1-(3,4-dichloro-phenyl)-2-tetrazol-2-yl-ethyl ester.

¹H-NMR (Acetone-d₆) δ8.78(s, 1H), 7.38-7.68(m, 3H), 6.25(m, 1H), 5.89-6.62(br, 2H), 5.18(m, 2H)

EXAMPLE 35

Carbamic acid 2-tetrazol-2-yl-1-(3-trifluoromethyl-phenyl)-ethyl ester

The procedure given in Example 24 was followed using 2-bromo-3'-trifluoromethylacetophenone as a reactant, instead of 2-bromo-2'-chloroacetophenone, to give carbamic acid 2-tetrazol-2-yl-1-(3-trifluoromethyl-phenyl)-ethyl ester.

¹H-NMR (Acetone-d₆) δ8.78(s, 1H), 7.58-7.80(m, 4H), 6.38(m, 1H), 5.78-6.52(br, 2H), 5.20(m, 2H)

EXAMPLE 36

Carbamic acid 1-(2,4-dichloro-phenyl)-2-tetrazol-2-yl-ethyl ester

The procedure given in Example 24 was followed using 2-bromo 2',4'-dichloroacetophenone as a reactant, instead of 2-bromo-2'-chloroacetophenone, to give carbamic acid 1-(2, 4-dichloro-phenyl)-2-tetrazol-2-yl-ethyl ester.

¹H-NMR (Acetone-d₆) δ8.74(s, 1H), 7.5(m, 3H), 6.53(m, 1H), 5.9-6.5(br, 2H), 5.12(m, 2H)

EXAMPLE 37

Carbamic acid 2-tetrazol-2-yl-1-(4-trifluoromethyl-phenyl)-ethyl ester

The procedure given in Example 24 was followed using 2-bromo-4'-trifluoromethylacetophenone as a reactant, instead of 2-bromo-2'-chloroacetophenone, to give carbamic acid 2-tetrazol-2-yl-1-(4-trifluoromethyl-phenyl)-ethyl ester.

¹H-NMR (Acetone-d₆) δ8.69(s, 1H), 7.20-7.49(m, 4H), 6.36(m, 1H), 5.90-6.5(br, 2H), 4.95(m, 2H)

EXAMPLE 38

Carbamic acid 1-phenyl-3-tetrazol-2-yl-propyl ester

The procedure given in Example 24 was followed using 3-chloropropiophenone as a reactant, instead of 2-bromo-2'-chloroacetophenone, to give carbamic acid 1-phenyl-3-tetrazol-2-yl-propyl ester.

¹H-NMR (Acetone-d₆) δ8.73(s, 1H), 7.44-7.31(m, 5H), 6.66(br, 2H), 5.75(q, 1H), 4.80(m, 2H), 2.55(m, 2H)

EXAMPLE 39

Carbamic acid 1-(4-hydroxy-phenyl)-2-tetrazol-2-yl-ethyl ester

The procedure given in Example 24 was followed using 2-bromo-4'-hydroxyacetophenone as a reactant, instead of 2-bromo-2'-chloroacetophenone, to give carbamic acid 1-(4-hydroxy-phenyl)-2-tetrazol-2-yl-ethyl ester.

¹H-NMR (Acetone-d₆) δ9.04(s, 1H), 7.28(m, 2H), 6.87(m, 2H), 5.92(m, 1H), 5.65-6.25(br, 2H), 4.74(m, 2H), 3.05(br, 1H)

EXAMPLE 40

Carbamic acid 1-(2-chloro-phenyl)-3-tetrazol-2-yl-propyl ester

The procedure given in Example 24 was followed using methanesulfonic acid 3-(2-chloro-phenyl)-3-hydroxy-propyl ester as a reactant, instead of 2-bromo-2'-chloroacetophenone, to give carbamic acid 1-(2-chloro-phenyl)-3-tetrazol-2-yl-propyl ester without carbonyl reduction.

¹H-NMR (Acetone-d₆) δ8.74(s, 1H), 7.56-7.30(m, 4H), 6.20(br, 2H), 6.00(m, 1H), 4.93(m, 2H), 2.55(m, 2H)

EXAMPLE 41

Carbamic acid 1-(3-chloro-phenyl)-2-tetrazol-2-yl-propyl ester

The procedure given in Example 24 was followed using 2-bromo-1-(3-chloro-phenyl)-propan-1-one as a reactant, instead of 2-bromo-2'-chloroacetophenone, to give carbamic acid 1-(3-chloro-phenyl)-2-tetrazol-2-yl-propyl ester.

¹H-NMR (Acetone-d₆) δ8.74(s, 1H), 7.4(m, 4H), 6.08(m, 1H), 5.6-6.2(br, 2H), 5.5 (m, 1H), 1.52(d, 3H)

EXAMPLE 42

Methyl-carbamic acid 1-(3-chloro-phenyl)-2-tetrazol-2-yl-propyl ester

The procedure given in Example 24 was followed using excess methylamine as a reactant, instead of excess ammonium hydroxide, to give methyl-carbamic acid 1-(3-chloro-phenyl)-2-tetrazol-2-yl-propyl ester.

¹H-NMR (Acetone-d₆) δ8.73(s, 1H), 7.45(m, 4H), 6.2(m, 1H), 5.8-6.1(br, 1H), 5.5 (m, 1H), 2.58(d, 3H), 1.52(d, 3H)

EXAMPLE 43

Carbamic acid 1-(4-chloro-phenyl)-2-tetrazol-2-yl-propyl ester

The procedure given in Example 24 was followed using 2-bromo-1-(4-chloro-phenyl)-propan-1-one as a reactant, instead of 2-bromo-2'-chloroacetophenone, to give carbamic acid 1-(4-chloro-phenyl)-2-tetrazol-2-yl-propyl ester.

¹H-NMR (Acetone-d₆) δ8.75(s, 1H), 7.45(m, 4H), 6.10(d, 1H), 6.08(br, 2H), 5.52(m, 1H), 1.51(d, 3H)

EXAMPLE 44

Methyl-carbamic acid 1-(4-chloro-phenyl)-2-tetrazol-2-yl-propyl ester

The procedure given in Example 43 was followed using excess methylamine as a reactant, instead of excess ammonium hydroxide, to give methyl-carbamic acid 1-(4-chloro-phenyl)-2-tetrazol-2-yl-propyl ester.

¹H-NMR (Acetone-d₆) δ8.76(s, 1H), 7.8-7(m, 4H), 6.35 (br, 1H), 6.12(d, 1H), 5.51(m, 1H), 2.58(d, 3H), 1.50(d, 3H)

EXAMPLE 45

Carbamic acid 1-(3,4-dichloro-phenyl)-2-tetrazol-2-yl-propyl ester

The procedure given in Example 24 was followed using 2-Bromo-1-(3,4-dichloro-phenyl)-propan-1-one as a reactant, instead of 2-bromo-2'-chloroacetophenone, to give carbamic acid 1-(3,4-dichloro-phenyl)-2-tetrazol-2-yl-propyl ester.

¹H-NMR (Acetone-d₆) δ8.75(s, 1H), 7.8-7.2(m, 3H), 6.12 (d, 1H), 6.1(br, 2H), 5.57(m, 1H), 1.57(d, 3H)

EXAMPLE 46

Methyl-carbamic acid 1-(3,4-dichloro-phenyl)-2-tetrazol-2-yl-propyl ester

The procedure given in Example 45 was followed using excess methylamine as a reactant, instead of excess ammonium hydroxide, to give methyl-carbamic acid 1-(3,4-dichloro-phenyl)-2-tetrazol-2-yl-propyl ester.

¹H-NMR (Acetone-d₆) δ8.74(s, 1H), 7.8-7.2(m, 3H), 6.35 (br, 1H), 6.12(d, 1H), 5.55(m, 1H), 2.60(d, 3H), 1.55(d, 3H)

EXAMPLE 47

Carbamic acid 1-(3,4-dimethoxy-phenyl)-2-tetrazol-2-yl-ethyl ester

The procedure given in Example 24 was followed using 2-bromo-3',4'-dimethoxyacetophenone as a reactant, instead of 2-bromo-2'-chloroacetophenone, to give carbamic acid 1-(3,4-dimethoxy-phenyl)-2-tetrazol-2-yl-ethyl ester.

¹H-NMR (Acetone-d₆) δ8.04(s, 1H), 7.35-8.15(m, 3H), 6.7(m, 1H), 6.2(br, 2H), 4.92(m, 2H), 1.35(m, 6H)

EXAMPLE 48

Carbamic acid 1-(2,5-dichloro-phenyl)-2-tetrazol-2-yl-ethyl ester

The procedure given in Example 24 was followed using 2-bromo-2',5'-dichloroacetophenone as a reactant, instead of 2-bromo-2'-chloroacetophenone, to give carbamic acid 1-(2,5-dichloro-phenyl)-2-tetrazol-2-yl-ethyl ester.

¹H-NMR (Acetone-d₆) δ8.74(s, 1H), 7.25-7.63(m, 3H), 6.53(m, 1H), 5.8-6.57(br, 2H), 5.15(m, 2H)

EXAMPLE 49

Carbamic acid 1-(4-phenoxy-phenyl)-2-tetrazol-2-yl-ethyl ester

The procedure given in Example 24 was followed using 2-bromo-4'-phenoxyacetophenone as a reactant, instead of 2-bromo-2'-chloroacetophenone, to give carbamic acid 1-(4-phenoxy-phenyl)-2-tetrazol-2-yl-ethyl ester.

¹H-NMR (Acetone-d₆) δ8.73(s, 1H), 7.49(m, 4H), 6.95-7.25(m, 5H), 6.26(m, 1H), 5.8-6.39(br, 2H), 5.12(m, 2H)

EXAMPLE 50

Carbamic acid 1-(2,6-dichloro-phenyl)-2-tetrazol-2-yl-ethyl ester

The procedure given in Example 24 was followed using 2-bromo-2',6'-dichloroacetophenone as a reactant, instead of 2-bromo-2'-chloroacetophenone, to give carbamic acid 1-(2,6-dichloro-phenyl)-2-tetrazol-2-yl-ethyl ester.

¹H-NMR (Acetone-d₆) δ7.99(s, 2H), 7.2-7.7(m, 3H), 6.95 (m, 1H), 5.8-6.4(br, 2H), 4.86(m, 2H)

EXAMPLE 51

Carbamic acid 1-naphthalen-2-yl-2-tetrazol-2-yl-ethyl ester

The procedure given in Example 24 was followed using 2-bromo-2'-acetonaphtone as a reactant, instead of 2-bromo-2'-chloroacetophenone, to give carbamic acid 1-naphthalen-2-yl-2-tetrazol-2-yl-ethyl ester.

¹H-NMR (Acetone-d₆) δ8.75(s, 1H), 7.91-7.98(m, 4H), 7.52-7.65(m, 3H), 6.47(q, 1H), 6.19(br, 2H), 5.21(m, 2H).

EXAMPLE 52

Carbamic acid 2-tetrazol-2-yl-1-(2,3,4-trimethoxy-phenyl)-ethyl ester

The procedure given in Example 24 was followed using 2-bromo-2',3',4'-trimethoxyacetophenone as a reactant, instead of 2-bromo-2'-chloroacetophenone, to give carbamic acid 2-tetrazol-2-yl-1-(2,3,4-trimethoxy-phenyl)-ethyl ester.

¹H-NMR (Acetone-d₆) δ8.70(s, 1H), 7.03(d, 1H), 6.83(d, 1H), 6.41(m, 1H), 6.00(br, 2H), 5.07(m, 2H), 3.99(s, 3H), 3.87(s, 3H), 3.84(s, 3H)

EXAMPLE 53

Carbamic acid 2-tetrazol-2-yl-1-(3,4,5-trimethoxy-phenyl)-ethyl ester

The procedure given in Example 24 was followed using 2-bromo-3',4',5'-trimethoxyacetophenone as a reactant, instead of 2-bromo-2'-chloroacetophenone, to give carbamic acid 2-tetrazol-2-yl-1-(3,4,5-trimethoxy-phenyl)-ethyl ester ¹H-NMR (Acetone-d₆) δ8.73(s, 1H), 6.79(s, 2H), 6.21(m, 1H), 6.07(br, 2H), 5.03(m, 2H), 3.85(s, 6H), 3.74(s, 3H)

EXAMPLE 54

Carbamic acid 1-benzo[1,3]dioxol-5-yl-2-tetrazol-2-yl-ethyl ester

The procedure given in Example 24 was followed using 1-bBenzo[1,3]dioxol-5-yl-2-bromo-ethanone as a reactant, instead of 2-bromo-2'-chloroacetophenone, to give carbamic acid 1-benzo[1,3]dioxol-5-yl-2-tetrazol-2-yl-ethyl ester.

¹H-NMR (Acetone-d₆) δ8.72(s, 1H), 6.99-6.86(m, 3H), 6.18(m, 1H), 6.12(br, 2H), 6.04(s, 2H), 5.09(m, 2H)

EXAMPLE 55

Carbamic acid 1-(4-dimethylamino-phenyl)-2-tetrazol-2-yl-ethyl ester

The procedure given in Example 24 was followed using 2-bromo-4'-(dimethylamino) acetophenone as a reactant, instead of 2-bromo-2'-chloroacetophenone, to give carbamic acid 1-(4-dimethylamino-phenyl)-2-tetrazol-2-yl-ethyl ester.
$^1$H-NMR (Acetone-d$_6$) δ8.86(s, 1H), 6.78-7.34(m, 4H), 6.12(m, 1H), 5.7-6.25(br, 2H), 5.02(m, 2H), 1.35 (s, 6H)

EXAMPLE 56

Carbamic acid 2-tetrazol-2-yl-1-(2,4,6-trimethyl-phenyl)-ethyl ester

The procedure given in Example 24 was followed using 2-bromo-2',4',6'-trimethylacetophenone as a reactant, instead of 2-bromo-2'-chloroacetophenone, to give carbamic acid 2-tetrazol-2-yl-1-(2,4,6-trimethyl-phenyl)-ethyl ester.
$^1$H-NMR (Acetone-d$_6$) δ8.79(s, 1H), 7.56(s, 2H), 6.25(m, 1H), 5.66-6.39(br, 2H), 5.04(m, 2H), 1.36(s, 9H)

EXAMPLE 57

Carbamic acid 1-(4-tert-butyl-phenyl)-2-tetrazol-2-yl-ethyl ester

The procedure given in Example 24 was followed using 2-bromo-4'-tert-butylacetophenone as a reactant, instead of 2-bromo-2'-chloroacetophenone, to give carbamic acid 1-(4-tert-butyl-phenyl)-2-tetrazol-2-yl-ethyl ester.
$^1$H-NMR (Acetone-d$_6$) δ9.07(s, 1H), 7.44(m, 4H), 6.25(m, 1H), 5.75-6.2(br, 2H), 4.96(m, 2H), 1.33(s, 9H)

EXAMPLE 58

Carbamic acid 1-indan-5-yl-2-tetrazol-2-yl-ethyl ester

The procedure given in Example 24 was followed using 2-bromo-1-indan-5-yl-ethanone as a reactant, instead of 2-bromo-2'-chloroacetophenone, to give carbamic acid 1-indan-5-yl-2-tetrazol-2-yl-ethyl ester.
$^1$H-NMR (Acetone-d$_6$) δ8.72(s, 1H), 7.31-7.22(m, 3H), 6.21(t, 1H), 6.01(br, 2H), 5.06(m, 2H), 2.17-1.75(m, 6H)

EXAMPLE 59

Carbamic acid 1-(3,4-difluoro-phenyl)-2-tetrazol-2-yl-ethyl ester

The procedure given in Example 24 was followed using 2-bromo-3',4'-difluoroacetophenone as a reactant, instead of 2-bromo-2'-chloroacetophenone, to give carbamic acid 1-(3,4-difluoro-phenyl)-2-tetrazol-2-yl-ethyl ester.
$^1$H-NMR (Acetone-d$_6$) δ8.78(s, 1H), 7.46(m, 3H), 5.50-6.34(br, 3H), 5.13(m, 2H)

EXAMPLE 60

Carbamic acid 1-(2-fluoro-phenyl)-2-tetrazol-2-yl-ethyl ester

The procedure given in Example 24 was followed using 2-bromo-2'-fluoroacetophenone as a reactant, instead of 2-bromo-2'-chloroacetophenone, to give carbamic acid 1-(2-fluoro-phenyl)-2-tetrazol-2-yl-ethyl ester.
$^1$H-NMR (Acetone-d$_6$) δ8.74(s, 1H), 7.44(m, 4H), 5.60-5.81(m, 1H), 5.13(br, 2H), 4.97(m, 2H)

EXAMPLE 61

4-Benzyl-piperidine-1-carboxylic acid 1-(2-chloro-phenyl)-2-tetrazol-2-yl-ethyl ester The procedure given in Example 24 was followed using excess 4-benzyl piperidine as a reactant, instead of excess ammonium hydroxide, to give 4-benzyl-piperidine-1-carboxylic acid 1-(2-chloro-phenyl)-2-tetrazol-2-yl-ethyl ester.
$^1$H-NMR (CDCl$_3$) δ7.86(s, 1H), 7.08-7.34(m, 9H), 4.1(m, 2H), 2.97(m, 2H), 2.6(m, 2H), 1.77(m, 4H), 1.267(m, 4H)

EXAMPLE 62

4-Phenyl-piperazine-1-carboxylic acid 1-(2-chloro-phenyl)-2-tetrazol-2-yl-ethyl ester The procedure given in Example 24 was followed using excess 4-phenyl piperazine as a reactant, instead of excess ammonium hydroxide, to give 4-phenyl-piperazine-1-carboxylic acid 1-(2-chloro-phenyl)-2-tetrazol-2-yl-ethyl ester.
$^1$H-NMR (Acetone-d$_6$) δ8.77(s, 1H), 7.54-6.82(m, 9H), 6.63(t, 1H), 5.19(d, 2H), 3.73-2.89(d, 8H)

EXAMPLE 63

4-(4-Fluoro-benzoyl)-piperidine-1-carboxylic acid 1-(2-chloro-phenyl)-2-tetrazol-2-yl-ethyl ester The procedure given in Example 24 was followed using excess 4-(4-fluoro-benzoyl)-piperidine as a reactant, instead of excess ammonium hydroxide, to give 4-(4-fluoro-benzoyl)-piperidine-1-carboxylic acid 1-(2-chloro-phenyl)-2-tetrazol-2-yl-ethyl ester.
$^1$H-NMR (Acetone-d$_6$) δ8.75(s, 1H), 8.18-7.30(m, 8H), 6.61(t, 1H), 5.19(d, 2H), 4.29(m, 1H), 4.03(m, 2H), 3.68(m, 1H) 2.01-1.18(m, 5H)

EXAMPLE 64

1-Benzyl-4-[1-(2-chloro-phenyl)-2-tetrazol-2-yl-ethoxycarbonyl]-piperazin-1-ium The procedure given in Example 24 was followed using excess 4-benzyl-piperazine as a reactant, instead of excess ammonium hydroxide, to give 4-Benzyl-piperazine-1-carboxylic acid 1-(2-chloro-phenyl)-2-tetrazol-2-yl-ethyl ester. This compound was dissolved in methylene chloride and added HCl gas to give 1-benzyl-4-[1-(2-chloro-phenyl)-2-tetrazol-2-yl-ethoxycarbonyl]-piperazin-1-ium.
$^1$H-NMR (CDCl$_3$) δ8.50(s, 1H), 7.6-7.2(m, 9H), 6.58(m, 1H), 5.087(d, 2H), 2.47(m, 4H), 1.73(m, 6H)

EXAMPLE 65

4-Benzyl-piperidine-1-carboxylic acid 1-phenyl-2-tetrazol-2-yl-ethyl ester

The procedure given in Example 26 was followed using excess 4-benzyl piperidine as a reactant, instead of excess ammonium hydroxide, to give 4-benzyl-piperidine-1-carboxylic acid 1-phenyl-2-tetrazol-2-yl-ethyl ester.

¹H-NMR (Acetone-d₆) δ8.74(s, 1H), 7.47-7.20(m, 12H), 6.26(m, 1H), 5.14(m, 2H), 4.07(m, 1H), 2.55(m, 2H), 1.70(m, 3H), 1.10(m, 3H)

EXAMPLE 66

Carbamic acid 1-(2,4-difluoro-phenyl)-2-tetrazol-2-yl-ethyl ester

The procedure given in Example 24 was followed using 2-bromo-2',4'-difluoroacetophenone as a reactant, instead of 2-bromo-2'-chloroacetophenone, to give carbamic acid 1-(2,4-difluoro-phenyl)-2-tetrazol-2-yl-ethyl ester.
¹H-NMR (Acetone-d₆) δ9.13(s, 1H), 7.5(s, 1H), 7.05(m, 2H), 5.6-6.2(br, 2H), 5.45(m, 1H), 4.82(m, 2H)

EXAMPLE 67

[2-(3,4-Dihydroxy-phenyl)-ethyl]-carbamic acid 1-(2-chloro-phenyl)-2-tetrazol-2-yl-ethyl ester The procedure given in Example 24 was followed using excess 2-(3,4-dihydroxy-phenyl)-ethyl amine as a reactant, instead of excess ammonium hydroxide, to give [2-(3,4-dihydroxy-phenyl)-ethyl]-carbamic acid 1-(2-chloro-phenyl)-2-tetrazol-2-yl-ethyl ester.
¹H-NMR (Acetone-d₆) δ8.76(s, 1H), 7.50-6.60(m, 7H), 6.50(t, 1H), 5.09(d, 2H), 3.23(m, 2H), 2.60(t, 2H)

EXAMPLE 68

4-(4-Methoxy-benzyl)-piperidine-1-carboxylic acid 1-(2-chloro-phenyl)-2-tetrazol-2-yl-ethyl ester The procedure given in Example 24 was followed using excess 4-(4-methoxy-benzyl)-piperidine as a reactant, instead of excess ammonium hydroxide, to give 4-(4-methoxy-benzyl)-piperidine-1-carboxylic acid 1-(2-chloro-phenyl)-2-tetrazol-2-yl-ethyl ester.
¹H-NMR (Acetone-d₆) δ7.96(s, 1H), 7.41(m, 1H), 7.17(m, 3H), 7.08(m, 1H), 6.92(m, 3H), 4.08(d, 2H), 3.82(s, 3H), 3.08(t, 2H), 2.57(d, 2H), 1.75(m, 4H), 1.37(m, 4H)

EXAMPLE 69

4-(3,4-Dichloro-benzyl)-piperidine-1-carboxylic acid 1-(2-chloro-phenyl)-2-tetrazol-2-yl-ethyl ester The procedure given in Example 24 was followed using excess 4-(3,4-dichloro-benzyl)-piperidine as a reactant, instead of excess ammonium hydroxide, to give 4-(3,4-dichloro-benzyl)-piperidine-1-carboxylic acid 1-(2-chloro-phenyl)-2-tetrazol-2-yl-ethyl ester.
¹H-NMR (Acetone-d₆) δ7.91(s, 1H), 7.51(m, 3H), 7.36(s, 1H), 7.25(m, 2H), 7.02(s, 1H), 4.05(d, 2H), 3.09(t, 2H), 2.65(d, 2H), 1.75(m, 4H), 1.35(m, 4H)

EXAMPLE 70

4-Pyridin-4-ylmethyl-piperidine-1-carboxylic acid 1-(2-chloro-phenyl)-2-tetrazol-2-yl-ethyl ester The procedure given in Example 24 was followed using excess 4-pyridin-4-ylmethyl-piperidine as a reactant, instead of excess ammonium hydroxide, to 4-pyridin-4-ylmethyl-piperidine-1-carboxylic acid 1-(2-chloro-phenyl)-2-tetrazol-2-yl-ethyl ester.
¹H-NMR (Acetone-d₆) δ8.50 (d, 2H), 7.91(s, 1H), 7.26(m, 6H), 4.05(d, 2H), 3.09(t, 2H), 2.66(d, 2H), 1.75(m, 4H), 1.36(m, 4H)

EXAMPLE 71

4-(4-Fluoro-benzyl)-piperidine-1-carboxylic acid 1-(2-chloro-phenyl)-2-tetrazol-2-yl-ethyl ester The procedure given in Example 24 was followed using excess 4-(4-fluoro-benzyl)-piperidine as a reactant, instead of excess ammonium hydroxide, to give 4-(4-fluoro-benzyl)-piperidine-1-carboxylic acid 1-(2-chloro-phenyl)-2-tetrazol-2-yl-ethyl ester.
¹H-NMR (Acetone-d₆) δ7.91(s, 1H), 7.37(s, 1H), 7.28(m, 6H), 7.02(s, 1H), 4.06(d, 2H), 3.06(t, 2H), 2.62(d, 2H), 1.75(m, 4H), 1.35(m, 4H)

EXAMPLE 72

3-(4-Fluoro-benzyl)-piperidine-1-carboxylic acid 1-(2-chloro-phenyl)-2-tetrazol-2-yl-ethyl ester The procedure given in Example 24 was followed using excess 3-(4-fluoro-benzyl)-piperidine as a reactant, instead of excess ammonium hydroxide, to give 3-(4-fluoro-benzyl)-piperidine-1-carboxylic acid 1-(2-chloro-phenyl)-2-tetrazol-2-yl-ethyl ester.
¹H-NMR (Acetone-d₆) δ7.88(s, 1H), 6.99-7.32 (m, 8H), 3.95(d, 2H), 3.06(t, 1H), 2.95(t, 1H), 2.61(d, 2H), 1.75(m, 2H), 1.31(m, 6H)

EXAMPLE 73

4-(4-Chloro-benzyl)-piperidine-1-carboxylic acid 1-(2-chloro-phenyl)-2-tetrazol-2-yl-ethyl ester The procedure given in Example 24 was followed using excess 4-(4-chloro-benzyl)-piperidine as a reactant, instead of excess ammonium hydroxide, to give 4-(4-chloro-benzyl)-piperidine-1-carboxylic acid 1-(2-chloro-phenyl)-2-tetrazol-2-yl-ethyl ester.
¹H-NMR (Acetone-d₆) δ7.92(s, 1H), 7.31 (m, 6H), 7.04(s, 2H), 4.05(d, 2H), 3.06(t, 2H), 2.61(d, 2H), 1.75(m, 4H), 1.33(m, 4H)

EXAMPLE 74

3-(4-Chloro-phenyl)-pyrrolidine-1-carboxylic acid 1-(2-chloro-phenyl)-2-tetrazol-2-yl-ethyl ester The procedure given in Example 24 was followed using excess 3-(4-chloro-phenyl)-pyrrolidine as a reactant, instead of excess ammonium hydroxide, to give 3-(4-chloro-phenyl)-pyrrolidine-1-carboxylic acid 1-(2-chloro-phenyl)-2-tetrazol-2-yl-ethyl ester.
¹H-NMR (Acetone-d₆) δ8.09(s, 1H), 7.56(s, 1H), 7.42(m, 6H), 7.01(s, 1H), 4.05(t, 1H), 3.84(d, 2H), 3.68(m, 6H), 2.4 (m, 1H)

EXAMPLE 75

3-Phenethyl-pyrrolidine-1-carboxylic acid 1-(2-chloro-phenyl)-2-tetrazol-2-yl-ethyl ester The procedure given in Example 24 was followed using excess 3-phenethyl-pyrrolidine as a reactant, instead of excess ammonium hydroxide, to give 3-phenethyl-pyrrolidine-1-carboxylic acid 1-(2-chloro-phenyl)-2-tetrazol-2-yl-ethyl ester.
$^1$H-NMR (Acetone-$d_6$) δ8.06(s, 1H), 7.51(s, 1H), 7.24(m, 7H), 7.01(s, 1H), 3.86(t, 1H), 3.68(d, 2H), 2.71(t, 2H), 2.25 (m, 3H), 1.82(m, 6H)

EXAMPLE 76

4-[1,2,3]Triazol-2-ylmethyl-piperidine-1-carboxylic acid 1-(2-chloro-phenyl)-2-tetrazol-2-yl-ethyl ester The procedure given in Example 24 was followed using excess 4-[1,2,3]triazol-2-ylmethyl-piperidine as a reactant, instead of excess ammonium hydroxide, to give 4-[1,2,3]triazol-2-ylmethyl-piperidine-1-carboxylic acid 1-(2-chloro-phenyl)-2-tetrazol-2-yl-ethyl ester.
$^1$H-NMR (Acetone-$d_6$) δ7.92(s, 1H), 7.71(s, 2H), 7.37(s, 2H), 7.03(s, 2H), 4.42(d, 2H), 4.05(d, 2H), 3.15(t, 2H), 1.75 (m, 4H), 1.33(m, 4H)

EXAMPLE 77

3-Tetrazol-2-ylmethyl-piperidine-1-carboxylic acid 1-(2-chloro-phenyl)-2-tetrazol-2-yl-ethyl ester The procedure given in Example 24 was followed using excess 3-tetrazol-2-ylmethyl-piperidine as a reactant, instead of excess ammonium hydroxide, to give 3-tetrazol-2-ylmethyl-piperidine-1-carboxylic acid 1-(2-chloro-phenyl)-2-tetrazol-2-yl-ethyl ester.
$^1$H-NMR (Acetone-$d_6$) δ8.78(s, 1H), 7.91(s, 1H), 7.35(s, 2H), 7.01(s, 2H), 4.79(d, 2H), 3.97(d, 2H), 3.15(m, 2H), 1.82(m, 2H), 1.4(m, 6H)

EXAMPLE 78

3-[1,2,3]Triazol-2-ylmethyl-piperidine-1-carboxylic acid 1-(2-chloro-phenyl)-2-tetrazol-2-yl-ethyl ester The procedure given in Example 24 was followed using excess 3-[1,2,3]triazol-2-ylmethyl-piperidine as a reactant, instead of excess ammonium hydroxide, to give 3-[1,2,3]triazol-2-ylmethyl-piperidine-1-carboxylic acid 1-(2-chloro-phenyl)-2-tetrazol-2-yl-ethyl ester.
$^1$H-NMR (Acetone-$d_6$) δ7.89(s, 1H), 7.70(s, 2H), 7.30(s, 2H), 7.0(s, 2H), 4.45(d, 2H), 3.9(d, 2H), 3.15(m, 2H), 1.85(m, 2H), 1.3(m, 6H)

EXAMPLE 79

4-Benzoyl-piperidine-1-carboxylic acid 1-(2-chloro-phenyl)-2-tetrazol-2-yl-ethyl ester The procedure given in Example 24 was followed using excess 4-benzoyl-piperidine as a reactant, instead of excess ammonium hydroxide, to give 4-benzoyl-piperidine-1-carboxylic acid 1-(2-chloro-phenyl)-2-tetrazol-2-yl-ethyl ester.
$^1$H-NMR (Acetone-$d_6$) δ8.1 (m, 2H), 7.95(s, 1H), 7.63(m, 3H), 7.42(s, 2H), 7.0(s, 2H), 4.11(d, 2H), 3.85(m, 1H), 3.38(t, 2H), 2.09(m, 2H), 2.06(m, 2H), 1.83(m, 4H)

EXAMPLE 80

4-(4-Chloro-benzoyl)-piperidine-1-carboxylic acid 1-(2-chloro-phenyl)-2-tetrazol-2-yl-ethyl ester The procedure given in Example 24 was followed using excess 4-(4-chloro-benzoyl)-piperidine as a reactant, instead of excess ammonium hydroxide, to give 4-(4-chloro-benzoyl)-piperidine-1-carboxylic acid 1-(2-chloro-phenyl)-2-tetrazol-2-yl-ethyl ester.
$^1$H-NMR (Acetone-$d_6$) δ8.11 (m, 2H), 7.95(s, 1H), 7.59 (m, 2H), 7.41(s, 2H), 7.03(s, 2H), 4.11(d, 2H), 3.85(m, 1H), 3.38(t, 2H), 2.09(m, 2H), 2.07(m, 2H), 1.83(m, 4H)

EXAMPLE 81

4-(4-Methoxy-benzoyl)-piperidine-1-carboxylic acid 1-(2-chloro-phenyl)-2-tetrazol-2-yl-ethyl ester The procedure given in Example 24 was followed using excess 4-(4-methoxy-benzoyl)-piperidine as a reactant, instead of excess ammonium hydroxide, to give 4-(4-methoxy-benzoyl)-piperidine-1-carboxylic acid 1-(2-chloro-phenyl)-2-tetrazol-2-yl-ethyl ester.
$^1$H-NMR (Acetone-$d_6$) δ8.06(m, 2H), 7.95(s, 1H), 7.41(m, 2H), 7.05(d, 4H), 4.15(d, 2H), 3.92(s, 3H), 3.87(m, 1H), 3.35(t, 2H), 203(m, 2H), 1.98(m, 2H), 1.81(m, 4H)

EXAMPLE 82

4-[1,2,3]Triazol-1-ylmethyl-piperidine-1-carboxylic acid 1-(2-chloro-phenyl)-2-tetrazol-2-yl-ethyl ester The procedure given in Example 24 was followed using excess. 4-[1,2,3]triazol-1-ylmethyl-piperidine as a reactant, instead of excess ammonium hydroxide, to give 4-[1,2,3]triazol-1-ylmethyl-piperidine-1-carboxylic acid 1-(2-chloro-phenyl)-2-tetrazol-2-yl-ethyl ester.
$^1$H-NMR (Acetone-$d_6$) δ8.0(s, 2H), 7.96(s, 1H), 7.71(s, 2H), 7.39(s, 1H), 7.05(s, 1H), 4.05(d, 2H), 3.89(m, 1H), 3.15(t, 2H), 2.23(m, 2H), 1.99(m, 2H), 1.86(m, 4H)

EXAMPLE 83

4-Tetrazol-2-ylmethyl-piperidine-1-carboxylic acid 1-(2-chloro-phenyl)-2-tetrazol-2-yl-ethyl ester The procedure given in Example 24 was followed using excess 4-tetrazol-2-ylmethyl-piperidine as a reactant, instead of excess ammonium hydroxide, to give 4-tetrazol-2-ylmethyl-piperidine-1-carboxylic acid 1-(2-chloro-phenyl)-2-tetrazol-2-yl-ethyl ester.
$^1$H-NMR (Acetone-$d_6$) δ7.97(s, 1H), 7.7(s, 1H), 7.42(s, 2H), 7.09(s, 2H), 4.96(d, 2H), 4.15(d, 2H), 3.18(t, 2H), 2.17 (m, 2H), 2.14(m, 2H), 1.97(m, 4H)

EXAMPLE 84

4-[1,2,3]Triazol-2-yl-piperidine-1-carboxylic acid 1-(2-chloro-phenyl)-2-tetrazol-2-yl-ethyl ester The procedure given in Example 24 was followed using excess 4-[1,2,3]triazol-2-yl-piperidine as a reactant, instead of excess ammonium hydroxide, to give 4-[1,2,3]triazol-2-yl-piperidine-1-carboxylic acid 1-(2-chloro-phenyl)-2-tetrazol-2-yl-ethyl ester.
$^1$H-NMR (Acetone-$d_6$) δ7.99(s, 1H), 7.73(s, 2H), 7.45(s, 2H), 7.05(s, 2H), 4.15(d, 2H), 3.17(t, 2H), 2.14(m, 4H), 2.04 (m, 4H)

EXAMPLE 85

4-(3,4-Dichloro-benzyl)-piperidine-1-carboxylic acid 1-(2,5-dichloro-phenyl)-2-tetrazol-2-yl-ethyl ester The procedure given in Example 48 was followed using excess 4-(3,4-dichloro-benzyl)-piperidine as a reactant, instead of excess ammonium hydroxide, to give 4-(3,4-dichloro-benzyl)-piperidine-1-carboxylic acid 1-(2,5-dichloro-phenyl)-2-tetrazol-2-yl-ethyl ester.

$^1$H-NMR (Acetone-$d_6$) δ7.9(s, 1H), 7.47(d, 2H), 7.37(s, 1H), 7.23(d, 2H), 7.02(s, 1H), 4.05(d, 2H), 3.05(t, 2H), 2.65 (d, 2H), 1.75(m, 4H), 1.35(m, 4H)

EXAMPLE 86

4-(5-Phenyl-tetrazol-2-yl)-piperidine-1-carboxylic acid 1-(2-chloro-phenyl)-2-tetrazol-2-yl-ethyl ester The procedure given in Example 24 was followed using excess 4-(5-phenyl-tetrazol-2-yl)-piperidine as a reactant, instead of excess ammonium hydroxide, to give 4-(5-phenyl-tetrazol-2-yl)-piperidine-1-carboxylic acid 1-(2-chloro-phenyl)-2-tetrazol-2-yl-ethyl ester.

$^1$H-NMR (Acetone-$d_6$) δ8.18 (m, 2H), 8.1(s, 1H), 7.57(m, 6H), 7.07(s, 1H), 5.3(m, 1H), 4.25(d, 2H), 3.56(t, 1H), 2.45 (m, 6H), 1.31(m, 2H)

EXAMPLE 87

4-[1,2,3]Triazol-1-yl-piperidine-1-carboxylic acid 1-(2-chloro-phenyl)-2-tetrazol-2-yl-ethyl ester The procedure given in Example 24 was followed using excess 4-[1,2,3]triazol-1-yl-piperidine as a reactant, instead of excess ammonium hydroxide, to give 4-[1,2,3]triazol-1-yl-piperidine-1-carboxylic acid 1-(2-chloro-phenyl)-2-tetrazol-2-yl-ethyl ester.

$^1$H-NMR (Acetone-$d_6$) δ8.09(s, 1H), 7.98(s, 1H), 7.71(s, 1H), 7.45(s, 2H), 7.05(s, 2H), 4.98(m, 1H), 4.25(d, 2H), 3.4(t, 1H), 2.25(m, 6H), 1.31(m, 2H)

EXAMPLE 88

4-(3,4-Dichloro-benzyl)-piperidine-1-carboxylic id 1-(2,4-dichloro-phenyl)-2-tetrazol-2-yl-ethyl ester The procedure given in Example 36 was followed using excess 4-(3,4-dichloro-benzyl)-piperidine as a reactant, instead of excess ammonium hydroxide, to give 4-(3,4-dichloro-benzyl)-piperidine-1-carboxylic acid 1-(2,4-dichloro-phenyl)-2-tetrazol-2-yl-ethyl ester.

$^1$H-NMR (Acetone-$d_6$) δ7.9(s, 1H), 7.49(d, 2H), 7.35(s, 1H), 7.25d, 2H), 7.01(s, 1H), 4.06(d, 2H), 3.10(t, 2H), 2.65(d, 2H), 1.75(m, 4H), 1.35(m, 4H)

EXAMPLE 89

4-(3,4-Dichloro-benzyl)-piperidine-1-carboxylic acid 1-(3,4-dichloro-phenyl)-2-tetrazol-2-yl-ethyl ester The procedure given in Example 34 was followed using excess 4-(3,4-dichloro-benzyl)-piperidine as a reactant, instead of excess ammonium hydroxide, to give 4-(3,4-dichloro-benzyl)-piperidine-1-carboxylic acid 1-(3,4-dichloro-phenyl)-2-tetrazol-2-yl-ethyl ester.

$^1$H-NMR (Acetone-$d_6$) δ7.9(s, 1H), 7.49(d, 2H), 7.36(s, 1H), 7.26(d, 2H), 7.02(s, 1H), 4.10(d, 2H), 3.1(t, 2H), 2.65(d, 2H), 1.77(m, 4H), 1.35(m, 4H)

EXAMPLE 90

3-(4-Chloro-benzyl)-pyrrolidine-1-carboxylic acid 1-(2-chloro-phenyl)-2-tetrazol-2-yl-ethyl ester The procedure given in Example 24 was followed using excess 3-(4-chloro-benzyl)-pyrrolidine as a reactant, instead of excess ammonium hydroxide, to give 3-(4-chloro-benzyl)-pyrrolidine-1-carboxylic acid 1-(2-chloro-phenyl)-2-tetrazol-2-yl-ethyl ester.

$^1$H-NMR (Acetone-$d_6$) δ8.0(s, 1H), 7.50(s, 1H), 7.34(m, 6H), 6.99(s, 1H), 3.42(t, 1H), 2.84(d, 2H), 2.61(m, 3H), 2.09 (m, 6H)

EXAMPLE 91

4-(3,5-Bis-trifluoromethyl-benzyl)-piperidine-1-carboxylic acid 1-(2-chloro-phenyl)-2-tetrazol-2-yl-ethyl ester The procedure given in Example 24 was followed using excess 4-(3,5-bis-trifluoromethyl-benzyl)-piperidine as a reactant, instead of excess ammonium hydroxide, to give 4-(3,5-bis-trifluoromethyl-benzyl)-piperidine-1-carboxylic acid 1-(2-chloro-phenyl)-2-tetrazol-2-yl-ethyl ester.

$^1$H-NMR (Acetone-$d_6$) δ7.95(s, 1H), 7.90(m, 4H), 7.37(s, 2H), 7.02(s, 1H), 4.1(d, 2H), 3.1(t, 2H), 2.91(d, 2H), 1.77(m, 4H), 1.48(m, 4H)

EXAMPLE 92

4-(5-Methyl-tetrazol-2-ylmethyl)-piperidine-1-carboxylic acid 1-(2-chloro-phenyl)-2-tetrazol-2-yl-ethyl ester The procedure given in Example 24 was followed using excess 4-(5-methyl-tetrazol-2-ylmethyl)-piperidine as a reactant, instead of excess ammonium hydroxide, to give 4-(5-methyl-tetrazol-2-ylmethyl)-piperidine-1-carboxylic acid 1-(2-chloro-phenyl)-2-tetrazol-2-yl-ethyl ester.

$^1$H-NMR (Acetone-$d_6$) δ7.9(s, 1H), 7.37(s, 2H), 7.01(s, 2H), 4.6(d, 2H), 4.08(d, 2H), 3.14(t, 2H), 2.48(s, 3H), 1.73(m, 4H), 1.52(m, 4H)

EXAMPLE 93

3-Phenethyl-pyrrolidine-1-carboxylic acid 1-(2,5-dichloro-phenyl)-2-tetrazol-2-yl-ethyl ester The procedure given in Example 48 was followed using excess 3-phenethyl-pyrrolidine as a reactant, instead of excess ammonium hydroxide, to give 3-phenethyl-pyrrolidine-1-carboxylic acid 1-(2,5-dichloro-phenyl)-2-tetrazol-2-yl-ethyl ester.

$^1$H-NMR (Acetone-$d_6$) δ8.05(s, 1H), 7.52(s, 1H), 7.28(m, 6H), 7.00(s, 1H), 3.8(t, 1H), 3.34(d, 2H), 2.72(t, 2H), 2.15(m, 3H), 1.70(m, 6H)

EXAMPLE 94

3-Phenethyl-pyrrolidine-1-carboxylic acid 1-(2,4-dichloro-phenyl)-2-tetrazol-2-yl-ethyl ester The procedure given in Example 36 was followed using excess 3-phenethyl-pyrrolidine as a reactant, instead of excess ammonium hydroxide, to give 3-phenethyl-pyrrolidine-1-carboxylic acid 1-(2,4-dichloro-phenyl)-2-tetrazol-2-yl-ethyl ester.
$^1$H-NMR (Acetone-$d_6$) δ8.05(s, 1H), 7.51(s, 1H), 7.28(m, 6H), 7.01(s, 1H), 3.75(t, 1H), 3.34(d, 2H), 2.74(t, 2H), 2.20(m, 3H), 1.75(m, 6H)

EXAMPLE 95

3-Phenethyl-pyrrolidine-1-carboxylic acid 1-(3,4-dichloro-phenyl)-2-tetrazol-2-yl-ethyl ester The procedure given in Example 34 was followed using excess 3-phenethyl-pyrrolidine as a reactant, instead of excess ammonium hydroxide, to give 3-phenethyl-pyrrolidine-1-carboxylic acid 1-(3,4-dichloro-phenyl)-2-tetrazol-2-yl-ethyl ester.
$^1$H-NMR (Acetone-$d_6$) δ8.05(s, 1H), 7.51(s, 1H), 7.27(m, 6H), 7.00(s, 1H), 3.76(t, 1H), 3.35(d, 2H), 2.72(t, 2H), 2.20(m, 3H), 1.75(m, 6H)

EXAMPLE 96

3-[2-(4-Methoxy-phenyl)-ethyl]-pyrrolidine-1-carboxylic acid 1-(2-chloro-phenyl)-2-tetrazol-2-yl-ethyl ester The procedure given in Example 24 was followed using excess 3-[2-(4-methoxy-phenyl)-ethyl]-pyrrolidine as a reactant, instead of excess ammonium hydroxide, to give 3-[2-(4-methoxy-phenyl)-ethyl]-pyrrolidine-1-carboxylic acid 1-(2-chloro-phenyl)-2-tetrazol-2-yl-ethyl ester.
$^1$H-NMR (Acetone-$d_6$) δ8.05(s, 1H), 7.51(s, 2H), 7.17(m, 2H), 7.00(s, 2H), 6.86(m, 2H), 3.78(s, 3H), 3.67(d, 2H), 3.32(t, 1H), 2.65(t, 2H), 2.36(m, 3H), 1.71(m, 6H)

EXAMPLE 97

4-(3,4-Dichloro-benzyl)-piperidine-1-carboxylic acid 1-phenyl-2-tetrazol-2-yl-ethyl ester The procedure given in Example 26 was followed using excess 4-(3,4-dichloro-benzyl)-piperidine as a reactant, instead of excess ammonium hydroxide, to give 4-(3,4-dichloro-benzyl)-piperidine-1-carboxylic acid 1-phenyl-2-tetrazol-2-yl-ethyl ester.
$^1$H-NMR (Acetone-$d_6$) δ7.9(s, 1H), 7.48(m, 4H), 7.36(s, 1H), 7.24(m, 2H), 7.01(s, 1H), 4.07(d, 2H), 3.15(t, 2H), 2.66(d, 2H), 2.08(m, 2H), 1.77(m, 2H), 1.38(m, 4H)

EXAMPLE 98

Carbamic acid 1-(4-benzyloxy-phenyl)-2-tetrazol-2-yl-ethyl ester

The procedure given in Example 24 was followed using 2-bromo-4'-benzyloxyacetophenone as a reactant, instead of 2-bromo-2'-chloroacetophenone, to give carbamic acid 1-(4-benzyloxy-phenyl)-2-tetrazol-2-yl-ethyl ester.
$^1$H-NMR (Acetone-$d_6$) δ8.7(s, 1H), 7.46(m, 7H), 7.05(m, 2H), 6.23(m, 1H), 5.85-6.4(br, 2H), 5.16(s, 2H), 5.08(m, 2H)

EXAMPLE 99

Carbamic acid 1-(2-chloro-phenyl)-2-tetrazol-1-yl-ethyl ester

To a solution of 2-bromo-2'-chloroacetophenone (2 mmol) and sodium carbonate (4 mmol) in toluene (100 ml), 1H-tetrazole (4 mmol) was added. The reaction was refluxed for 4 h and then cooled to 25° C. This solution was then concentrated on a rotary evaporator and diluted with ethyl acetate. This mixture was washed with brine. The resulting organic layer was dried and concentrated in vacuo. The crude product was dissolved in methanol (50 ml) and was added with sodium borohydride (8 mmol) slowly at 0° C. to give alcohol compound represented by the general formula (XII) where in, G is 2-chlorophenyl, m is 0, Y is hydrogen, n is 0 and A is 1N-tetrazole. After 1 h stirring at room temperature, this solution was concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 4 h, followed by the addition of excess ammonium hydroxide (50 ml). After 4 h stirring at room temperature, the organic layer was isolated and washed with brine. The resulting organic layer was dried and concentrated in vacuo.

The preparation procedure of 1N-azole is same as that of 2N-azole in example except the ratio of mobile phase of column chromatography. 1N-Azole is more polar than 2N-azole in chromatographic condition and separated by eluting with an increasing ratio of ethyl acetate in hexane after elution of 2N-azole to give carbamic acid 1-(2-chloro-phenyl)-2-tetrazol-1-yl-ethyl ester
$^1$H-NMR (Acetone-$d_6$) δ9.13(s, 1H), 7.3-7.54(m, 4H), 6.41(m, 1H), 5.9-6.8(br, 2H), 5.01(m, 2H)

EXAMPLE 100

Carbamic acid 1-phenyl-3-tetrazol-1-yl-propyl ester

The procedure given in Example 99 was followed using 3-chloropropiophenone as a reactant, instead of 2-bromo-2'-chloroacetophenone, to give carbamic acid 1-phenyl-3-tetrazol-1-yl-propyl ester.
$^1$H-NMR (Acetone-$d_6$) δ9.13(s, 1H), 7.38-7.32(m, 5H), 6.08(br, 2H), 5.71(m, 1H), 4.63(m, 2H), 2.53(m, 2H)

EXAMPLE 101

Carbamic acid 1-(3-chloro-phenyl)-2-tetrazol-1-yl-propyl ester

The procedure given in Example 99 was followed using 2-bromo-1-(3-chloro-phenyl)-propan-1-one as a reactant, instead of 2-bromo-2'-chloroacetophenone, to give carbamic acid 1-(3-chloro-phenyl)-2-tetrazol-1-yl-propyl ester.

¹H-NMR (Acetone-d₆) δ9.1(s, 1H), 7.1-7.4(m, 4H), 5.95-6.5(br, 2H), 6.0(m, 1H), 5.3 (m, 1H), 1.65(d, 3H)

EXAMPLE 102

Carbamic acid 1-(4-chloro-phenyl)-2-tetrazol-1-yl-propyl ester

The procedure given in Example 99 was followed using 2-bromo-1-(4-chloro-phenyl)-propan-1-one as a reactant, instead of 2-bromo-2'-chloroacetophenone, to give carbamic acid 1-(4-chloro-phenyl)-2-tetrazol-1-yl-propyl ester.

¹H-NMR (Acetone-d₆) δ9.20 (d, 1H), 7.6-7(m, 4H), 6.4(br, 2H), 6.05(m, 1H), 5.35(m, 1H), 1.66(m, 3H)

EXAMPLE 103

Methyl-carbamic acid 1-(4-chloro-phenyl)-2-tetrazol-1-yl-propyl ester

The procedure given in Example 102 was followed using excess methylamine as a reactant, instead of excess ammonium hydroxide, to give methyl-carbamic acid 1-(4-chloro-phenyl)-2-tetrazol-1-yl-propyl ester.

¹H-NMR (Acetone-d₆) δ9.17 (d, 1H), 7.6-7(m, 4H), 6.72 (br, 1H), 6.07(m, 1H), 5.34(m, 1H), 2.67(m, 3H), 1.65(m, 3H)

EXAMPLE 104

Carbamic acid 1-(3,4-dichloro-phenyl)-2-tetrazol-1-propyl ester

The procedure given in Example 99 was followed using 2-bromo-1-(3,4-dichloro-phenyl)-propan-1-one as a reactant, instead of 2-bromo-2'-chloroacetophenone, to give carbamic acid 1-(3,4-dichloro-phenyl)-2-tetrazol-1-yl-propyl ester.

¹H-NMR (Acetone-d₆) δ9.12 (d, 1H), 7.7-7.1(m, 3H), 6.354(br, 2H), 6.03(m, 1H), 5.38(m, 1H), 1.7(m, 3H)

EXAMPLE 105

Carbamic acid 1-(2,5-dichloro-phenyl)-2-tetrazol-1-yl-ethyl ester

The procedure given in Example 99 was followed using 2-bromo-2',5'-dichloroacetophenone as a reactant, instead of 2-bromo-2'-chloroacetophenone, to give carbamic acid 1-(2,5-dichloro-phenyl)-2-tetrazol-1-yl-ethyl ester.

¹H-NMR (Acetone-d₆) δ9.17(s, 1H), 7.25-7.63(m, 3H), 6.37(m, 1H), 5.8-6.7(br, 2H), 5.03(m, 2H)

EXAMPLE 106

Carbamic acid 1-(4-phenoxy-phenyl)-2-tetrazol-1-yl-ethyl ester

The procedure given in Example 99 was followed using 2-bromo-4'-phenoxyacetophenone as a reactant, instead of 2-bromo-2'-chloroacetophenone, to give carbamic acid 1-(4-phenoxy-phenyl)-2-tetrazol-1-yl-ethyl ester.

¹H-NMR (Acetone-d₆) δ9.09(s, 1H), 7.42(m, 4H), 6.90-7.22(m, 5H), 6.14(m, 1H), 5.92-6.45(br, 2H), 4.97(m, 2H)

EXAMPLE 107

Carbamic acid 1-(2,4-dichloro-phenyl)-2-tetrazol-1-yl-ethyl ester

The procedure given in Example 99 was followed using 2-bromo-2',4'-dichloroacetophenone as a reactant, instead of 2-bromo-2'-chloroacetophenone, to give carbamic acid 1-(2,4-dichloro-phenyl)-2-tetrazol-1-yl-ethyl ester.

¹H-NMR (CDCl₃) δ9.16(s, 1H), 7.60(d, 1H), 7.39(dd, 1H), 7.26(m, 1H), 6.36(m, 3H), 5.02(m, 2H)

EXAMPLE 108

Carbamic acid 1-naphthalen-2-yl-2-tetrazol-1-yl-ethyl ester

The procedure given in Example 99 was followed using 2-bromo-2'-acetonaphtone as a reactant, instead of 2-bromo-2'-chloroacetophenone, to give carbamic acid 1-naphthalen-2-yl-2-tetrazol-1-yl-ethyl ester.

¹H-NMR (Acetone-d₆) δ9.10(s, 1H), 7.88-7.98(m, 4H), 7.53-7.58(m, 3H), 6.31(t, 1H), 6.28(br, 2H), 5.09(d, 2H)

EXAMPLE 109

Carbamic acid 2-tetrazol-1-yl-1-(2,3,4-trimethoxy-phenyl)-ethyl ester

The procedure given in Example 99 was followed using 2-bromo-2',3',4'-trimethoxyacetophenone as a reactant, instead of 2-bromo-2'-chloroacetophenone, to give carbamic acid 2-tetrazol-1-yl-1-(2,3,4-trimethoxy-phenyl)-ethyl ester.

¹H-NMR (Acetone-d₆) δ9.04(s, 1H), 6.87(d, 1H), 6.75(d, 1H), 6.25(t, 1H), 6.20(br, 2H), 4.90(d, 2H), 4.00(s, 3H), 3.85 (s, 3H), 3.84(s, 3H)

EXAMPLE 110

Carbamic acid 1-benzo[1,3]diozol-5-yl-2-tetrazol-1-yl-ethyl ester

The procedure given in Example 99 was followed using 1-benzo[1,3]dioxol-5-yl-2-bromo-ethanone as a reactant, instead of 2-bromo-2'-chloroacetophenone, to give carbamic acid 1-benzo[1,3]dioxol-5-yl-2-tetrazol-1-yl-ethyl ester ¹H-NMR (Acetone-d₆) δ9.06(s, 1H), 6.85-6.91(m, 3H), 6.17(br, 2H), 6.03(s, 2H), 6.02(m, 1H), 4.94(m, 2H)

EXAMPLE 111

Carbamic acid 2-tetrazol-1-yl-1-(2,4,6-trimethyl-phenyl)-ethyl ester

The procedure given in Example 99 was followed using 2-bromo-2',4',6'-trimethylacetophenone as a reactant, instead of 2-bromo-2'-chloroacetophenone, to give carbamic acid 2-tetrazol-1-yl-1-(2,4,6-trimethyl-phenyl)-ethyl ester.

¹H-NMR (Acetone-d₆) δ9.14(s, 1H), 7.59(s, 2H), 6.18(m, 1H), 5.65-6.40(br, 2H), 5.10(m, 2H), 1.35(s, 9H)

EXAMPLE 112

Carbamic acid 1-(4-tert-butyl-phenyl)-2-tetrazol-1-yl-ethyl ester

The procedure given in Example 99 was followed using 2-bromo-4'-tert-butylacetophenone as a reactant, instead of 2-bromo-2'-chloroacetophenone, to give carbamic acid 1-(4-tert-butyl-phenyl)-2-tetrazol-1-yl-ethyl ester.
$^1$H-NMR (Acetone-$d_6$) δ8.74(s, 1H), 7.46(m, 4H), 6.11(m, 1H), 5.80-6.2(br, 2H), 5.10(m, 2H), 1.34(s, 9H)

EXAMPLE 113

Carbamic acid 1-indan-5-yl-2-tetrazol-yl-ethyl ester

The procedure given in Example 99 was followed using 2-bromo-1-indan-5-yl-ethanone as a reactant, instead of 2-bromo-2'-chloroacetophenone, to give carbamic acid 1-indan-5-yl-2-tetrazol-1-yl-ethyl ester
$^1$H-NMR (Acetone-$d_6$) δ9.05(s, 1H), 7.25-7.16(m, 3H), 6.08(m, 3H), 4.95(m, 2H), 2.1-2.03(m, 6H)

EXAMPLE 114

Carbamic acid 1-phenyl-2-tetrazol-1-yl-ethyl ester

The procedure given in Example 99 was followed using 2-bromo acetophenone as a reactant, instead of 2-bromo-2'-chloroacetophenone, to give carbamic acid 1-phenyl-2-tetrazol-1-yl-ethyl ester.
$^1$H-NMR (Acetone-$d_6$) δ9.04(s, 1H), 7.44(m, 3H), 6.07(m, 1H), 5.57-6.45br, 2H), 5.03(m, 2H)

EXAMPLE 115

Carbamic acid 1-(3,4-difluoro-phenyl)-2-tetrazol-1-yl-ethyl ester

The procedure given in Example 99 was followed using 2-bromo-3',4'-difluoroacetophenone as a reactant, instead of 2-bromo-2'-chloroacetophenone, to give carbamic acid 1-(3,4-difluoro-phenyl)-2-tetrazol-1-yl-ethyl ester.
$^1$H-NMR (Acetone-$d_6$) δ9.04(s, 1H), 7.44(m, 3H), 5.57-6.45br, 3H), 5.03(m, 2H)

EXAMPLE 116

Carbamic acid 1-(2-fluoro-phenyl)-2-tetrazol-1-yl-ethyl ester

The procedure given in Example 99 was followed using 2-bromo-2'-fluoroacetophenone as a reactant, instead of 2-bromo-2'-chloroacetophenone, to give carbamic acid 1-(2-fluoro-phenyl)-2-tetrazol-1-yl-ethyl ester.
$^1$H-NMR (Acetone-$d_6$) δ9.14(s, 1H), 7.29(m, 4H), 5.6-6.17(br, 2H), 5.32(m, 1H), 4.84(m, 2H)

EXAMPLE 117

4-Phenyl-piperazine-1-carboxylic acid 1-(2-chloro-phenyl)-2-tetrazol-1-yl-ethyl ester The procedure given in Example 99 was followed using excess 4-phenyl-piperazine as a reactant, instead of excess ammonium hydroxide, to give 4-phenyl-piperazine-1-carboxylic acid 1-(2-chloro-phenyl)-2-tetrazol-1-yl-ethyl ester.
$^1$H-NMR (Acetone-$d_6$) δ9.24(s, 1H), 7.85-7.38(m, 9H), 6.54(t, 1H), 5.10(d, 2H), 4.28-3.55(d, 8H)

EXAMPLE 118

4-Benzyl-piperidine-1-carboxylic acid 1-phenyl-2-tetrazol-1-yl-ethyl ester

The procedure given in Example 114 was followed using excess 4-benzyl-piperidine as a reactant, instead of excess ammonium hydroxide, to give 4-benzyl-piperidine-1-carboxylic acid 1-phenyl-2-tetrazol-1-yl-ethyl ester.
$^1$H-NMR (Acetone-$d_6$) δ9.06(s, 1H), 7.45-7.20(m, 12H), 6.19(t, 1H), 5.01(d, 2H), 4.05(m, 1H), 2.55(m, 2H), 1.75(m, 3H), 1.10(m, 3H)

EXAMPLE 119

Carbamic acid 1-(2,4-difluoro-phenyl)-2-tetrazol-yl-ethyl ester

The procedure given in Example 99 was followed using 2-bromo-2',4'-difluoroacetophenone as a reactant, instead of 2-bromo-2'-chloroacetophenone, to give carbamic acid 1-(2,4-difluoro-phenyl)-2-tetrazol-1-yl-ethyl ester.
$^1$H-NMR (Acetone-$d_6$) δ9.12(s, 1H), 7.55(m, 1H), 7.05(m, 2H), 5.85(br, 2H), 5.41(m, 1H), 4.8(m, 2H)

EXAMPLE 120

[2-(3,4-Dihydroxy-phenyl)-ethyl]-carbamic acid 1-(2-chloro-phenyl)-2-tetrazol-1-yl-ethyl ester The procedure given in Example 99 was followed using excess 2-(3,4-dihydroxy-phenyl)-ethyl amine as a reactant, instead of excess ammonium hydroxide, to give [2-(3,4-dihydroxy-phenyl)-ethyl]-carbamic acid 1-(2-chloro-phenyl)-2-tetrazol-1-yl-ethyl ester.
$^1$H-NMR (Acetone-$d_6$) δ9.14(s, 1H), 7.50-6.56(m, 7H), 5.53(t, 1H), 5.07(d, 2H), 3.25(m, 2H), 2.57(m 2H)

EXAMPLE 121

Carbamic acid 1-(4-benzyloxy-phenyl)-2-tetrazol-1-yl-ethyl ester

The procedure given in Example 99 was followed using 2-bromo-4'-benzyloxyacetophenone as a reactant, instead of 2-bromo-2'-chloroacetophenone, to give carbamic acid 1-(4-benzyloxy-phenyl)-2-tetrazol-1-yl-ethyl ester.
$^1$H-NMR (Acetone-$d_6$) δ9.05(s, 1H), 7.42(m, 7H), 7.04(m, 2H), 6.09(m, 1H), 5.9-6.3(br, 2H), 5.15(s, 2H), 5.04(m, 2H)

EXAMPLE 122

4-(3,4-Dichloro-benzyl)-piperidine-1-carboxylic acid 1-(2-chloro-phenyl)-2-tetrazol-1-yl-ethyl ester The procedure given in Example 99 was followed using excess 4-(3,4-dichloro-benzyl)-piperidine as a reactant, instead of excess ammonium hydroxide, to give 4-(3,4-dichloro-benzyl)-piperidine-1-carboxylic acid 1-(2-chloro-phenyl)-2-tetrazol-1-yl-ethyl ester.
$^1$H-NMR (CDCl$_3$) δ7.92(s, 1H), 7.48(m, 3H), 7.37(s, 1H), 7.25(d, 2H), 7.03(s, 1H), 4.07(d, 2H), 3.08(t, 2H), 2.67(d, 2H), 1.75(m, 4H), 1.34(m, 4H)

EXAMPLE 123

Carbamic acid 1-(2-chloro-phenyl)-2-(5-methyl-tetrazol-2-yl)-ethyl ester

To a solution of 2-bromo-2'-chloroacetophenone (2 mmol) and sodium carbonate (4 mmol) in toluene (100 ml), 5-methyl-1H-tetrazole (4 mmol) was added. The reaction was refluxed for 7 h and then cooled to 25° C. This solution was then concentrated on a rotary evaporator and diluted with ethyl acetate. This mixture was washed with brine. The resulting organic layer was dried and concentrated in vacuo. The crude product was dissolved in methanol (50 ml) and was added with sodium borohydride (2.4 mmol) slowly at 0° C. to give alcohol compound represented by the general formula (XII) where in, G is 2-chlorophenyl, m is 0, Y is hydrogen, n is 0 and A is 2N-5-methyl tetrazole. After 2 h stirring at room temperature, this solution was concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 0.5 h, followed by the addition of excess ammonium hydroxide (50 ml). After 4 h stirring at room temperature, the organic layer was isolated and washed with brine. The resulting organic layer was dried and concentrated in vacuo. The residue was purified by column chromatography (ethyl acetate:hexane=1:2) and give carbamic acid 1-(2-chloro-phenyl)-2-(5-methyl-tetrazol-2-yl)-ethyl ester.

$^1$H-NMR (Acetone-$d_6$) δ7.37-7.61(m, 4H), 6.58(m, 1H), 6.15(br, 2H), 4.97(m, 2H), 2.47(s, 3H)

EXAMPLE 124

Carbamic acid 1-(2-chloro-phenyl)-2-(5-phenyl-tetrazol-2-yl-ethyl ester

The procedure given in Example 123 was followed using 5-phenyl-1H-tetrazole as a reactant, instead of 5-methyl-1H-tetrazole, to give carbamic acid 1-(2-chloro-phenyl)-2-(5-phenyl-tetrazol-2-yl)-ethyl ester.

$^1$H-NMR (Acetone-$d_6$) δ8.0-8.4 (m, 2H), 7.2-7.8(m, 7H), 6.67(t, 1H), 6.2(br, 2H), 5.14(d, 2H)

EXAMPLE 125

Methyl-carbamic acid 1-(2-chloro-phenyl)-2-(5-phenyl-tetrazol-2-yl)-ethyl ester

The procedure given in Example 124 was followed using excess methylamine as a reactant, instead of excess ammonium hydroxide, to give Methyl-carbamic acid 1-(2-chloro-phenyl)-2-(5-phenyl-tetrazol-2-yl)-ethyl ester.

$^1$H-NMR (Acetone-$d_6$) δ8.1-8.25 (m, 2H), 7.3-7.7(m, 7H), 6.7(t, 1H), 6.55(br, 1H), 5.12(d, 2H), 2.65(d, 3H)

EXAMPLE 126

Carbamic acid 1-(2-chloro-phenyl)-2-[5-(2,3-dichloro-phenyl)-tetrazol-2-yl]-ethyl ester The procedure given in Example 123 was followed using 5-(2,3-dichlorophenyl)-1H-tetrazole as a reactant, instead of 5-methyl-1H-tetrazole, to give carbamic acid 1-(2-chloro-phenyl)-2-[5-(2,3-dichloro-phenyl)-tetrazol-2-yl]-ethyl ester.

$^1$H-NMR (Acetone-$d_6$) δ7.38-7.85 (m, 7H), 6.63(t, 1H), 6.24(br, 2H), 5.21(d, 2H)

EXAMPLE 127

Methyl-carbamic acid 1-(2-chloro-phenyl)-2-[5-(2,3-dichloro-phenyl)-tetrazol-2-yl]-ethyl ester The procedure given in Example 126 was followed using excess methylamine as a reactant, instead of excess ammonium hydroxide, to give methyl-carbamic acid 1-(2-chloro-phenyl)-2-[5-(2,3-dichloro-phenyl)-tetrazol-2-yl]-ethyl ester.

$^1$H-NMR (Acetone-$d_6$) δ7.35-7.85 (m, 7H), 6.68(t, 1H), 6.57(d, 1H), 5.20(d, 2H), 2.68(d, 3H)

EXAMPLE 128

Carbamic acid 1-(2-chloro-phenyl)-2-(5-pyridin-2-yl-tetrazol-2-yl)-ethyl ester

The procedure given in Example 123 was followed using 5-pyridin-2-yl-1H-tetrazole as a reactant, instead of 5-methyl-1H-tetrazole, to give carbamic acid 1-(2-chloro-phenyl)-2-(5-pyridin-2-yl-tetrazol-2-yl)-ethyl ester.

$^1$H-NMR (Acetone-$d_6$) δ9.28(s, 1H), 8.75(m, 1H), 8.43(d, 1H), 7.62-7.40(m 5H), 6.64(m, 1H), 6.25(br, 2H), 5.18(d, 2H)

EXAMPLE 129

Ethyl-carbamic acid 1-(2-chloro-phenyl)-2-(5-pyridin-2-yl-tetrazol-2-yl)-ethyl ester The procedure given in Example 128 was followed using excess ethylamine as a reactant, instead of excess ammonium hydroxide, to give ethyl-carbamic acid 1-(2-chloro-phenyl)-2-(5-pyridin-2-yl-tetrazol-2-yl)-ethyl ester.

$^1$H-NMR (Acetone-$d_6$) δ9.28(s, 1H), 8.75(dd, 1H), 8.41 (m, 1H), 7.62-7.40(m, 5H), 6.66(t, 1H), 6.58(br, 1H), 5.17(d, 2H), 2.07(m, 3H)

EXAMPLE 130

Carbamic acid 2-(5-amino-tetrazol-2-yl)-1-(2-chloro-phenyl)-ethyl ester

The procedure given in Example 123 was followed using 5-amino-1H-tetrazole as a reactant, instead of s-methyl-1H-tetrazole, to give carbamic acid 2-(5-amino-tetrazol-2-yl)-1-(2-chloro-phenyl)-ethyl ester.

$^1$H-NMR (Acetone-$d_6$) δ7.20-7.76 (m, 4H), 6.5(m, 1H), 6.12(br, 2H), 5.46(br, 2H), 4.75(m, 2H)

EXAMPLE 131

Carbamic acid 1-(2-chloro-phenyl)-2-(5-methyl-tetrazol-1-yl)-ethyl ester

To a solution of 2-bromo-2'-chloroacetophenone (2 mmol) and sodium carbonate (4 mmol) in toluene (100 ml), 5-methyl-1H-tetrazole (4 mmol) was added. The reaction was refluxed for 7 h and then cooled to 25° C. This solution was then concentrated on a rotary evaporator and diluted with ethyl acetate. This mixture was washed with brine. The resulting organic layer was dried and concentrated in vacuo. The crude product was dissolved in methanol (50 ml) and was added with sodium borohydride (2.4 mmol) slowly at 0° C. to give alcohol compound represented by the general formula (XII) where in, G is 2-chlorophenyl, m is 0, Y is hydrogen, n is 0 and A is 1N-5-methyl tetrazole. After 2 h stirring at room temperature, this solution was concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 0.5 h, followed by the addition of excess ammonium hydroxide (50 ml). After 4 h stirring at room temperature, the organic layer was isolated and washed with brine. The resulting organic layer was dried and concentrated in vacuo.

The preparation procedure of 1N-azole is same as that of 2N-azole in example except the ratio of mobile phase of column chromatography. 1N-Azole is more polar than 2N-azole in chromatographic condition and separated by eluting with an increasing ratio of ethyl acetate in hexane after elution of 2N-azole to give carbamic acid 1-(2-chloro-phenyl)-2-(5-methyl-tetrazol-1-yl)-ethyl ester $^1$H-NMR (Acetone-d$_6$) δ7.35-7.59 (m, 4H), 6.44(m, 1H), 5.99-6.4(br, 2H), 4.82(m, 2H), 2.537(s, 3H)

EXAMPLE 132

Carbamic acid 1-(2-chloro-phenyl)-2-[5-(2,3-dichloro-phenyl)-tetrazol-1-yl]-ethyl ester The procedure given in Example 131 was followed using 5-(2,3-dichlorophenyl)-1H-tetrazole as a reactant, instead of s-methyl-1H-tetrazole, to give carbamic acid 1-(2-chloro-phenyl)-2-[5-(2,3-dichloro-phenyl)-tetrazol-1-yl]-ethyl ester.

$^1$H-NMR (Acetone-d$_6$) δ7.37-7.95 (m, 7H), 6.26(t, 1H), 6.20(br, 2H), 4.79(d, 2H)

EXAMPLE 133

Methyl-carbamic acid 1-(2-chloro-phenyl)-2-[5-(2,3-dichloro-phenyl)-tetrazol-1-yl]-ethyl ester The procedure given in Example 132 was followed using excess methylamine as a reactant, instead of excess ammonium hydroxide, to give methyl-carbamic acid 1-(2-chloro-phenyl)-2-[5-(2,3-dichloro-phenyl)-tetrazol-1-yl]-ethyl ester.

$^1$H-NMR (Acetone-d$_6$) δ7.36-7.94 (m, 7H), 6.47(br, 1H), 6.29(t, 1H), 4.79(d, 2H), 2.65(d, 3H)

EXAMPLE 134

Carbamic acid (R)-(+)-1-(2-chloro-phenyl)-2-tetrazol-2-yl-ethyl ester

To a solution of 1H-tetrazole (2.4 mmol) and lithium carbonate (4.8 mmol) in DMF (100 ml), (R)-2-chlorostyrene oxide (2 mmol) was slowly added to give enantiomerically (R)-configured alcohol compound represented by the general formula (XII) where in, G is 2-chlorophenyl, m is 0, Y is hydrogen, n is 0 and A is 2N-tetrazole. The reaction was stirred for 4 h at 120° C. and then cooled to 25° C. This solution was then concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 3 h, followed by the addition of excess ammonium hydroxide (50 ml). After 5 h stirring at room temperature, the organic layer was isolated and washed with brine. The resulting organic layer was dried and concentrated in vacuo. The residue was purified by column chromatography (ethyl acetate:hexane=1:2) and recrystallized from dichloromethane and ethyl ether (1:1) to give carbamic acid (R)-1-(2-chloro-phenyl)-2-tetrazol-2-yl-ethyl ester.

Optical purity was more than 98% ee. The optical purity was measured by HPLC (Chiracel OD-H column, Mobile phase=acetonitrile+water with 0.1% trifluoroacetic acid).

$[α]_D$=+16.0°

$^1$H-NMR (Acetone-d$_6$) δ8.74(s, 1H), 7.38-7.54(m, 4H), 6.59(m, 1H), 6.16(br, 2H), 5.09(m, 2H)

EXAMPLE 135

Carbamic acid (S)-(−)-1-(2-chloro-phenyl)-2-tetrazol-2-yl-ethyl ester

The procedure given in Example 134 was followed using (S)-2-chlorostyrene oxide as a reactant, instead of (R)-2-chlorostyrene oxide, to give Carbamic acid (S)-1-(2-chloro-phenyl)-2-tetrazol-2-yl-ethyl ester.

$^1$H-NMR (Acetone-d$_6$) δ8.74(s, 1H), 7.39-7.52(m, 4H), 6.57(m, 1H), 6.18(br, 2H), 5.11(m, 2H)

EXAMPLE 136

Carbamic acid (S)-1-(4-chloro-phenyl)-2-tetrazol-2-yl-ethyl ester

The procedure given in Example 134 was followed using (S)-4-chlorostyrene oxide as a reactant, instead of (R)-2-chlorostyrene oxide, to give Carbamic acid (S)-1-(4-chloro-phenyl)-2-tetrazol-2-yl-ethyl ester.

$^1$H-NMR (CDCl$_3$) δ8.54(s, 1H), 7.29-7.41(m, 4H), 6.21 (m, 1H), 6.04(br, 2H), 4.87(m, 2H)

EXAMPLE 137

Carbamic acid (R)-1-(4-chloro-phenyl)-2-tetrazol-2-yl-ethyl ester

The procedure given in Example 134 was followed using (R)-4-chlorostyrene oxide as a reactant, instead of (R)-2-chlorostyrene oxide, to give Carbamic acid (R)-1-(4-chloro-phenyl)-2-tetrazol-2-yl-ethyl ester.

$^1$H-NMR (CDCl$_3$) δ8.54(s, 1H), 7.29-7.41(m, 4H), 6.21 (m, 1H), 6.04(br, 2H), 4.87(m, 2H)

EXAMPLE 138

Methyl-carbamic acid (R)-1-(2-chloro-phenyl)-2-tetrazol-2-yl-ethyl ester

The procedure given in Example 134 was followed using excess methylamine as a reactant, instead of excess ammonium hydroxide, to give methyl-carbamic acid (R)-1-(2-chloro-phenyl)-2-tetrazol-2-yl-ethyl ester.

$^1$H-NMR (Acetone-d$_6$) δ8.75(s, 1H), 7.2-7.8(m, 4H), 6.65 (dd, 1H), 6.5(br, 1H), 5.1(m, 2H), 2.65(d, 3H)

EXAMPLE 139

Ethyl-carbamic acid (R)-1-(2-chloro-phenyl)-2-tetrazol-2-yl-ethyl ester

The procedure given in Example 134 was followed using excess ethylamine as a reactant, instead of excess ammonium hydroxide, to give ethyl-carbamic acid (R)-1-(2-chloro-phenyl)-2-tetrazol-2-yl-ethyl ester.

$^1$H-NMR (CDCl$_3$) δ8.57(s, 1H), 8.15-8.47(m, 4H), 5.12 (m, 1H), 3.40(m, 2H), 3.0-3.2(br, 1H), 1.22(t, 3H), 1.09(t, 2H)

EXAMPLE 140

Phenyl-carbamic acid (R)-1-(2-chloro-phenyl)-2-tetrazol-2-yl-ethyl ester

The procedure given in Example 134 was followed using excess phenylamine as a reactant, instead of excess ammonium hydroxide, to give phenyl-carbamic acid (R)-1-(2-chloro-phenyl)-2-tetrazol-2-yl-ethyl ester.

$^1$H-NMR (CDCl$_3$) δ7.17-8.53 (m, 10H), 6.55(m, 1H), 6.42-6.86(br, 1H), 5.12(m, 2H)

EXAMPLE 141

Cyclopropyl-carbamic acid (R)-1-(2-chloro-phenyl)-2-tetrazol-2-yl-ethyl ester

The procedure given in Example 134 was followed using excess cyclopropylamine as a reactant, instead of excess ammonium hydroxide, to give cyclopropyl-carbamic acid (R)-1-(2-chloro-phenyl)-2-tetrazol-2-yl-ethyl ester.

$^1$H-NMR (Acetone-d$_6$) δ8.75(s, 1H), 7.45-8.24(m, 4H), 6.51(m, 1H), 6.20-6.65(br, 1H), 4.85(m, 2H), 1.6-1.84(m, 5H)

EXAMPLE 142

Carbamic acid (R)-2-tetrazol-2-yl-1-(2-trifluoromethyl-phenyl)-ethyl ester

The procedure given in Example 134 was followed using (R)-2-trifluorostyrene oxide as a reactant, instead of (R)-2-chlorostyrene oxide, to give carbamic acid (R)-2-tetrazol-2-yl-1-(2-trifluoromethyl-phenyl)-ethyl ester.

$^1$H-NMR (Acetone-d$_6$) δ8.72(s, 1H), 7.10-7.83(m, 4H), 6.67(m, 1H), 6.05-6.87(br, 2H), 4.86(m, 2H)

EXAMPLE 143

Carbamic acid (S)-2-tetrazol-2-yl-1-(2-trifluoromethyl-phenyl)-ethyl ester

The procedure given in Example 134 was followed using (S)-2-trifluorostyrene oxide as a reactant, instead of (R)-2-chlorostyrene oxide, to give carbamic acid (S)-2-tetrazol-2-yl-1-(2-trifluoromethyl-phenyl)-ethyl ester.

$^1$H-NMR (Acetone-d$_6$) δ8.74(s, 1H), 7.10-7.85(m, 4H), 6.58(m, 1H), 6.15-6.80(br, 2H), 4.87(m, 2H)

EXAMPLE 144

Carbamic acid (R)-1-(3,4-dichloro-phenyl)-2-tetrazol-2-yl-ethyl ester

The procedure given in Example 134 was followed using (R)-3,4-dichlorostyrene oxide as a reactant, instead of (R)-2-chlorostyrene oxide, to give carbamic acid (R)-1-(3,4-dichloro-phenyl)-2-tetrazol-2-yl-ethyl ester.

$^1$H-NMR (Acetone-d$_6$) δ8.73(s, 1H), 7.8-7.2(m, 3H), 6.25 (m, 1H), 6.2(br, 2H), 5.18(m, 2H)

EXAMPLE 145

Carbamic acid (S)-1-(3,4-dichloro-phenyl)-2-tetrazol-2-yl-ethyl ester

The procedure given in Example 134 was followed using (S)-3,4-dichlorostyrene oxide as a reactant, instead of (R)-2-chlorostyrene oxide, to give carbamic acid (S)-1-(3,4-dichloro-phenyl)-2-tetrazol-2-yl-ethyl ester.

$^1$H-NMR (Acetone-d$_6$) δ8.73(s, 2H), 7.8-7.2(m, 3H), 6.26 (m, 1H), 6.23(br, 2H), 5.17(m, 2H)

EXAMPLE 146

Carbamic acid (R)-1-(2,4-dichloro-phenyl)-2-tetrazol-2-yl-ethyl ester

The procedure given in Example 134 was followed using (R)-2,4-dichlorostyrene oxide as a reactant, instead of (R)-2-chlorostyrene oxide, to give carbamic acid (R)-1-(2,4-dichloro-phenyl)-2-tetrazol-2-yl-ethyl ester.

$^1$H-NMR (Acetone-d$_6$) δ8.74(s, 1H), 7.47-7.63(m, 3H), 6.53(m, 1H), 6.24(br, 2H), 5.13(m, 2H)

EXAMPLE 147

Carbamic acid (S)-1-(2,4-dichloro-phenyl)-2-tetrazol-2-yl-ethyl ester

The procedure given in Example 134 was followed using (S)-2,4-dichlorostyrene oxide as a reactant, instead of (R)-2-chlorostyrene oxide, to give carbamic acid (S)-1-(2,4-dichloro-phenyl)-2-tetrazol-2-yl-ethyl ester.

$^1$H-NMR (Acetone-d$_6$) δ8.74(s, 1H), 7.58-7.42(m, 3H), 6.53(t, 1H), 6.27(br, 2H), 5.13(m, 2H)

EXAMPLE 148

Carbamic acid 2-phenyl-1-tetrazol-2-ylmethyl-ethyl ester

The procedure given in Example 134 was followed using 2-benzyl-oxirane as a reactant, instead of (R)-2-chlorostyrene oxide, to give carbamic acid 2-phenyl-1-tetrazol-2-ylmethyl-ethyl ester.

$^1$H-NMR (CDCl$_3$) δ8.52(s, 1H), 7.34-7.27(m, 5H), 5.42 (m, 1H), 4.81(m, 2H), 4.74(m, 2H), 2.98(m, 2H)

EXAMPLE 149

Carbamic acid 2-(2,4-dichloro-phenoxy)-1-tetrazol-2-ylmethyl-ethyl ester

The procedure given in Example 134 was followed using 2-(2,4-dichloro-phenoxymethyl)-oxirane as a reactant, instead of (R)-2-chlorostyrene oxide, to give carbamic acid 2-(2,4-dichloro-phenoxy)-1-tetrazol-2-ylmethyl-ethyl ester.

$^1$H-NMR (Acetone-$d_6$) δ8.76(s, 1H), 7.38(m, 3H), 5.03(m, 2H), 4.89(m, 1H), 4.71-5.01(br, 2H), 4.31(m, 2H)

EXAMPLE 150

Carbamic acid 2-(3,4-dichloro-phenoxy)-1-tetrazol-2-ylmethyl-ethyl ester

The procedure given in Example 134 was followed using 2-(3,4-dichloro-phenoxymethyl)-oxirane as a reactant, instead of (R)-2-chlorostyrene oxide, to give carbamic acid 2-(3,4-dichloro-phenoxy)-1-tetrazol-2-ylmethyl-ethyl ester.

$^1$H-NMR (Acetone-$d_6$) δ8.75(s, 1H), 7.53-7.02(m, 3H), 6.07(br, 2H), 5.56(t, 1H), 5.15(d, 2H), 4.35(m, 2H)

EXAMPLE 151

Carbamic acid 2-(4-chloro-phenoxy)-1-tetrazol-2-ylmethyl-ethyl ester

The procedure given in Example 134 was followed using 2-(4-chloro-phenoxymethyl)-oxirane as a reactant, instead of (R)-2-chlorostyrene oxide, to give carbamic acid 2-(4-chloro-phenoxy)-1-tetrazol-2-ylmethyl-ethyl ester.

$^1$H-NMR (Acetone-$d_6$) δ8.76(s, 1H), 7.50(m, 1H), 7.27(m, 1H), 7.04(m, 1H), 6.07(br, 2H), 5.56(t, 1H), 5.15(d, 2H), 4.35(m, 2H)

EXAMPLE 152

Carbamic acid 2-(2-chloro-phenoxy)-1-tetrazol-2-ylmethyl-ethyl ester

The procedure given in Example 134 was followed using 2-(2-chloro-phenoxymethyl)-oxirane as a reactant, instead of (R)-2-chlorostyrene oxide, to give carbamic acid 2-(2-chloro-phenoxy)-1-tetrazol-2-ylmethyl-ethyl ester.

$^1$H-NMR (Acetone-$d_6$) δ8.76(s, 1H), 7.47-6.98(m, 4H), 6.07(br, 2H), 5.60(t, 1H), 5.20(d, 2H), 4.39(m, 2H)

EXAMPLE 153

4-Benzyl-piperidine-1-carboxylic acid 2-(2-chloro-phenoxy)-1-tetrazol-2-ylmethyl-ethyl ester The procedure given in Example 152 was followed using 4-benzyl-piperidine as a reactant, instead of excess ammonium hydroxide, to give 4-benzyl-piperidine-1-carboxylic acid 2-(2-chloro-phenoxy)-1-tetrazol-2-ylmethyl-ethyl ester.

$^1$H-NMR (Acetone-$d_6$) δ8.77(s, 1H), 7.48-6.99(m, 11H), 5.30(t, 1H), 5.25(d, 2H), 4.44(d, 2H), 3.95(m, 1H), 2.54(m, 3H), 1.66(m, 3H), 1.04(m, 2H)

EXAMPLE 154

4-Benzyl-piperidine-1-carboxylic acid (R)-1-(2-chloro-phenyl)-2-tetrazol-2-yl-ethyl ester The procedure given in Example 134 was followed using excess 4-benzyl-piperidine as a reactant, instead of excess ammonium hydroxide, to give 4-benzyl-piperidine-1-carboxylic acid (R)-1-(2-chloro-phenyl)-2-tetrazol-2-yl-ethyl ester.

$^1$H-NMR (Acetone-$d_6$) δ7.91(s, 1H), 7.28(m, 7H), 7.03(s, 2H), 4.0 (d, 2H), 3.12(t, 2H), 2.6(d, 2H), 1.74 (m, 4H), 1.33 (m, 4H)

EXAMPLE 155

4-Benzyl-piperidine-1-carboxylic acid (S)-1-(2-chloro-phenyl)-2-tetrazol-2-yl-ethyl ester The procedure given in Example 135 was followed using excess 4-benzyl-piperidine as a reactant, instead of excess ammonium hydroxide, to give 4-benzyl-piperidine-1-carboxylic acid (S)-1-(2-chloro-phenyl)-2-tetrazol-2-yl-ethyl ester.

$^1$H-NMR (Acetone-$d_6$) δ7.90(s, 1H), 6.95-7.5(m, 7H), 7.02(s, 2H), 4.05 (d, 2H), 3.08(t, 2H), 2.63(d, 2H), 1.75 (m, 4H), 1.35(m, 4H)

EXAMPLE 156

4-Benzyl-piperidine-1-carboxylic acid 2-(4-chloro-phenoxy)-1-tetrazol-2-ylmethyl-ethyl ester The procedure given in Example 151 was followed using excess 4-benzyl-piperidine as a reactant, instead of excess ammonium hydroxide, to give 4-benzyl-piperidine-1-carboxylic acid 2-(4-chloro-phenoxy)-1-tetrazol-2-ylmethyl-ethyl ester.

$^1$H-NMR (Acetone-$d_6$) δ7.92(s, 1H), 7.37(s, 1H), 7.28(m, 7H), 7.03(s, 1H), 4.05(d, 2H), 3.08(t, 2H), 2.59(d, 2H), 2.06 (m, 2H), 1.75(m, 4H), 1.35(m, 4H)

EXAMPLE 157

Carbamic acid 2-(2,5-dichloro-phenoxy)-1-tetrazol-2-ylmethyl-ethyl ester

The procedure given in Example 134 was followed using 2-(2,5-dichloro-phenoxymethyl)-oxirane as a reactant, instead of (R)-2-chlorostyrene oxide, to give carbamic acid 2-(2,5-dichloro-phenoxy)-1-tetrazol-2-ylmethyl-ethyl ester.

$^1$H-NMR (Acetone-$d_6$) δ8.76(s, 1H), 7.49(d, 1H), 7.29(s, 1H), 7.05(d, 1H), 6.08(br, 2H), 5.62(m, 1H), 5.21(d, 2H), 4.46(m, 2H)

EXAMPLE 158

3-Phenethyl-pyrrolidine-1-carboxylic acid 2-(2,5-dichloro-phenoxy)-1-tetrazol-2-ylmethyl-ethyl ester The procedure given in Example 157 was followed using excess 3-phenethyl-pyrrolidine as a reactant, instead of excess ammonium hydroxide, to give 3-phenethyl-pyrrolidine-1-carboxylic acid 2-(2,5-dichloro-phenoxy)-1-tetrazol-2-ylmethyl-ethyl ester.

$^1$H-NMR (Acetone-$d_6$) δ8.06(s, 1H), 7.52(s, 1H), 7.29(m, 6H), 7.02(s, 1H), 3.82(m, 1H), 3.37(d, 2H), 2.99(d, 2H), 2.71(t, 2H), 2.2(m, 3H), 1.77(m, 6H)

EXAMPLE 159

4-(3,4-Dichloro-benzyl)-piperidine-1-carboxylic acid 2-(2-chloro-phenoxy)-1-tetrazol-2-ylmethyl-ethyl ester The procedure given in Example 152 was followed using excess 4-(3,4-dichloro-benzyl)-piperidine as a reactant, instead of excess ammonium hydroxide, to give 4-(3,4-dichloro-benzyl)-piperidine-1-carboxylic acid 2-(2-chloro-phenoxy)-1-tetrazol-2-ylmethyl-ethyl ester.

$^1$H-NMR (Acetone-d$_6$) δ7.9(s, 1H), 7.47(m, 3H), 7.36(s, 1H), 7.22(m, 2H), 7.02(s, 1H), 4.05(d, 2H), 3.1(t, 2H), 2.65(d, 2H), 2.05 (m, 2H), 1.76(m, 4H), 1.3(m, 4H)

EXAMPLE 160

4-(3,4-Dichloro-benzyl)-piperidine-1-carboxylic acid 2-(2,4-dichloro-phenoxy)-1-tetrazol-2-ylmethyl-ethyl ester The procedure given in Example 149 was followed using excess 4-(3,4-dichloro-benzyl)-piperidine as a reactant, instead of excess ammonium hydroxide, to give 4-(3,4-dichloro-benzyl)-piperidine-1-carboxylic acid 2-(2,4-dichloro-phenoxy)-1-tetrazol-2-ylmethyl-ethyl ester.

$^1$H-NMR (Acetone-d$_6$) δ7.91(s, 1H), 7.50(m, 2H), 7.36(s, 1H), 7.23(m, 2H), 7.02(s, 1H), 4.05(d, 2H), 3.08(t, 2H), 2.66 (d, 2H), 2.08(m, 2H), 1.76(m, 4H), 1.37(m, 4H)

EXAMPLE 161

4-(3,4-Dichloro-benzyl)-piperidine-1-carboxylic acid 2-(3,4-dichloro-phenoxy)-1-tetrazol-2-ylmethyl-ethyl ester The procedure given in Example 150 was followed using excess 4-(3,4-dichloro-benzyl)-piperidine as a reactant, instead of excess ammonium hydroxide, to give 4-(3,4-dichloro-benzyl)-piperidine-1-carboxylic acid 2-(3,4-dichloro-phenoxy)-1-tetrazol-2-ylmethyl-ethyl ester.

$^1$H-NMR (Acetone-d$_6$) δ7.91(s, 1H), 7.47(m, 2H), 7.35(s, 1H), 7.23(m, 2H), 7.02(s, 1H), 4.08(d, 2H), 3.10(t, 2H), 2.65 (d, 2H), 1.99(m, 2H), 1.75(m, 4H), 1.3(m, 4H)

EXAMPLE 162

Carbamic acid (R)-1-(2-chloro-phenyl)-2-tetrazol-1-yl-ethyl ester

To a solution of 1H-tetrazole (2.4 mmol) and lithium carbonate (4.8 mmol) in DMF (100 ml), (R)-2-chlorostyrene oxide (2 mmol) was slowly added to give enantiomerically (R)-configured alcohol compound represented by the general formula (XII) where in, G is 2-chlorophenyl, m is 0, Y is hydrogen, n is 0 and A is 1N-tetrazole. The reaction was stirred for 4 h at 120° C. and then cooled to 25° C. This solution was then concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 3 h, followed by the addition of excess ammonium hydroxide (50 ml). After 5 h stirring at room temperature, the organic layer was isolated and washed with brine. The resulting organic layer was dried and concentrated in vacuo.

The preparation procedure of 1N-azole is same as that of 2N-azole in example except the ratio of mobile phase of column chromatography. 1N-Azole is more polar than 2N-azole in chromatographic condition and separated by eluting with an increasing ratio of ethyl acetate in hexane after elution of 2N-azole to give carbamic acid (R)-1-(2-chloro-phenyl)-2-tetrazol-1-yl-ethyl ester.

$^1$H-NMR (Acetone-d$_6$) δ9.14(s, 1H), 7.31-7.59(m, 4H), 6.42(m, 1H), 6.0-6.75(br, 2H), 5.03(m, 2H)

EXAMPLE 163

Carbamic acid (S)-1-(2-chloro-phenyl)-2-tetrazol-1-yl-ethyl ester

The procedure given in Example 162 was followed using (S)-2-chlorostyrene oxide as a reactant, instead of (R)-2-chlorostyrene oxide, to give carbamic acid (S)-1-(2-chloro-phenyl)-2-tetrazol-1-yl-ethyl ester.

$^1$H-NMR (CDCl$_3$) δ8.75(s, 1H), 7.10-7.4(m, 4H), 6.35(m, 1H), 5.67(br, 2H), 4.83(m, 2H)

EXAMPLE 164

Carbamic acid (S)-1-(3,4-dichloro-phenyl)-2-tetrazol-1-yl-ethyl ester

The procedure given in Example 162 was followed using (S)-3,4-dichlorostyrene oxide as a reactant, instead of (R)-2-chlorostyrene oxide, to give carbamic acid (S)-1-(3,4-dichloro-phenyl)-2-tetrazol-1-yl-ethyl ester.

$^1$H-NMR (Acetone-d$_6$) δ9.16(s, 1H), 7.59(m, 2H), 7.35 (dd, 1H), 6.39(br, 2H), 6.17(t, 1H), 5.05(d, 2H)

EXAMPLE 165

Carbamic acid 2-phenyl-1-tetrazol-1-ylmethyl-ethyl ester

The procedure given in Example 162 was followed using 2-benzyl-oxirane as a reactant, instead of (R)-2-chlorostyrene oxide, to give carbamic acid 2-phenyl-1-tetrazol-1-ylmethyl-ethyl ester.

$^1$H-NMR (CDCl$_3$) δ8.62(s, 1H), 7.39-7.27(m, 5H), 5.29 (m, 1H), 4.78(br, 2H), 4.60(m, 2H), 2.90(m, 2H)

EXAMPLE 166

Carbamic acid (S)-1-(2,6-dichloro-phenyl)-2-tetrazol-1-yl-ethyl ester

The procedure given in Example 162 was followed using (S)-2,6-dichlorostyrene oxide as a reactant, instead of (R)-2-chlorostyrene oxide, to give carbamic acid (S)-1-(2,6-dichloro-phenyl)-2-tetrazol-1-yl-ethyl ester.

$^1$H-NMR (CDCl$_3$) δ8.8(s, 1H), 7.4-7.2(m, 3H), 6.72(m, 1H), 5.29-4.87(m, 2H), 5.08(br, 2H)

EXAMPLE 167

Carbamic acid 2-(4-chloro-phenoxy)-1-tetrazol-1-ylmethyl-ethyl ester

The procedure given in Example 162 was followed using 2-(4-chloro-phenoxymethyl)-oxirane as a reactant, instead of (R)-2-chlorostyrene oxide, to give carbamic acid 2-(4-chloro-phenoxy)-1-tetrazol-1-ylmethyl-ethyl ester.

¹H-NMR (Acetone-d₆) δ9.17(s, 1H), 7.32(m, 2H), 7.04(m, 2H), 6.18(br, 2H), 5.44(t, 1H), 5.00(d, 2H), 4.22(d, 2H)

EXAMPLE 168

Carbamic acid 2-(2-chloro-phenoxy)-1-tetrazol-1-ylmethyl-ethyl ester

The procedure given in Example 162 was followed using 2-(2-chloro-phenoxymethyl)-oxirane as a reactant, instead of (R)-2-chlorostyrene oxide, to give carbamic acid 2-(2-chloro-phenoxy)-1-tetrazol-1-ylmethyl-ethyl ester.
¹H-NMR (Acetone-d₆) δ9.20(s, 1H), 7.47-6.98(m, 4H), 6.19(br, 2H), 5.50(t, 1H), 5.05(d, 2H), 4.30(m, 2H)

EXAMPLE 169

4-Benzyl-piperidine-1-carboxylic acid 2-(2-chloro-phenoxy)-1-tetrazol-1-ylmethyl-ethyl ester The procedure given in Example 168 was followed using excess 4-benzyl-piperidine as a reactant, instead of excess ammonium hydroxide, to give 4-benzyl-piperidine-1-carboxylic acid 2-(2-chloro-phenoxy)-1-tetrazol-1-ylmethyl-ethyl ester.
¹H-NMR (Acetone-d₆) δ9.26(s, 1H), 7.36-7.01(m, 11H), 5.52(t, 1H), 5.05(d, 2H), 4.41(m, 2H), 3.14-1.22(m, 9.H)

EXAMPLE 170

4-Benzyl-piperidine-1-carboxylic acid 2-(4-chloro-phenoxy)-1-tetrazol-1-ylmethyl-ethyl ester The procedure given in Example 167 was followed using excess 4-benzyl-piperidine as a reactant, instead of excess ammonium hydroxide, to give 4-benzyl-piperidine-1-carboxylic acid 2-(4-chloro-phenoxy)-1-tetrazol-1-ylmethyl-ethyl ester.
¹H-NMR (Acetone-d₆) δ8.02(s, 1H), 7.45 (s, 1H), 7.29(m, 7H), 7.01(s, 1H), 4.05(d, 2H), 3.07(t, 2H), 2.63(d, 2H), 2.07 (m, 2H), 1.75(m, 4H), 1.34(m, 4H)

EXAMPLE 171

Carbamic acid (R)-1-(2-chloro-phenyl)-2-[1,2,3]triazol-2-yl-ethyl ester

To a solution of 1H-1,2,3-triazole (2.4 mmol) and lithium carbonate (4.8 mmol) in DMF (100 ml), (R)-2-chlorostyrene oxide (2 mmol) was slowly added to give enantiomerically (R)-configured alcohol compound represented by the general formula (XII) where in, G is 2-chlorophenyl, m is 0, Y is hydrogen, n is 0 and A is 2N-1,2,3-triazole. The reaction was stirred for 4 h at 120° C. and then cooled to 25° C. This solution was then concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 3 h, followed by the addition of excess ammonium hydroxide (50 ml). After 5 h stirring at room temperature, the organic layer was isolated and washed with brine. The resulting organic layer was dried and concentrated in vacuo. The residue was purified by column chromatography (ethyl acetate:hexane=1:2) and recrystallized from dichloromethane and ethyl ether (1:1) to give carbamic acid (R)-1-(2-chloro-phenyl)-2-[1,2,3]triazol-2-yl-ethyl ester.
¹H-NMR (Acetone-d₆) δ7.69(s, 2H), 7.6-7.2(m, 4H), 6.59 (dd, 1H), 6.11(br, 2H), 4.78(d, 2H)

EXAMPLE 172

Carbamic acid (S)-1-(2-chloro-phenyl)-2-[1,2,3]triazol-2-yl-ethyl ester

The procedure given in Example 171 was followed using (S)-2-chlorostyrene oxide as a reactant, instead of (R)-2-chlorostyrene oxide, to give carbamic acid (S)-1-(2-chloro-phenyl)-2-[1,2,3]triazol-2-yl-ethyl ester.
¹H-NMR (Acetone-d₆) δ7.71(s, 2H), 7.7-7.1(m, 4H), 6.60 (dd, 1H), 6.14(br, 2H), 4.79(d, 2H)

EXAMPLE 173

Carbamic acid (S)-1-(4-chloro-phenyl)-2-[1,2,3]triazol-2-yl-ethyl ester

The procedure given in Example 171 was followed using (S)-4-chlorostyrene oxide as a reactant, instead of (R)-2-chlorostyrene oxide, to give carbamic acid (S)-1-(4-chloro-phenyl)-2-[1,2,3]triazol-2-yl-ethyl ester.
¹H-NMR (Acetone-d₆) δ7.68(s, 2H), 7.41(m, 4H), 6.23(m, 1H), 6.15(br, 2H), 4.82(m, 2H)

EXAMPLE 174

Carbamic acid (R)-1-(4-chloro-phenyl)-2-[1,2,3]triazol-2-yl-ethyl ester

The procedure given in Example 171 was followed using (R)-4-chlorostyrene oxide as a reactant, instead of (R)-2-chlorostyrene oxide, to give carbamic acid (R)-1-(4-chloro-phenyl)-2-[1,2,3]triazol-2-yl-ethyl ester.
¹H-NMR (Acetone-d₆) δ7.67(s, 2H), 7.41(m, 4H), 6.22(m, 1H), 6.09(br, 2H), 4.80(m, 2H)

EXAMPLE 175

Carbamic acid (S)-1-(3,4-dichloro-phenyl)-2-[1,2,3]triazol-2-yl-ethyl ester

The procedure given in Example 171 was followed using (S)-3,4-dichlorostyrene oxide as a reactant, instead of (R)-2-chlorostyrene oxide, to give carbamic acid (S)-1-(3,4-dichloro-phenyl)-2-[1,2,3]triazol-2-yl-ethyl ester.
¹H-NMR (Acetone-d₆) δ7.67(s, 2H), 7.7-7.2(m, 3H), 6.19 (m, 1H), 6.16(br, 2H), 4.84(m, 2H)

EXAMPLE 176

Carbamic acid (R)-1-(3,4-dichloro-phenyl)-2-[1,2,3]triazol-2-yl-ethyl ester

The procedure given in Example 171 was followed using (R)-3,4-dichlorostyrene oxide as a reactant, instead of (R)-2-chlorostyrene oxide, to give carbamic acid (R)-1-(3,4-dichloro-phenyl)-2-[1,2,3]triazol-2-yl-ethyl ester.
¹H-NMR (Acetone-d₆) δ8-7(m, 5H), 6.18(m, 1H), 6.16(br, 2H), 4.84(m, 2H)

EXAMPLE 177

Carbamic acid (S)-1-(2,4-dichloro-phenyl)-2-[1,2,3]triazol-2-yl-ethyl ester

The procedure given in Example 171 was followed using (S)-2,4-dichlorostyrene oxide as a reactant, instead of (R)-2-chlorostyrene oxide, to give carbamic acid (S)-1-(2,4-dichloro-phenyl)-2-[1,2,3]triazol-2-yl-ethyl ester.

$^1$H-NMR (Acetone-$d_6$) δ7.68(s, 2H), 7.60-7.44(m, 3H), 6.51(t, 1H), 6.18(s, 2H), 4.79(d, 2H)

EXAMPLE 178

Carbamic acid (R)-1-(2,4-dichloro-phenyl)-2-[1,2,3]triazol-2-yl-ethyl ester

The procedure given in Example 171 was followed using (R)-2,4-dichlorostyrene oxide as a reactant, instead of (R)-2-chlorostyrene oxide, to give carbamic acid (R)-1-(2,4-dichloro-phenyl)-2-[1,2,3]triazol-2-yl-ethyl ester.

$^1$H-NMR (Acetone-$d_6$) δ7.68(s, 2H), 7.55-7.4(m, 3H), 6.51(dd, 1H), 6.12(br, 2H), 4.81(d, 2H)

EXAMPLE 179

4-Benzyl-piperidine-1-carboxylic acid (S)-1-(2-chloro-phenyl)-2-[1,2,3]triazol-2-yl-ethyl ester The procedure given in Example 172 was followed using excess 4-benzyl-piperidine as a reactant, instead of excess ammonium hydroxide, to give 4-benzyl-piperidine-1-carboxylic acid (S)-1-(2-chloro-phenyl)-2-[1,2,3]triazol-2-yl-ethyl ester.

$^1$H-NMR (Acetone-$d_6$) δ7.91(s, 2H), 7.3(m, 7H), 7.03 (s, 2H), 4.05 (d, 2H), 3.08(t, 2H), 2.63(d, 2H), 1.74 (m, 4H), 1.35(m, 4H)

EXAMPLE 180

4-Benzyl-piperidine-1-carboxylic acid (R)-1-(2-chloro-phenyl)-2-[1,2,3]triazol-2-yl-ethyl ester The procedure given in Example 171 was followed using excess 4-benzyl-piperidine as a reactant, instead of excess ammonium hydroxide, to give 4-benzyl-piperidine-1-carboxylic acid (R)-1-(2-chloro-phenyl)-2-[1,2,3]triazol-2-yl-ethyl ester.

$^1$H-NMR (Acetone-$d_6$) δ7.98(s, 2H), 7.2-7.55(m, 7H), 7.08 (s, 2H), 4.05 (d, 2H), 3.02(t, 2H), 2.59(d, 2H), 1.70 (m, 4H), 1.29(m, 4H)

EXAMPLE 181

Carbamic acid 2-(4-chloro-phenoxy)-1-[1,2,3]triazol-2-ylmethyl-ethyl ester

The procedure given in Example 171 was followed using 2-(4-chloro-phenoxymethyl)-oxirane as a reactant, instead of (R)-2-chlorostyrene oxide, to give carbamic acid 2-(4-chloro-phenoxy)-1-[1,2,3]triazol-2-ylmethyl-ethyl ester.

$^1$H-NMR (Acetone-$d_6$) δ7.70(s, 2H), 7.3(d, 2H), 7.0 (d, 2H), 5.7-6.3(br, 2H), 5.5(t, 1H), 4.83(d, 2H), 4.22(m, 2H)

EXAMPLE 182

Carbamic acid 2-(2-chloro-phenoxy)-1-[1,2,3]triazol-2-ylmethyl-ethyl ester

The procedure given in Example 171 was followed using 2-(2-chloro-phenoxymethyl)-oxirane as a reactant, instead of (R)-2-chlorostyrene oxide, to give carbamic acid 2-(2-chloro-phenoxy)-1-[1,2,3]triazol-2-ylmethyl-ethyl ester.

$^1$H-NMR (Acetone-$d_6$) δ7.71(s, 2H), 7.25(m, 4H), 6.0(br, 2H), 5.56(m, 1H), 4.9(d, 2H), 4.3(m, 2H)

EXAMPLE 183

3-Phenethyl-pyrrolidine-1-carboxylic acid 2-(2-chloro-phenoxy)-1-[1,2,3]triazol-2-ylmethyl-ethyl ester The procedure given in Example 182 was followed using excess 3-phenethyl-pyrrolidine as a reactant, instead of excess ammonium hydroxide, to give 3-phenethyl-pyrrolidine-1-carboxylic acid 2-(2-chloro-phenoxy)-1-[1,2,3]triazol-2-ylmethyl-ethyl ester.

$^1$H-NMR (Acetone-$d_6$) δ8.06(s, 2H), 7.51(s, 1H), 7.25(m, 7H), 7.01(s, 1H), 3.75(m, 1H), 3.34(d, 2H), 3.01(d, 2H), 2.7(t, 2H), 2.15(m, 3H), 1.82(m, 6H)

EXAMPLE 184

Carbamic acid 2-(2,4-dichloro-phenoxy)-1-[1,2,3]triazol-2-ylmethyl-ethyl ester

The procedure given in Example 171 was followed using 2-(2,4-dichloro-phenoxymethyl)-oxirane as a reactant, instead of (R)-2-chlorostyrene oxide, to give carbamic acid 2-(2,4-dichloro-phenoxy)-1-[1,2,3]triazol-2-ylmethyl-ethyl ester.

$^1$H-NMR (Acetone-$d_6$) δ7.71(s, 2H), 7.5(s, 1H), 7.36(d, 1H), 7.19(d, 1H), 6.01(br, 2H), 5.55(m, 1H), 4.88(d, 2H), 4.32(m, 2H)

EXAMPLE 185

3-Phenethyl-pyrrolidine-1-carboxylic acid 2-(2,4-dichloro-phenoxy)-1-[1,2,3]triazol-2-ylmethyl-ethyl ester The procedure given in Example 184 was followed using excess 3-phenethyl-pyrrolidine as a reactant, instead of excess ammonium hydroxide, to give 3-phenethyl-pyrrolidine-1-carboxylic acid 2-(2,4-dichloro-phenoxy)-1-[1,2,3]triazol-2-ylmethyl-ethyl ester.

$^1$H-NMR (Acetone-$d_6$) δ8.05(s, 2H), 7.51(s, 1H), 7.28(m, 6H), 7.01(s, 1H), 3.77(m, 1H), 3.35(d, 2H), 3.03(d, 2H), 2.73(t, 2H), 2.15(m, 3H), 1.79(m, 6H)

EXAMPLE 186

Carbamic acid 2-(3,4-dichloro-phenoxy)-1-[1,2,3]triazol-2-ylmethyl-ethyl ester

The procedure given in Example 171 was followed using 2-(3,4-dichloro-phenoxymethyl)-oxirane as a reactant, instead of (R)-2-chlorostyrene oxide, to give carbamic acid 2-(3,4-dichloro-phenoxy)-1-[1,2,3]triazol-2-ylmethyl-ethyl ester.

¹H-NMR (Acetone-d₆) δ7.71(s, 2H), 7.50(s, 1H), 7.34(d, 1H), 7.19(d, 1H), 6.03(br, 2H), 5.56(m, 1H), 4.89(m, 2H), 4.35(m, 2H)

EXAMPLE 187

3-Phenethyl-pyrrolidine-1-carboxylic acid 2-(3,4-dichloro-phenoxy)-1-[1,2,3]triazol-2-ylmethyl-ethyl ester The procedure given in Example 186 was followed using excess 3-phenethyl-pyrrolidine as a reactant, instead of excess ammonium hydroxide, to give 3-phenethyl-pyrrolidine-1-carboxylic acid 2-(3,4-dichloro-phenoxy)-1-[1,2,3] triazol-2-ylmethyl-ethyl ester.

¹H-NMR (Acetone-d₆) δ8.06(s, 2H), 7.52(s, 1H), 7.28(m, 6H), 7.01(s, 1H), 3.80(m, 1H), 3.35(d, 2H), 3.02(d, 2H), 2.7(t, 2H), 2.16(m, 3H), 1.78(m, 6H)

EXAMPLE 188

Carbamic acid (R)-1-(2-chloro-phenyl)-2-[1,2,3]triazol-1-yl-ethyl ester

To a solution of 1H-1,2,3-triazole (2.4 mmol) and lithium carbonate (4.8 mmol) in DMF (100 ml), (R)-2-chlorostyrene oxide (2 mmol) was slowly added to give enantiomerically (R)-configured alcohol compound represented by the general formula (XII) where in, G is 2-chlorophenyl, m is 0, Y is hydrogen, n is 0 and A is 1N-1,2,3-triazole. The reaction was stirred for 4 h at 120° C. and then cooled to 25° C. This solution was then concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 3 h, followed by the addition of excess ammonium hydroxide (50 ml). After 5 h stirring at room temperature, the organic layer was isolated and washed with brine. The resulting organic layer was dried and concentrated in vacuo.

The preparation procedure of 1N-azole is same as that of 2N-azole in example except the ratio of mobile phase of column chromatography. 1N-Azole is more polar than 2N-azole in chromatographic condition and separated by eluting with an increasing ratio of ethyl acetate in hexane after elution of 2N-azole to give carbamic acid (R)-1-(2-chloro-phenyl)-2-[1,2,3]triazol-1-yl-ethyl ester.

¹H-NMR (CDCl₃) δ7.61(s, 1H), 7.61(s, 1H), 7.20-7.38(m, 4H), 6.35(m, 1H), 5.38(br, 2H), 4.75(m, 2H)

EXAMPLE 189

Carbamic acid (S)-1-(2-chloro-phenyl)-2-[1,2,3]triazol-1-yl-ethyl ester

The procedure given in Example 188 was followed using (S)-2-chlorostyrene oxide as a reactant, instead of (R)-2-chlorostyrene oxide, to give carbamic acid (S)-1-(2-chloro-phenyl)-2-[1,2,3]triazol-1-yl-ethyl ester.

¹H-NMR (CDCl₃) δ7.53(s, 1H), 7.48(s, 1H), 6.92-7.37(m, 4H), 6.17(m, 1H), 5.72(br, 2H), 4.65(m, 2H)

EXAMPLE 190

Carbamic acid (R)-1-(3,4-dichloro-phenyl)-2-[1,2,3]tetrazol-1-yl-ethyl ester The procedure given in Example 188 was followed using (R)-3,4-dichlorostyrene oxide as a reactant, instead of (R)-2-chlorostyrene oxide, to give carbamic acid (R)-1-(3,4-dichloro-phenyl)-2-[1,2,3]triazol-1-yl-ethyl ester.

¹H-NMR (Acetone-d₆) δ7.98(s, 1H), 7.67(s, 1H), 7.8-7.1 (m, 3H), 6.34(br, 2H), 6.12(m, 1H), 4.90(d, 2H)

EXAMPLE 191

Carbamic acid (R)-1-(2,4-dichloro-phenyl)-2-[1,2,3]triazol-1-yl-ethyl ester

The procedure given in Example 188 was followed using (R)-2,4-dichlorostyrene oxide as a reactant, instead of (R)-2-chlorostyrene oxide, to give carbamic acid (R)-1-(2,4-dichloro-phenyl)-2-[1,2,3]triazol-1-yl-ethyl ester.

¹H-NMR (Acetone-d₆) δ8.78(s, 1H), 7.46(m, 3H), 5.98(m, 1H), 5.50-6.34(br, 2H), 5.13(m, 2H)

EXAMPLE 192

Carbamic acid 2-(4-chloro-phenoxy)-1-[1,2,3]triazol-1-ylmethyl-ethyl ester

The procedure given in Example 188 was followed using 2-(4-chloro-phenoxymethyl)-oxirane as a reactant, instead of (R)-2-chlorostyrene oxide, to give carbamic acid 2-(4-chloro-phenoxy)-1-[1,2,3]triazol-1-ylmethyl-ethyl ester.

¹H-NMR (Acetone-d₆) δ8.0(s, 1H), 7.70(s, 1H), 7.34(d, 2H), 7.0 (d, 2H), 5.9-6.4(br, 2H), 5.41(t, 1H), 4.86(d, 2H), 4.16(m, 2H)

EXAMPLE 193

Carbamic acid (R)-1-(2-chloro-phenyl)-2-(5-phenyl-tetrazol-2-yl)-ethyl ester To a solution of 5-phenyl-1H-tetrazole (2.4 mmol) and lithium carbonate (4.8 mmol) in DMF (100 ml), (R)-2-chlorostyrene oxide (2 mmol) was slowly added to give enantiomerically (R)-configured alcohol compound represented by the general formula (XII) where in, G is 2-chlorophenyl, m is 0, Y is hydrogen, n is 0 and A is 2N-5-phenyl-tetrazole. The reaction was stirred for 4 h at 120° C. and then cooled to 25° C. This solution was then concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 3 h, followed by the addition of excess ammonium hydroxide (50 ml). After 5 h stirring at room temperature, the organic layer was isolated and washed with brine. The resulting organic layer was dried and concentrated in vacuo. The residue was purified by column chromatography (ethyl acetate:hexane=1:2) and recrystallized from dichloromethane and ethyl ether (1:1) to give carbamic acid (R)-1-(2-chloro-phenyl)-2-(5-phenyl-tetrazol-2-yl)-ethyl ester.

¹H-NMR (Acetone-d₆) δ8.1-8.3(m, 2H), 7.2-7.8(m, 7H), 6.67(t, 1H), 6.25(br, 2H), 5.14(d, 2H)

EXAMPLE 194

Carbamic acid (S)-1-(2-chloro-phenyl)-2-(5-phenyl-tetrazol-2-yl)-ethyl ester

The procedure given in Example 193 was followed using (S)-2-chlorostyrene oxide as a reactant, instead of (R)-2-chlorostyrene oxide, to give carbamic acid (S)-1-(2-chloro-phenyl)-2-(5-phenyl-tetrazol-2-yl)-ethyl ester.

¹H-NMR (Acetone-d₆) δ8.11 (dd, 2H), 7.57-7.40(m, 7H), 6.65(t, 1H), 6.24(br, 2H), 5.13(d, 2H)

EXAMPLE 195

Methyl-carbamic acid (R)-1-(2-chloro-phenyl)-2-(5-phenyl-tetrazol-2-yl)-ethyl ester The procedure given in Example 193 was followed using excess methylamine as a reactant, instead of excess ammonium hydroxide, to give methyl-carbamic acid (R)-1-(2-chloro-phenyl)-2-(5-phenyl-tetrazol-2-yl)-ethyl ester.

¹H-NMR (Acetone-d₆) δ8.05-8.25(m, 2H), 7.3-7.7(m, 7H), 6.7(t, 1H), 6.55(br, 1H), 5.13(d, 2H), 2.64(d, 3H)

EXAMPLE 196

Methyl-carbamic acid (S)-1-(2-chloro-phenyl)-2-(5-phenyl-tetrazol-2-yl)-ethyl ester The procedure given in Example 194 was followed using excess methylamine as a reactant, instead of excess ammonium hydroxide, to give methyl-carbamic acid (S)-1-(2-chloro-phenyl)-2-(5-phenyl-tetrazol-2-yl)-ethyl ester.

¹H-NMR (Acetone-d₆) δ8.14 (m, 2H), 7.59-7.39(m, 7H), 6.67(t, 1H), 6.54(br, 1H), 5.14(m, 2H), 2.64(d, 3H)

EXAMPLE 197

Carbamic acid (S)-1-(2-chloro-phenyl)-2-(5-phenyl-tetrazol-1-yl)-ethyl ester

To a solution of 5-phenyl-1H-tetrazole (2.4 mmol) and lithium carbonate (4.8 mmol) in DMF (100 ml), (S)-2-chlorostyrene oxide (2 mmol) was slowly added to give enantiomerically (S)-configured alcohol compound represented by the general formula (XII) where in, G is 2-chlorophenyl, m is 0, Y is hydrogen, n is 0 and A is 1N-5-phenyl-tetrazole. The reaction was stirred for 4 h at 120° C. and then cooled to 25° C. This solution was then concentrated on a rotary evaporator and diluted with ethyl acetate. This mixture was washed with brine. The resulting organic layer was dried and concentrated in vacuo. This alcohol compound was dissolved in methylene chloride (50 ml) and was added 1,1'-carbonyl diimidazole (8 mmol). The reaction mixture was stirred at room temperature for 3 h, followed by the addition of excess ammonium hydroxide (50 ml). After 5 h stirring at room temperature, the organic layer was isolated and washed with brine. The resulting organic layer was dried and concentrated in vacuo.

The preparation procedure of 1N-azole is same as that of 2N-azole in example except the ratio of mobile phase of column chromatography. 1N-Azole is more polar than 2N-azole in chromatographic condition and separated by eluting with an increasing ratio of ethyl acetate in hexane after elution of 2N-azole to give carbamic acid (S)-1-(2-chloro-phenyl)-2-(5-phenyl-tetrazol-1-yl)-ethyl ester.

¹H-NMR (Acetone-d₆) δ7.75-7.60 (m, 4H), 7.36(s, 3H), 7.44(m, 1H), 6.18(br, 2H), 4.96(t, 2H)

EXAMPLE 198

Methyl-carbamic acid (S)-1-(2-chloro-phenyl)-2-(5-phenyl-tetrazol-1-yl)-ethyl ester The procedure given in Example 197 was followed using excess methylamine as a reactant, instead of excess ammonium hydroxide, to give methyl-carbamic acid (S)-1-(2-chloro-phenyl)-2-(5-phenyl-tetrazol-1-yl)-ethyl ester.

¹H-NMR (Acetone-d₆) δ7.75-7.60(m, 4H), 7.34(m, 3H), 6.45(m, 1H), 6.38(br 1H), 4.97(m, 2H), 2.63(d, 3H)

EXAMPLE 199

O-1-(2-Chloro-phenyl)-2-tetrazol-2-yl ethyl allophanate

To a solution of 1H-tetrazole (2.4 mmol) and lithium carbonate (4.8 mmol) in DMF (100 ml), 2-chlorostyrene oxide (2 mmol) was slowly added to give alcohol compound represented by the general formula (XII) where in, G is 2-chlorophenyl, m is 0, Y is hydrogen, n is 0 and A is 2N-tetrazole. The reaction was stirred for 4 h at 120° C. and then cooled to 25° C. This solution was then concentrated on a rotary evaporator and diluted with ethyl acetate. This mixture was washed with brine. The resulting organic layer was dried and concentrated in vacuo. This alcohol compound was dissolved in methylene chloride (50 ml) and was slowly added methanesulfonic acid (20 mmol) and sodium cyanate (20 mmol) at 0° C. After 5 hr stirring at room temperature, brine was added to terminate the reaction. The resulting organic layer was dried and concentrated in vacuo. The residue was purified by column chromatography (ethyl acetate:hexane=1:1) to give O-1-(2-Chloro-phenyl)-2-tetrazol-2-yl ethyl allophanate.

¹H-NMR (DMSO-d₆) δ8.75(s, 1H), 8.11(s, 1H), 748(m, 3H), 6.67(m, 1H), 5.59-6.55(br, 2H), 5.46(m, 2H).

| # | Structure | IUPAC |
|---|---|---|
| 1 | 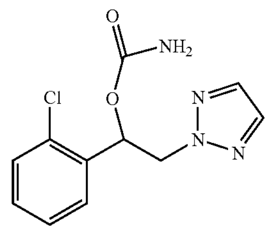 | Carbamic acid 1-(2-chloro-phenyl)-2-[1,2,3]triazol-2-yl-ethyl ester |
| 2 | 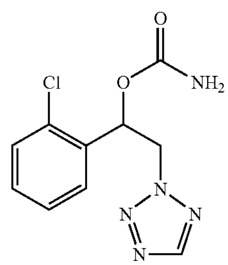 | Carbamic acid 1-(2-chloro-phenyl)-2-tetrazol-2-yl-ethyl ester |
| 3 | 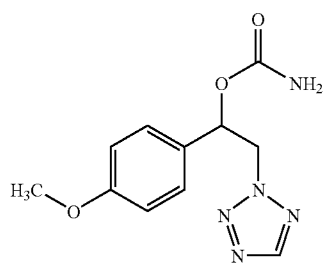 | Carbamic acid 1-(4-methoxy-phenyl)-2-tetrazol-2-yl-ethyl ester |
| 4 | 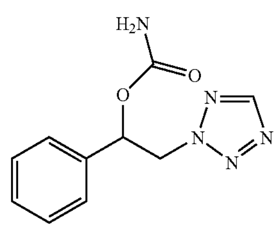 | Carbamic acid 1-phenyl-2-tetrazol-2-yl-ethyl ester |
| 5 | 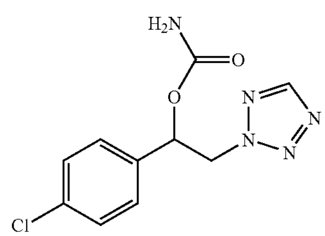 | Carbamic acid 1-(4-chloro-phenyl)-2-tetrazol-2-yl-ethyl ester |
| 6 | 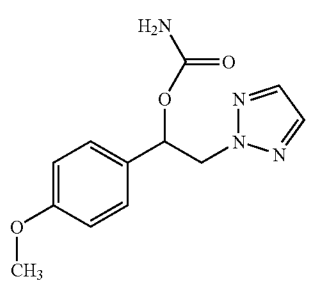 | Carbamic acid 1-(4-methoxy-phenyl)-2-[1,2,3]triazol-2-yl-ethyl ester |

-continued
| # | Structure | IUPAC |
|---|---|---|
| 7 | 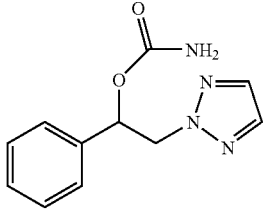 | Carbamic acid 1-phenyl-2-[1,2,3]triazol-2-yl-ethyl ester |
| 8 | 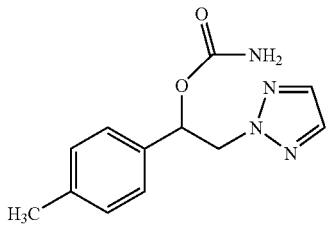 | Carbamic acid 1-p-tolyl-2-[1,2,3]triazol-2-yl-ethyl ester |
| 9 | 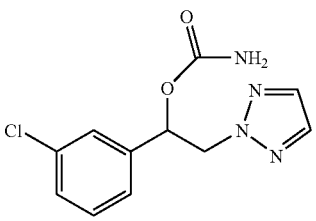 | Carbamic acid 1-(3-chloro-phenyl)-2-[1,2,3]triazol-2-yl-ethyl ester |
| 10 | 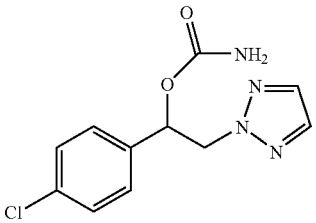 | Carbamic acid 1-(4-chloro-phenyl)-2-[1,2,3]triazol-2-yl-ethyl ester |
| 11 | 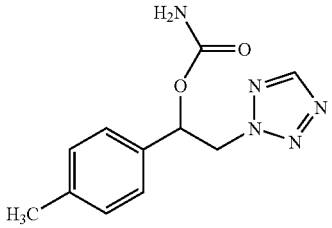 | Carbamic acid 2-tetrazol-2-yl-1-p-tolyl-ethyl ester |
| 12 | 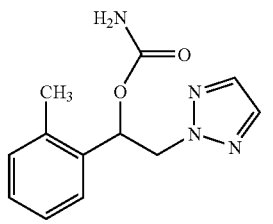 | Carbamic acid 1-o-tolyl-2-[1,2,3]triazol-2-yl-ethyl ester |

| # | Structure | IUPAC |
|---|---|---|
| 13 | 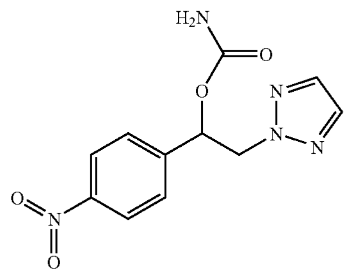 | Carbamic acid 1-(4-nitro-phenyl)-2-[1,2,3]triazol-2-yl-ethyl ester |
| 14 | 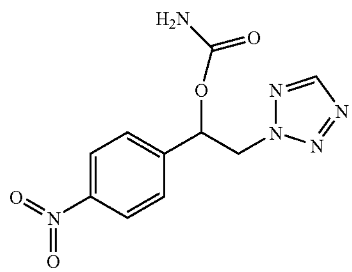 | Carbamic acid 1-(4-nitro-phenyl)-2-tetrazol-2-yl-ethyl ester |
| 15 | 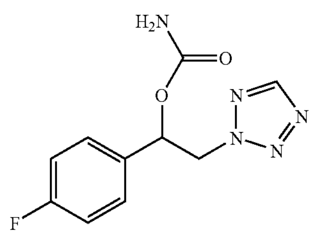 | Carbamic acid 1-(4-fluoro-phenyl)-2-tetrazol-2-yl-ethyl ester |
| 16 | 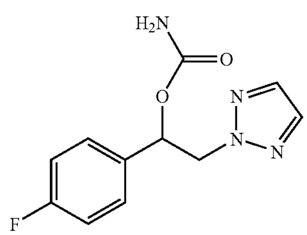 | Carbamic acid 1-(4-fluoro-phenyl)-2-[1,2,3]triazol-2-yl-ethyl ester |
| 17 | 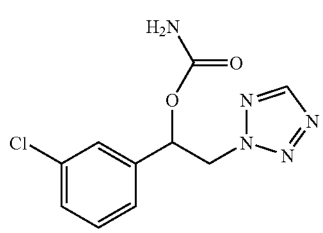 | Carbamic acid 1-(3-chloro-phenyl)-2-tetrazol-2-yl-ethyl ester |
| 18 | 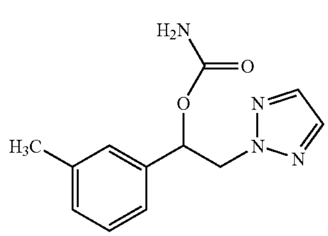 | Carbamic acid 1-m-tolyl-2-[1,2,3]triazol-2-yl-ethyl ester |

| # | Structure | IUPAC |
|---|---|---|
| 19 | 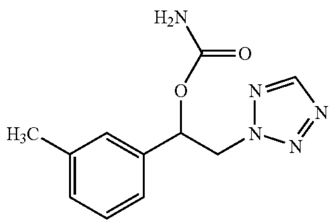 | Carbamic acid 2-tetrazol-2-yl-1-m-tolyl-ethyl ester |
| 20 | Chiral | Carbamic acid (R)-1-(2-chloro-phenyl)-2-tetrazol-2-yl-ethyl ester |
| 21 | Chiral | Carbamic acid (S)-1-(2-chloro-phenyl)-2-tetrazol-2-yl-ethyl ester |
| 22 | Chiral | Carbamic acid (R)-1-(2-chloro-phenyl)-2-tetrazol-1-yl-ethyl ester |
| 23 | Chiral | Carbamic acid (S)-1-(2-chloro-phenyl)-2-tetrazol-1-yl-ethyl ester |
| 24 | 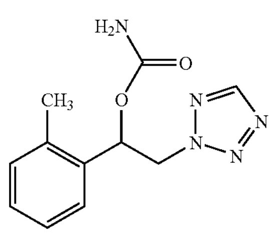 | Carbamic acid 2-tetrazol-2-yl-1-o-tolyl-ethyl ester |

-continued

| # | Structure | IUPAC |
|---|---|---|
| 25 | 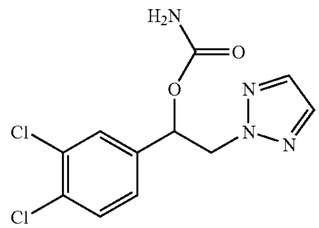 | Carbamic acid 1-(3,4-dichloro-phenyl)-2-[1,2,3]triazol-2-yl-ethyl ester |
| 26 | 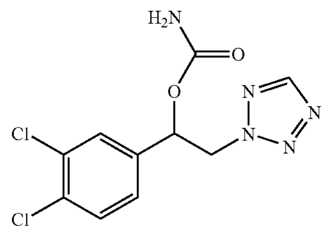 | Carbamic acid 1-(3,4-dichloro-phenyl)-2-tetrazol-2-yl-ethyl ester |
| 27 | 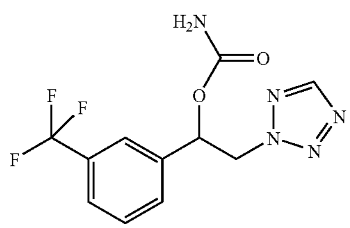 | Carbamic acid 2-tetrazol-2-yl-1-(3-trifluoromethyl-phenyl)-ethyl ester |
| 28 | 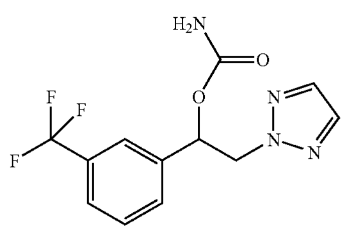 | Carbamic acid 2-[1,2,3]triazol-2-yl-1-(3-trifluoromethyl-phenyl)-ethyl ester |
| 29 | 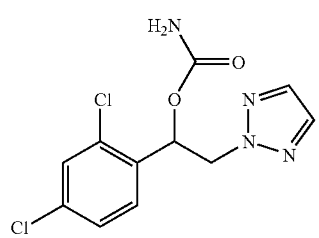 | Carbamic acid 1-(2,4-dichloro-phenyl)-2-[1,2,3]triazol-2-yl-ethyl ester |
| 30 | 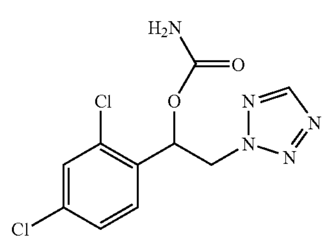 | Carbamic acid 1-(2,4-dichloro-phenyl)-2-tetrazol-2-yl-ethyl ester |

| # | Structure | IUPAC |
|---|---|---|
| 31 | 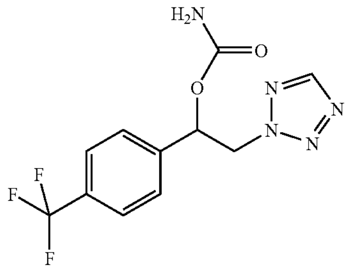 | Carbamic acid 2-tetrazol-2-yl-1-(4-trifluoromethyl-phenyl)-ethyl ester |
| 32 | 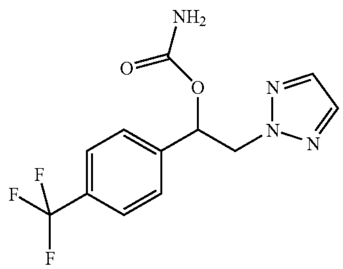 | Carbamic acid 2-[1,2,3]triazol-2-yl-1-(4-trifluoromethyl-phenyl)-ethyl ester |
| 33 | Chiral | Carbamic acid (R)-1-(2-chloro-phenyl)-2-[1,2,3]triazol-2-yl-ethyl ester |
| 34 | Chiral | Carbamic acid (S)-1-(2-chloro-phenyl)-2-[1,2,3]triazol-2-yl-ethyl ester |
| 35 | 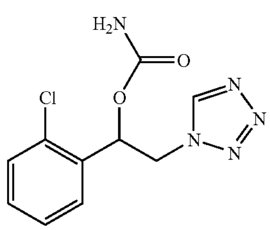 | Carbamic acid 1-(2-chloro-phenyl)-2-tetrazol-1-yl-ethyl ester |
| 36 | Chiral | Carbamic acid (R)-1-(2-chloro-phenyl)-2-[1,2,3]triazol-1-yl-ethyl ester |

-continued

| # | Structure | IUPAC |
|---|---|---|
| 37 | 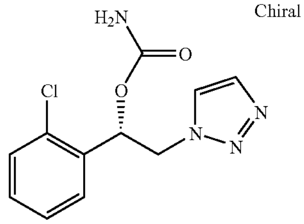 | Carbamic acid (S)-1-(2-chloro-phenyl)-2-[1,2,3]triazol-1-yl-ethyl ester |
| 38 | 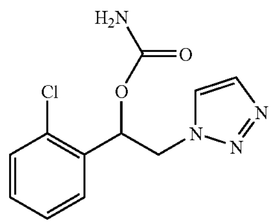 | Carbamic acid 1-(2-chloro-phenyl)-2-[1,2,3]triazol-1-yl-ethyl ester |
| 39 | 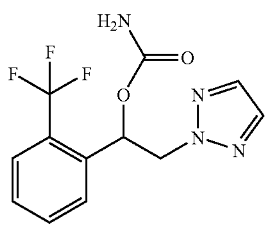 | Carbamic acid 2-[1,2,3]triazol-2-yl-1-(2-trifluoromethyl-phenyl)-ethyl ester |
| 40 | 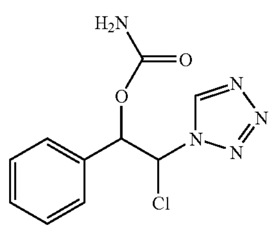 | Carbamic acid 2-chloro-1-phenyl-2-tetrazol-1-yl-ethyl ester |
| 41 | 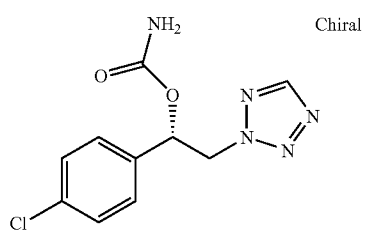 | Carbamic acid (S)-1-(4-chloro-phenyl)-2-tetrazol-2-yl-ethyl ester |
| 42 | 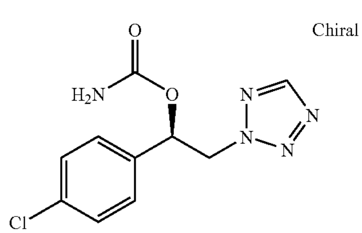 | Carbamic acid (R)-1-(4-chloro-phenyl)-2-tetrazol-2-yl-ethyl ester |

| # | Structure | IUPAC |
|---|---|---|
| 43 | 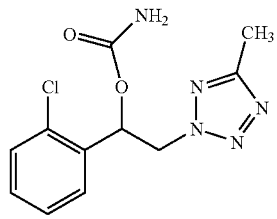 | Carbamic acid 1-(2-chloro-phenyl)-2-(5-methyl-tetrazol-2-yl)-ethyl ester |
| 44 | 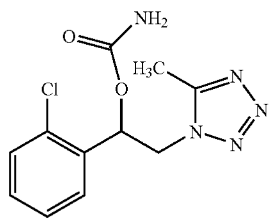 | Carbamic acid 1-(2-chloro-phenyl)-2-(5-methyl-tetrazol-1-yl)-ethyl ester |
| 45 | 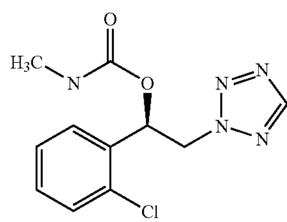 | Methyl-carbamic acid (R)-1-(2-chloro-phenyl)-2-tetrazol-2-yl-ethyl ester |
| 46 | 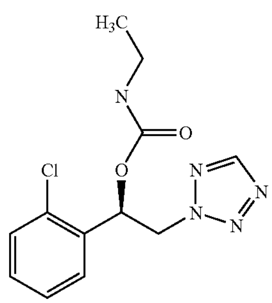 | Ethyl-carbamic acid (R)-1-(2-chloro-phenyl)-2-tetrazol-2-yl-ethyl ester |
| 47 | 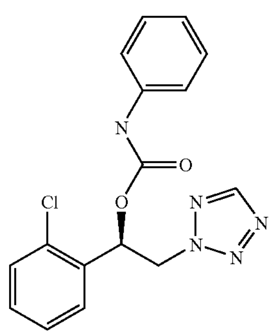 | Phenyl-carbamic acid (R)-1-(2-chloro-phenyl)-2-tetrazol-2-yl-ethyl ester |
| 48 | 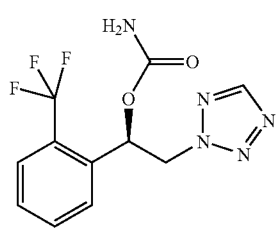 | Carbamic acid (R)-2-tetrazol-2-yl-1-(2-trifluoromethyl-phenyl)-ethyl ester |

-continued

| # | Structure | IUPAC |
|---|---|---|
| 49 | 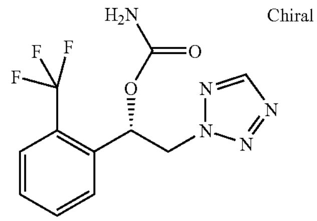 | Carbamic acid (S)-2-tetrazol-2-yl-1-(2-trifluoromethyl-phenyl)-ethyl ester |
| 50 | 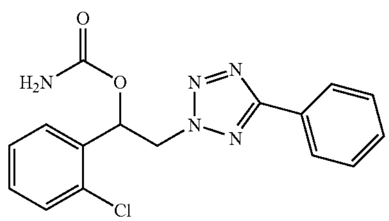 | Carbamic acid 1-(2-chloro-phenyl)-2-(5-phenyl-tetrazol-2-yl)-ethyl ester |
| 51 | 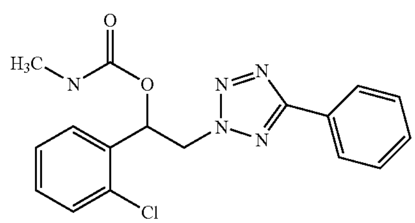 | Methyl-carbamic acid 1-(2-chloro-phenyl)-2-(5-phenyl-tetrazol-2-yl)-ethyl ester |
| 52 | 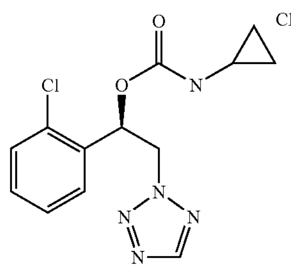 | Cyclopropyl-carbamic acid (R)-1-(2-chloro-phenyl)-2-tetrazol-2-yl-ethyl ester |
| 53 | 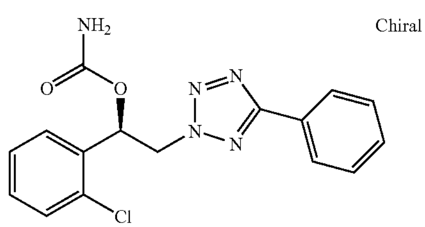 | Carbamic acid (R)-1-(2-chloro-phenyl)-2-(5-phenyl-tetrazol-2-yl)-ethyl ester |
| 54 | 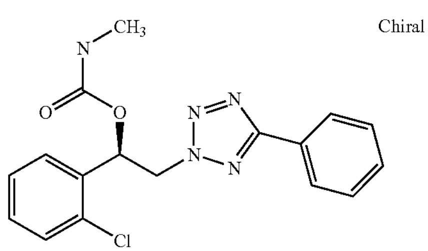 | Methyl-carbamic acid (R)-1-(2-chloro-phenyl)-2-(5-phenyl-tetrazol-2-yl)-ethyl ester |

-continued

| # | Structure | IUPAC |
|---|---|---|
| 55 | 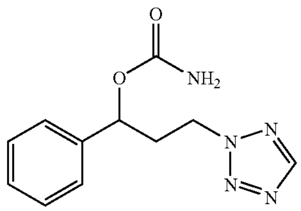 | Carbamic acid 1-phenyl-3-tetrazol-2-yl-propyl ester |
| 56 | 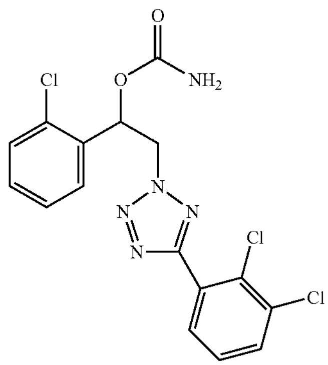 | Carbamic acid 1-(2-chloro-phenyl)-2-[5-(2,3-dichloro-phenyl)-tetrazol-2-yl]-ethyl ester |
| 57 | 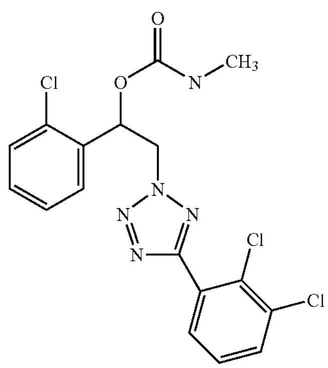 | Methyl-carbamic acid 1-(2-chloro-phenyl)-2-[5-(2,3-dichloro-phenyl)-tetrazol-2-yl]-ethyl ester |
| 58 | 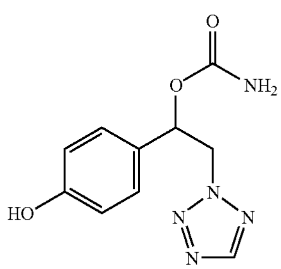 | Carbamic acid 1-(4-hydroxy-phenyl)-2-tetrazol-2-yl-ethyl ester |
| 59 | Chiral | Carbamic acid (S)-1-(2-chloro-phenyl)-2-(5-phenyl-tetrazol-2-yl)-ethyl ester |

| # | Structure | | IUPAC |
|---|---|---|---|
| 60 | 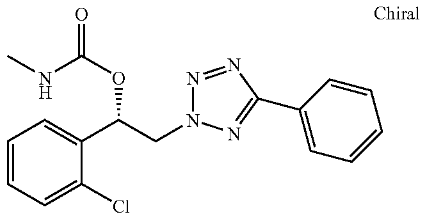 | Chiral | Methyl-carbamic acid (S)-1-(2-chloro-phenyl)-2-(5-phenyl-tetrazol-2-yl)-ethyl ester |
| 61 | 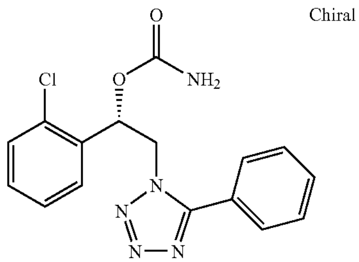 | Chiral | Carbamic acid (S)-1-(2-chloro-phenyl)-2-(5-phenyl-tetrazol-1-yl)-ethyl ester |
| 62 | 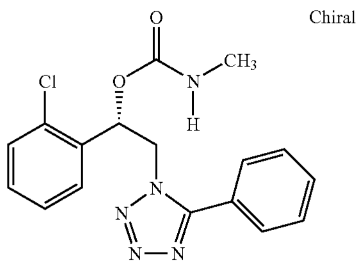 | Chiral | Methyl-carbamic acid (S)-1-(2-chloro-phenyl)-2-(5-phenyl-tetrazol-1-yl)-ethyl ester |
| 63 | 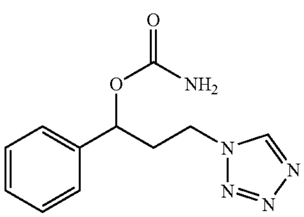 | | Carbamic acid 1-phenyl-3-tetrazol-1-yl-propyl ester |
| 64 | 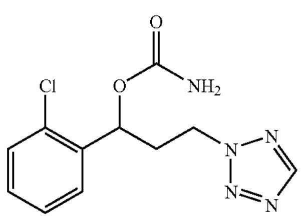 | | Carbamic acid 1-phenyl-3-tetrazol-1-yl-propyl ester |
| 65 | 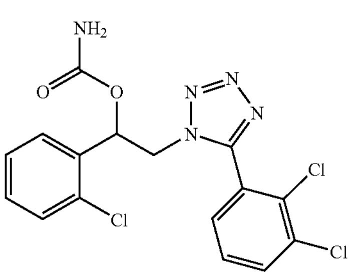 | | Carbamic acid 1-(2-chloro-phenyl)-2-[5-(2,3-dichloro-phenyl)-tetrazol-1-yl]-ethyl ester |

| # | Structure | IUPAC |
|---|---|---|
| 66 | 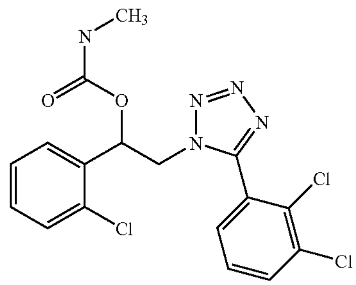 | Methyl-carbamic acid 1-(2-chloro-phenyl)-2-[5-(2,3-dichloro-phenyl)-tetrazol-1-yl]-ethyl ester |
| 67 | 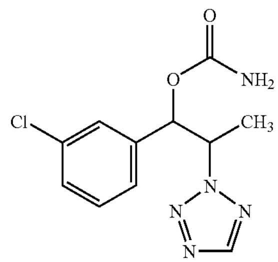 | Carbamic acid 1-(3-chloro-phenyl)-2-tetrazol-2-yl-propyl ester |
| 68 | 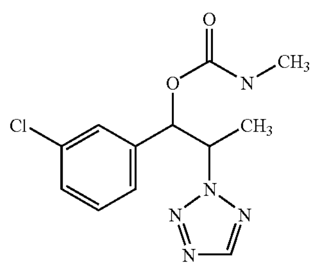 | Methyl-carbamic acid 1-(3-chloro-phenyl)-2-tetrazol-2-yl-propyl ester |
| 69 | 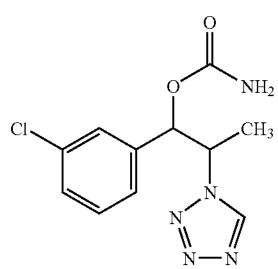 | Carbamic acid 1-(3-chloro-phenyl)-2-tetrazol-1-yl-propyl ester |
| 70 | 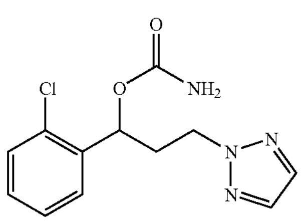 | Carbamic acid 1-(2-chloro-phenyl)-3-[1,2,3]triazol-2-yl-propyl ester |
| 71 | 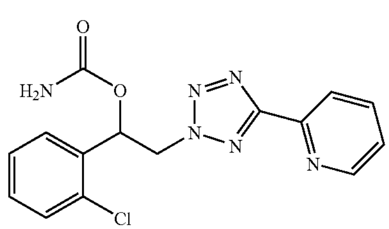 | Carbamic acid 1-(2-chloro-phenyl)-2-(5-pyridin-2-yl-tetrazol-2-yl)-ethyl ester |

| # | Structure | IUPAC |
|---|---|---|
| 72 | 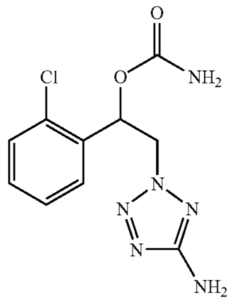 | Carbamic acid 2-(5-amino-tetrazol-2-yl)-1-(2-chloro-phenyl)-ethyl ester |
| 73 | 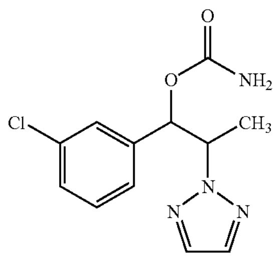 | Carbamic acid 1-(3-chloro-phenyl)-2-[1,2,3]triazol-2-yl-propyl ester |
| 74 | 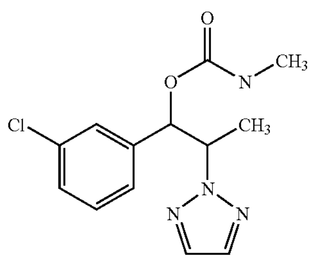 | Methyl-carbamic acid 1-(3-chloro-phenyl)-2-[1,2,3]triazol-2-yl-propyl ester |
| 75 | 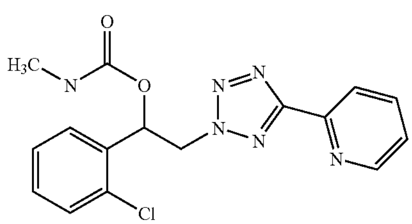 | Ethyl-carbamic acid 1-(2-chloro-phenyl)-2-(5-pyridin-2-yl-tetrazol-2-yl)-ethyl ester |
| 76 | 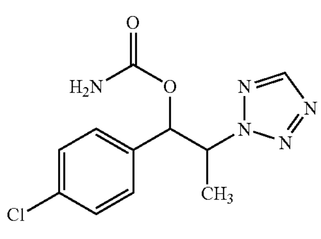 | Carbamic acid 1-(4-chloro-phenyl)-2-tetrazol-2-yl-propyl ester |
| 77 | 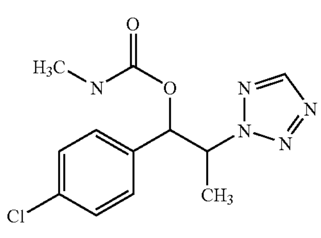 | Methyl-carbamic acid 1-(4-chloro-phenyl)-2-tetrazol-2-yl-propyl ester |

| # | Structure | IUPAC |
|---|---|---|
| 78 | 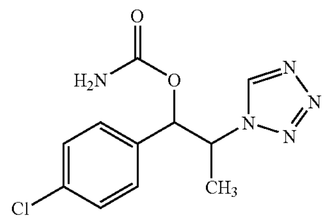 | Carbamic acid 1-(4-chloro-phenyl)-2-tetrazol-1-yl-propyl ester |
| 79 | 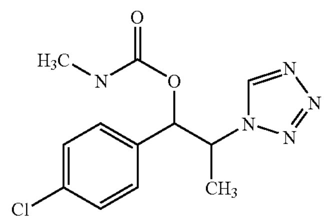 | Methyl-carbamic acid 1-(4-chloro-phenyl)-2-tetrazol-1-yl-propyl ester |
| 80 | 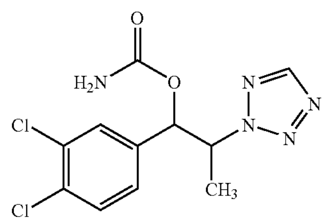 | Carbamic acid 1-(3,4-dichloro-phenyl)-2-tetrazol-2-yl-propyl ester |
| 81 | 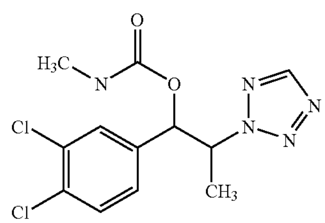 | Methyl-carbamic acid 1-(3,4-dichloro-phenyl)-2-tetrazol-2-yl-propyl ester |
| 82 | 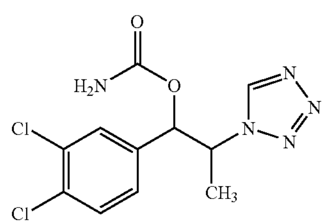 | Carbamic acid 1-(3,4-dichloro-phenyl)-2-tetrazol-1-yl-propyl ester |
| 83 | 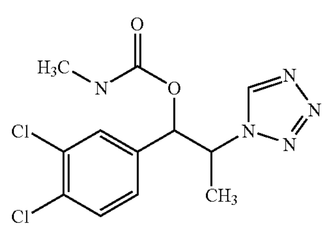 | Methyl-carbamic acid 1-(3,4-dichloro-phenyl)-2-tetrazol-1-yl-propyl ester |
| 84 | 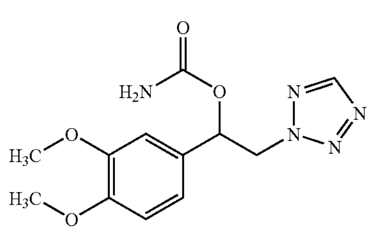 | Carbamic acid 1-(3,4-dimethoxy-phenyl)-2-tetrazol-2-yl-ethyl ester |

| # | Structure | IUPAC |
|---|---|---|
| 85 | 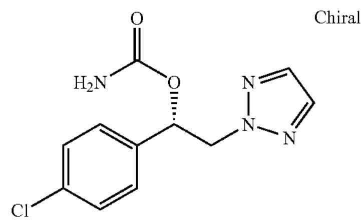 | Carbamic acid (S)-1-(4-chloro-phenyl)-2-[1,2,3]triazol-2-yl-ethyl ester |
| 86 | 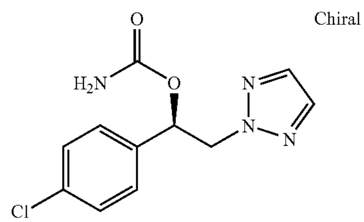 | Carbamic acid (R)-1-(4-chloro-phenyl)-2-[1,2,3]triazol-2-yl-ethyl ester |
| 87 | 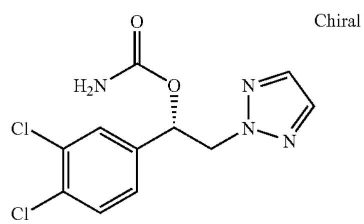 | Carbamic acid (S)-1-(3,4-dichloro-phenyl)-2-[1,2,3]triazol-2-yl-ethyl ester |
| 88 | 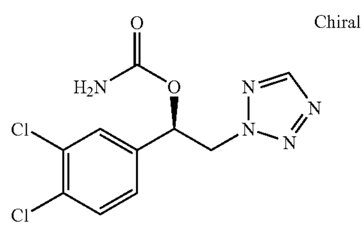 | Carbamic acid (R)-1-(3,4-dichloro-phenyl)-2-tetrazol-2-yl-ethyl ester |
| 89 | 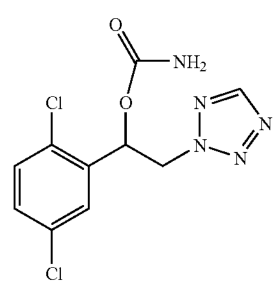 | Carbamic acid 1-(2,5-dichloro-phenyl)-2-tetrazol-2-yl-ethyl ester |
| 90 | 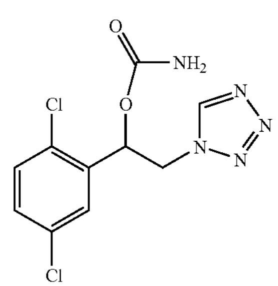 | Carbamic acid 1-(2,5-dichloro-phenyl)-2-tetrazol-1-yl-ethyl ester |

-continued

| # | Structure | IUPAC |
|---|-----------|-------|
| 91 | Chiral | Carbamic acid (R)-1-(3,4-dichloro-phenyl)-2-[1,2,3]triazol-2-yl-ethyl ester |
| 92 | Chiral | Carbamic acid (R)-1-(3,4-dichloro-phenyl)-2-[1,2,3]triazol-1-yl-ethyl ester |
| 93 | 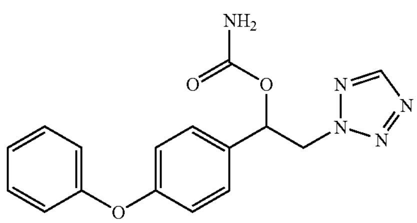 | Carbamic acid 1-(4-phenoxy-phenyl)-2-tetrazol-2-yl-ethyl ester |
| 94 | 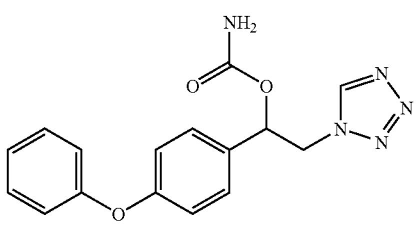 | Carbamic acid 1-(4-phenoxy-phenyl)-2-tetrazol-1-yl-ethyl ester |
| 95 | 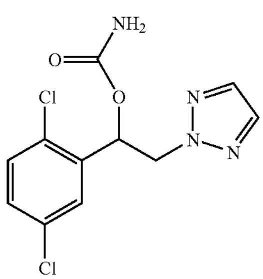 | Carbamic acid 1-(2,5-dichloro-phenyl)-2-[1,2,3]triazol-2-yl-ethyl ester |
| 96 | Chiral | Carbamic acid (S)-1-(3,4-dichloro-phenyl)-2-tetrazol-2-yl-ethyl ester |

| # | Structure | IUPAC |
|---|---|---|
| 97 | 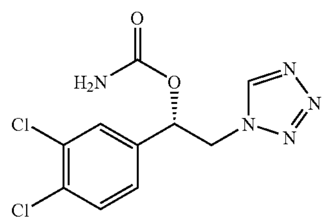 | Carbamic acid (S)-1-(3,4-dichloro-phenyl)-2-tetrazol-1-yl-ethyl ester |
| 98 | 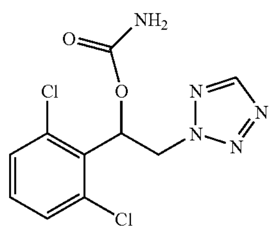 | Carbamic acid 1-(2,6-dichloro-phenyl)-2-tetrazol-2-yl-ethyl ester |
| 99 | 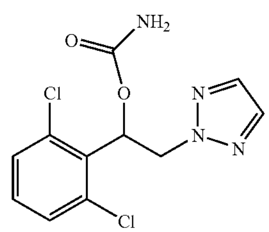 | Carbamic acid 1-(2,6-dichloro-phenyl)-2-[1,2,3]triazol-2-yl-ethyl ester |
| 100 | 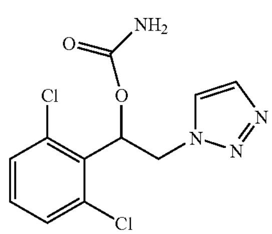 | Carbamic acid 1-(2,6-dichloro-phenyl)-2-[1,2,3]triazol-1-yl-ethyl ester |
| 101 | 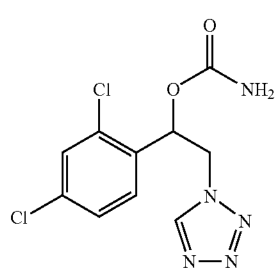 | Carbamic acid 1-(2,4-dichloro-phenyl)-2-tetrazol-1-yl-ethyl ester |
| 102 | 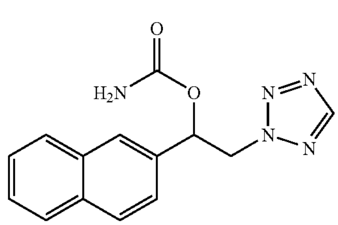 | Carbamic acid 1-naphthalen-2-yl-2-tetrazol-2-yl-ethyl ester |

-continued

| # | Structure | IUPAC |
|---|---|---|
| 103 | Chiral | Carbamic acid (R)-1-(2,4-dichloro-phenyl)-2-tetrazol-2-yl-ethyl ester |
| 104 | 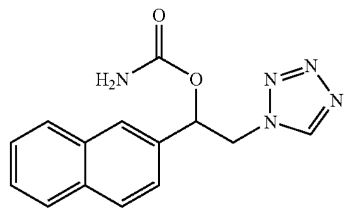 | Carbamic acid 1-naphthalen-2-yl-2-tetrazol-1-yl-ethyl ester |
| 105 | 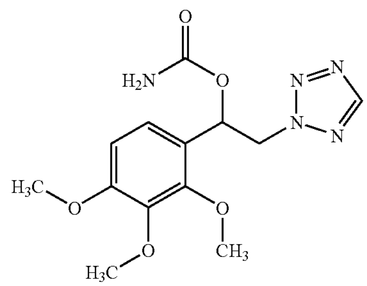 | Carbamic acid 2-tetrazol-2-yl-1-(2,3,4-trimethoxy-phenyl)-ethyl ester |
| 106 | 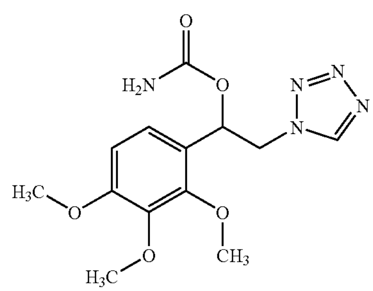 | Carbamic acid 2-tetrazol-1-yl-1-(2,3,4-trimethoxy-phenyl)-ethyl ester |
| 107 | 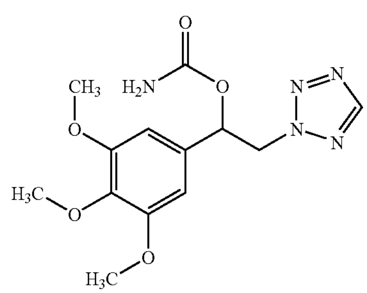 | Carbamic acid 2-tetrazol-2-yl-1-(3,4,5-trimethoxy-phenyl)-ethyl ester |
| 108 | 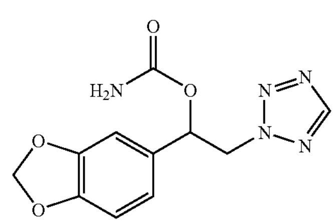 | Carbamic acid 1-benzo[1,3]dioxol-5-yl-2-tetrazol-2-yl-ethyl ester |

-continued

| # | Structure | IUPAC |
|---|---|---|
| 109 | 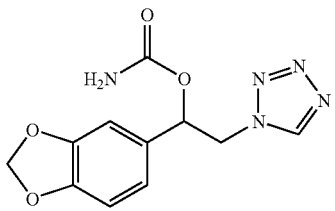 | Carbamic acid 1-benzo[1,3]dioxol-5-yl-2-tetrazol-1-yl-ethyl ester |
| 110 | 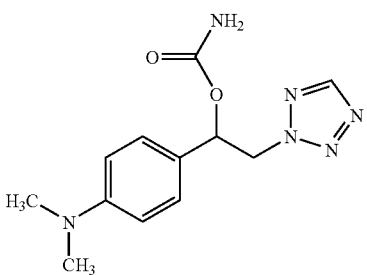 | Carbamic acid 1-(4-dimethylamino-phenyl)-2-tetrazol-2-yl-ethyl ester |
| 111 | 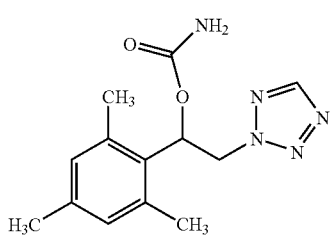 | Carbamic acid 2-tetrazol-2-yl-1-(2,4,6-trimethyl-phenyl)-ethyl ester |
| 112 | 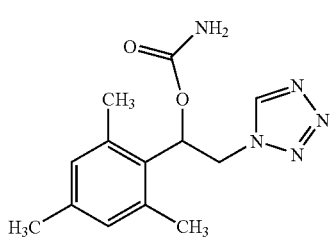 | Carbamic acid 2-tetrazol-1-yl-1-(2,4,6-trimethyl-phenyl)-ethyl ester |
| 113 | 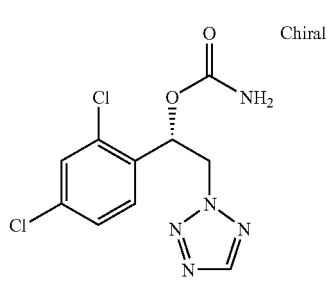 | Carbamic acid (S)-1-(2,4-dichloro-phenyl)-2-tetrazol-2-yl-ethyl ester |
| 114 | 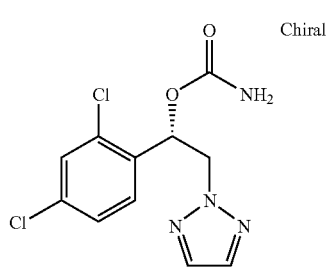 | Carbamic acid (S)-1-(2,4-dichloro-phenyl)-2-[1,2,3]triazol-2-yl-ethyl ester |

-continued

| # | Structure | IUPAC |
|---|---|---|
| 115 | 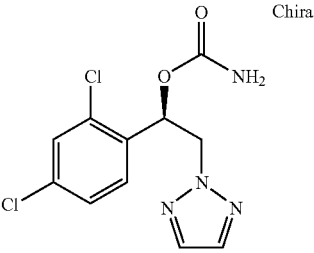 | Carbamic acid (R)-1-(2,4-dichloro-phenyl)-2-[1,2,3]triazol-2-yl-ethyl ester |
| 116 | 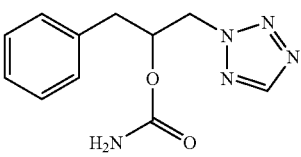 | Carbamic acid 2-phenyl-1-tetrazol-2-ylmethyl-ethyl ester |
| 117 | 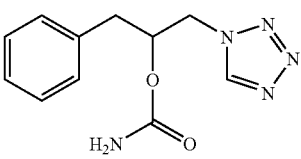 | Carbamic acid 2-phenyl-1-tetrazol-1-ylmethyl-ethyl ester |
| 118 | 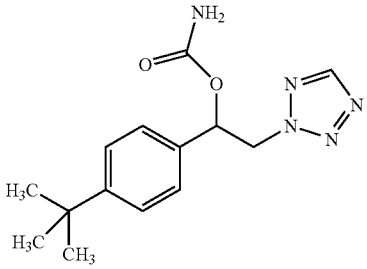 | Carbamic acid 1-(4-tert-butyl-phenyl)-2-tetrazol-2-yl-ethyl ester |
| 119 | 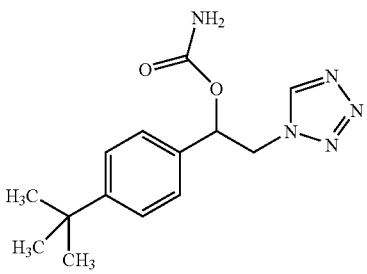 | Carbamic acid 1-(4-tert-butyl-phenyl)-2-tetrazol-1-yl-ethyl ester |
| 120 | 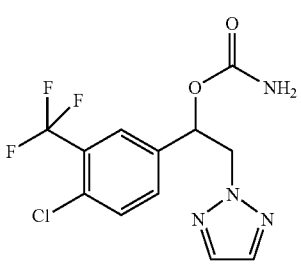 | Carbamic acid 1-(4-chloro-3-trifluoromethyl-phenyl)-2-[1,2,3]triazol-2-yl-ethyl ester |

-continued

| # | Structure | IUPAC |
|---|---|---|
| 121 | 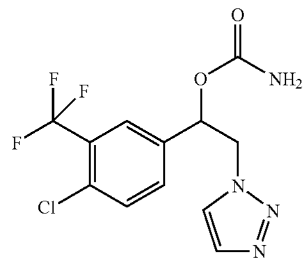 | Carbamic acid 1-(4-chloro-3-trifluoromethyl-phenyl)-2-[1,2,3]triazol-1-yl-ethyl ester |
| 122 | Chiral | Carbamic acid (S)-1-(2,6-dichloro-phenyl)-2-tetrazol-1-yl-ethyl ester |
| 123 | Chiral | Carbamic acid (R)-1-(2,6-dichloro-phenyl)-2-tetrazol-1-yl-ethyl ester |
| 124 | 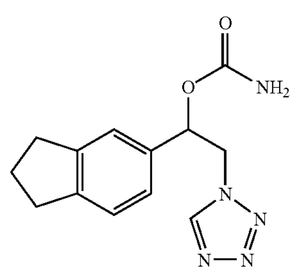 | Carbamic acid 1-indan-5-yl-2-tetrazol-1-yl-ethyl ester |
| 125 | 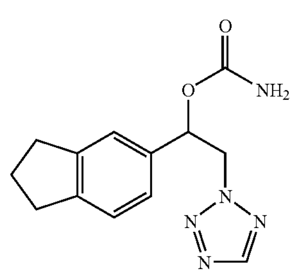 | Carbamic acid 1-indan-5-yl-2-tetrazol-2-yl-ethyl ester |
| 126 | Chiral | Carbamic acid (R)-1-(2,6-dichloro-phenyl)-2-tetrazol-2-yl-ethyl ester |

-continued

| # | Structure | IUPAC |
|---|---|---|
| 127 | 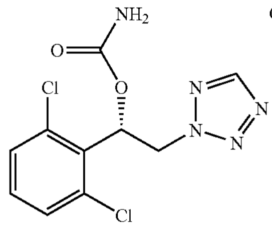 | Carbamic acid (S)-1-(2,6-dichloro-phenyl)-2-tetrazol-2-yl-ethyl ester |
| 128 | 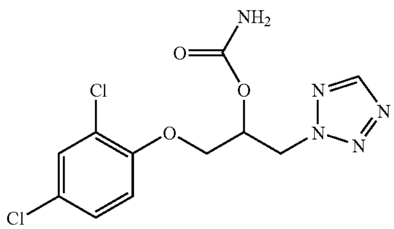 | Carbamic acid 2-(2,4-dichloro-phenoxy)-1-tetrazol-2-ylmethyl-ethyl ester |
| 129 | 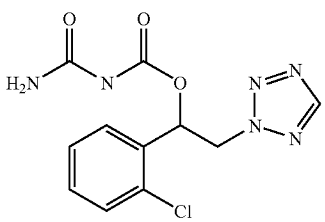 | O-1-(2-Chloro-phenyl)-2-tetrazol-2-yl ethyl allophanate |
| 130 | 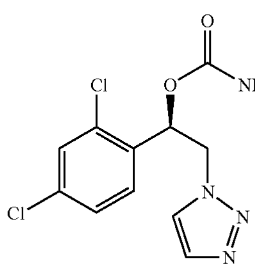 | Carbamic acid (R)-1-(2,4-dichloro-phenyl)-2-[1,2,3]triazol-1-yl-ethyl ester |
| 131 | 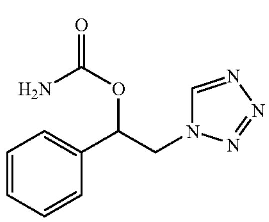 | Carbamic acid 1-phenyl-2-tetrazol-1-yl-ethyl ester |
| 132 | 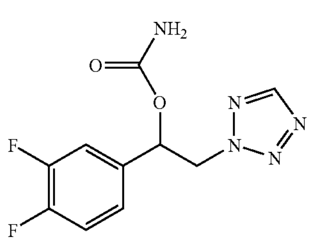 | Carbamic acid 1-(3,4-difluoro-phenyl)-2-tetrazol-2-yl-ethyl ester |

-continued

| # | Structure | IUPAC |
|---|---|---|
| 133 | 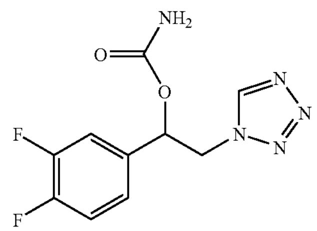 | Carbamic acid 1-(3,4-difluoro-phenyl)-2-tetrazol-1-yl-ethyl ester |
| 134 | 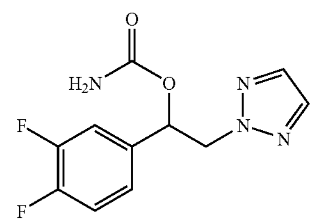 | Carbamic acid 1-(3,4-difluoro-phenyl)-2-[1,2,3]triazol-2-yl-ethyl ester |
| 135 | 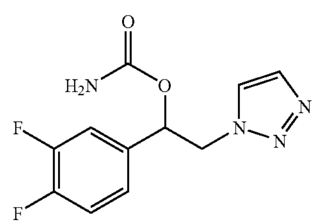 | Carbamic acid 1-(3,4-difluoro-phenyl)-2-[1,2,3]triazol-1-yl-ethyl ester |
| 136 | 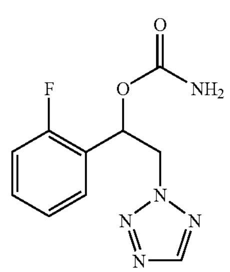 | Carbamic acid 1-(2-fluoro-phenyl)-2-tetrazol-2-yl-ethyl ester |
| 137 | 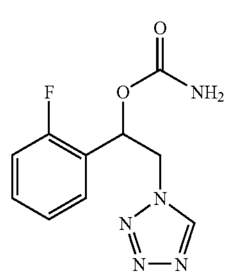 | Carbamic acid 1-(2-fluoro-phenyl)-2-tetrazol-1-yl-ethyl ester |

-continued

| # | Structure | IUPAC |
|---|---|---|
| 138 | 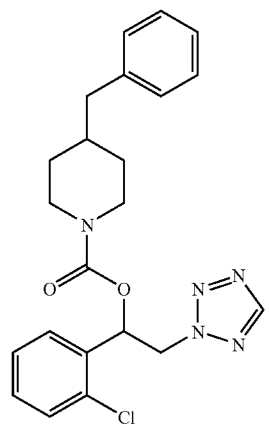 | 4-Benzyl-piperidine-1-carboxylic acid 1-(2-chloro-phenyl)-2-tetrazol-2-yl-ethyl ester |
| 139 | 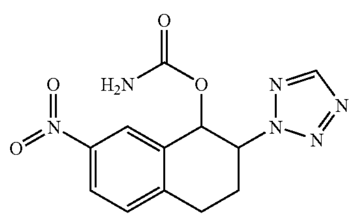 | Carbamic acid 7-nitro-2-tetrazol-2-yl-1,2,3,4-tetrahydro-naphthalen-1-yl ester |
| 140 | 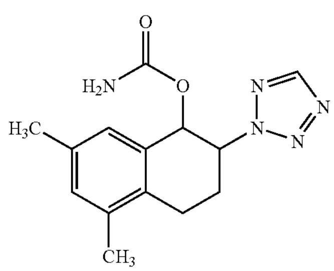 | Carbamic acid 5,7-dimethyl-2-tetrazol-2-yl-1,2,3,4-tetrahydro-naphthalen-1-yl ester |
| 141 | 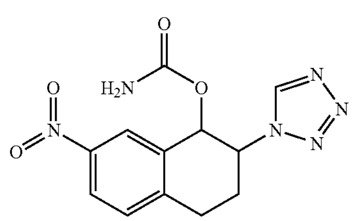 | Carbamic acid 7-nitro-2-tetrazol-1-yl-1,2,3,4-tetrahydro-naphthalen-1-yl ester |
| 142 | 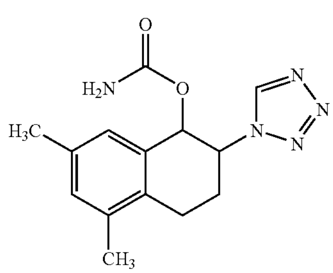 | Carbamic acid 5,7-dimethyl-2-tetrazol-1-yl-1,2,3,4-tetrahydro-naphthalen-1-yl ester |

-continued

| # | Structure | IUPAC |
|---|---|---|
| 143 | 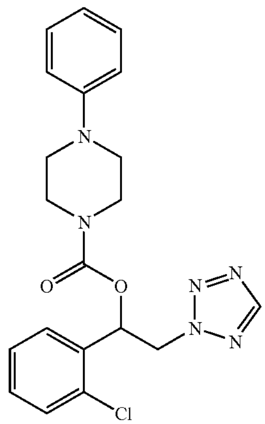 | 4-Phenyl-piperazine-1-carboxylic acid 1-(2-chloro-phenyl)-2-tetrazol-2-yl-ethyl ester |
| 144 | 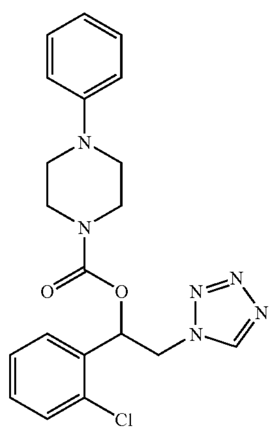 | 4-Phenyl-piperazine-1-carboxylic acid 1-(2-chloro-phenyl)-2-tetrazol-1-yl-ethyl ester |
| 145 | 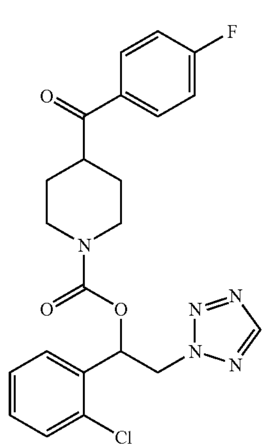 | 4-(4-Fluoro-benzoyl)-piperidine-1-carboxylic acid 1-(2-chloro-phenyl)-2-tetrazol-2-yl-ethyl ester |

-continued

| # | Structure | IUPAC |
|---|---|---|
| 146 | 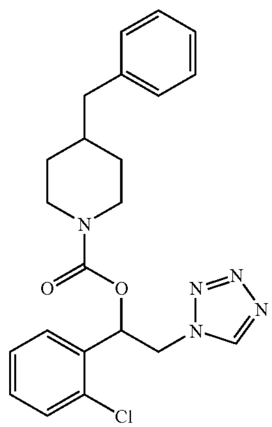 | 4-Benzyl-piperidine-1-carboxylic acid 1-(2-chloro-phenyl)-2-tetrazol-1-yl-ethyl ester |
| 147 | 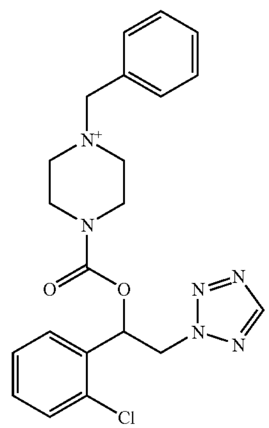 | 1-Benzyl-4-[1-(2-chloro-phenyl)-2-tetrazol-2-yl-ethoxycarbonyl]-piperazin-1-ium |
| 148 | 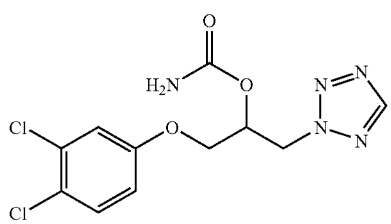 | Carbamic acid 2-(3,4-dichloro-phenoxy)-1-tetrazol-2-ylmethyl-ethyl ester |
| 149 | 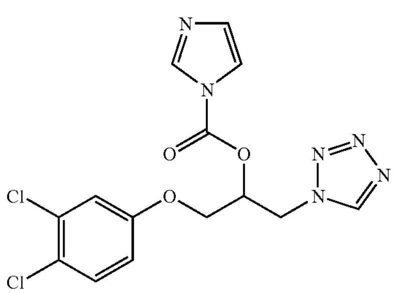 | Imidazole-1-carboxylic acid 2-(3,4-dichloro-phenoxy)-1-tetrazol-1-ylmethyl-ethyl ester |
| 150 | 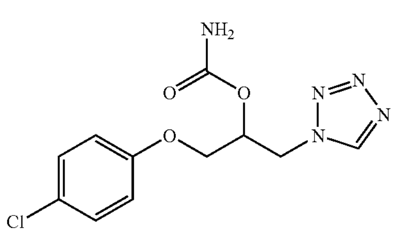 | Carbamic acid 2-(4-chloro-phenoxy)-1-tetrazol-1-ylmethyl-ethyl ester |

-continued

| # | Structure | IUPAC |
|---|---|---|
| 151 | 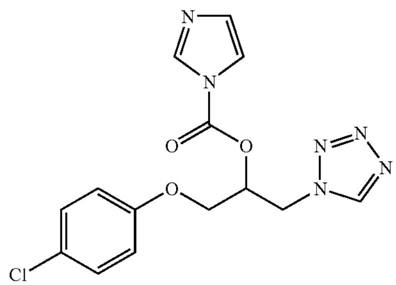 | Imidazole-1-carboxylic acid 2-(4-chloro-phenoxy)-1-tetrazol-1-ylmethyl-ethyl ester |
| 152 | 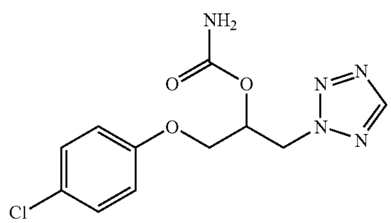 | Carbamic acid 2-(4-chloro-phenoxy)-1-tetrazol-2-ylmethyl-ethyl ester |
| 153 | 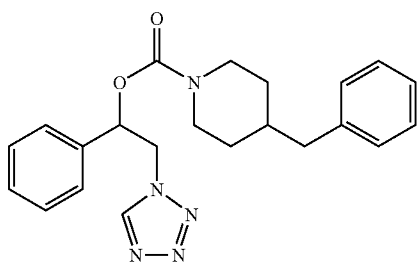 | 4-Benzyl-piperidine-1-carboxylic acid 1-phenyl-2-tetrazol-1-yl-ethyl ester |
| 154 | 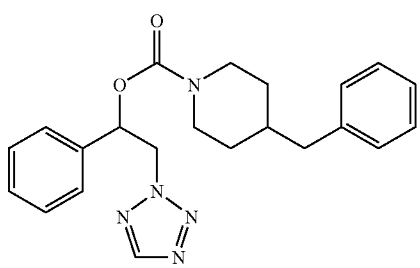 | 4-Benzyl-piperidine-1-carboxylic acid 1-phenyl-2-tetrazol-2-yl-ethyl ester |
| 155 | 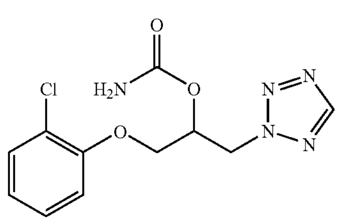 | Carbamic acid 2-(2-chloro-phenoxy)-1-tetrazol-2-ylmethyl-ethyl ester |
| 156 | 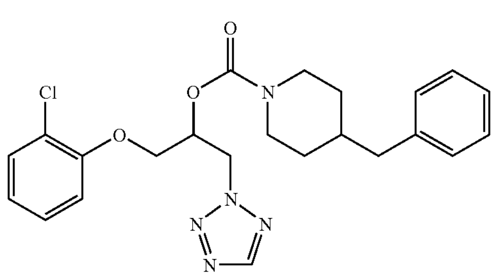 | 4-Benzyl-piperidine-1-carboxylic acid 2-(2-chloro-phenoxy)-1-tetrazol-2-ylmethyl-ethyl ester |

-continued

| # | Structure | IUPAC |
| --- | --- | --- |
| 157 | 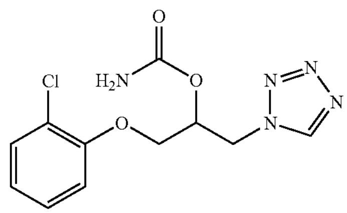 | Carbamic acid 2-(2-chloro-phenoxy)-1-tetrazol-1-ylmethyl-ethyl ester |
| 158 | 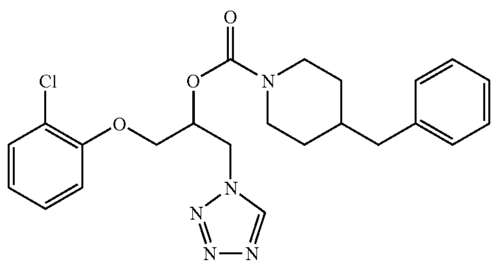 | 4-Benzyl-piperidine-1-carboxylic acid 2-(2-chloro-phenoxy)-1-tetrazol-1-ylmethyl-ethyl ester |
| 159 | 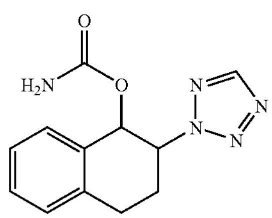 | Carbamic acid 2-tetrazol-2-yl-1,2,3,4-tetrahydro-naphthalen-1-yl ester |
| 160 | 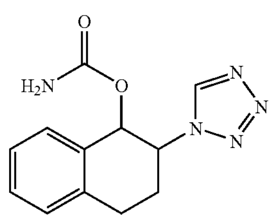 | Carbamic acid 2-tetrazol-1-yl-1,2,3,4-tetrahydro-naphthalen-1-yl ester |
| 161 | 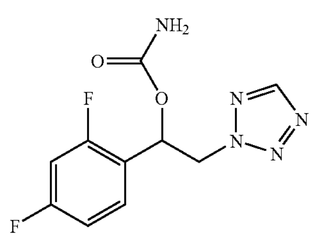 | Carbamic acid 1-(2,4-difluoro-phenyl)-2-tetrazol-2-yl-ethyl ester |
| 162 | 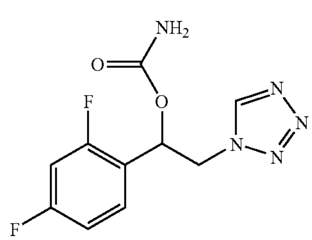 | Carbamic acid 1-(2,4-difluoro-phenyl)-2-tetrazol-1-yl-ethyl ester |

-continued

| # | Structure | IUPAC |
|---|---|---|
| 163 | Chiral | 4-Benzyl-piperidine-1-carboxylic acid (S)-1-(2-chloro-phenyl)-2-[1,2,3]triazol-2-yl-ethyl ester |
| 164 | Chiral | 4-Benzyl-piperidine-1-carboxylic acid (R)-1-(2-chloro-phenyl)-2-tetrazol-2-yl-ethyl ester |
| 165 | 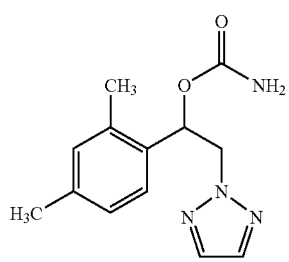 | Carbamic acid 1-(2,4-dimethyl-phenyl)-2-[1,2,3]triazol-2-yl-ethyl ester |
| 166 | Chiral | 4-Benzyl-piperidine-1-carboxylic acid (S)-1-(2-chloro-phenyl)-2-tetrazol-2-yl-ethyl ester |
| 167 | 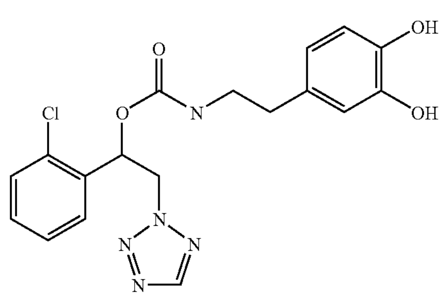 | [2-(3,4-Dihydroxy-phenyl)-ethyl]-carbamic acid 1-(2-chloro-phenyl)-2-tetrazol-2-yl-ethyl ester |

| # | Structure | IUPAC |
|---|---|---|
| 168 | 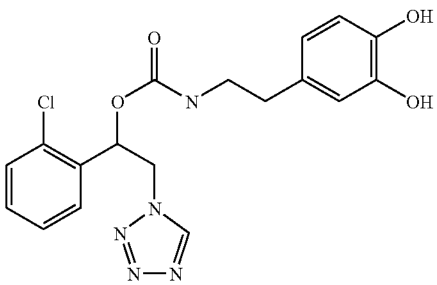 | [2-(3,4-Dihydroxy-phenyl)-ethyl]-carbamic acid 1-(2-chloro-phenyl)-2-tetrazol-1-yl-ethyl ester |
| 169 | Chiral | 4-Benzyl-piperidine-1-carboxylic acid (R)-1-(2-chloro-phenyl)-2-[1,2,3]triazol-2-yl-ethyl ester |
| 170 | 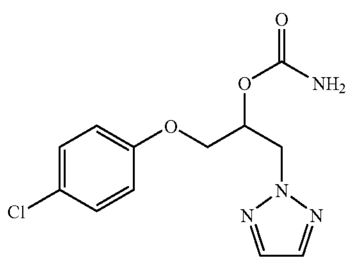 | Carbamic acid 2-(4-chloro-phenoxy)-1-[1,2,3]triazol-2-ylmethyl-ethyl ester |
| 171 | 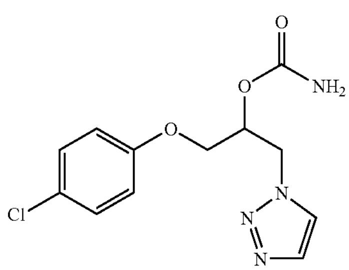 | Carbamic acid 2-(4-chloro-phenoxy)-1-[1,2,3]triazol-1-ylmethyl-ethyl ester |
| 172 | 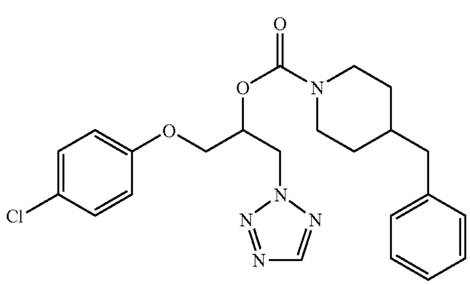 | 4-Benzyl-piperidine-1-carboxylic acid 2-(4-chloro-phenoxy)-1-tetrazol-2-ylmethyl-ethyl ester |

-continued

| # | Structure | IUPAC |
|---|---|---|
| 173 | 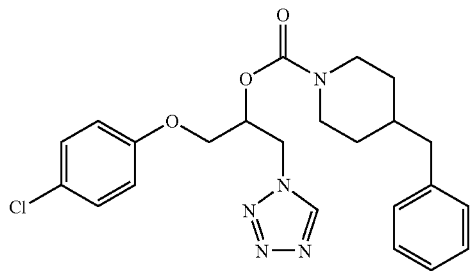 | 4-Benzyl-piperidine-1-carboxylic acid 2-(4-chloro-phenoxy)-1-tetrazol-1-ylmethyl-ethyl ester |
| 174 | 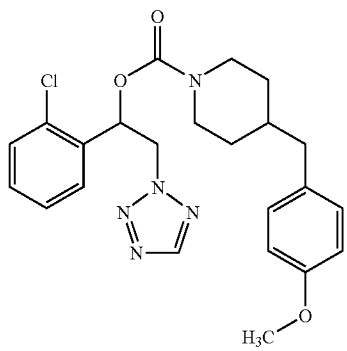 | 4-(4-Methoxy-benzyl)-piperidine-1-carboxylic acid 1-(2-chloro-phenyl)-2-tetrazol-2-yl-ethyl ester |
| 175 | 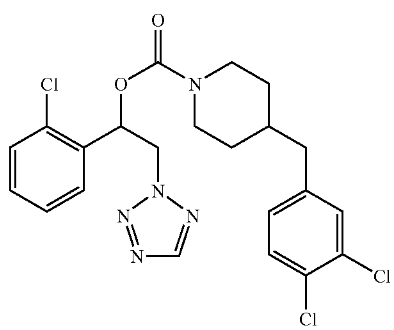 | 4-(3,4-Dichloro-benzyl)-piperidine-1-carboxylic acid 1-(2-chloro-phenyl)-2-tetrazol-2-yl-ethyl ester |
| 176 | 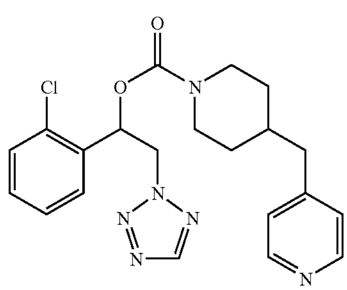 | 4-Pyridin-4-ylmethyl-piperidine-1-carboxylic acid 1-(2-chloro-phenyl)-2-tetrazol-2-yl-ethyl ester |
| 177 | 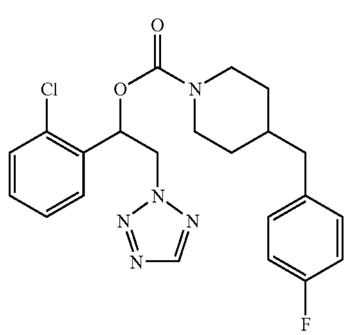 | 4-(4-Fluoro-benzyl)-piperidine-1-carboxylic acid 1-(2-chloro-phenyl)-2-tetrazol-2-yl-ethyl ester |

-continued

| # | Structure | IUPAC |
|---|---|---|
| 178 | 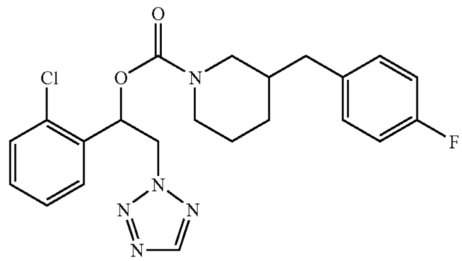 | 3-(4-Fluoro-benzyl)-piperidine-1-carboxylic acid 1-(2-chloro-phenyl)-2-tetrazol-2-yl-ethyl ester |
| 179 | 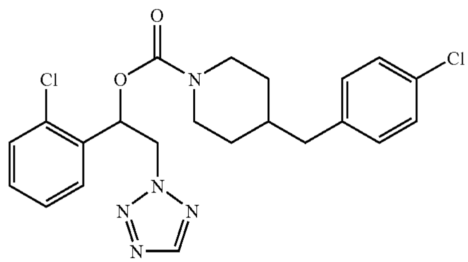 | 4-(4-Chloro-benzyl)-piperidine-1-carboxylic acid 1-(2-chloro-phenyl)-2-tetrazol-2-yl-ethyl ester |
| 180 | 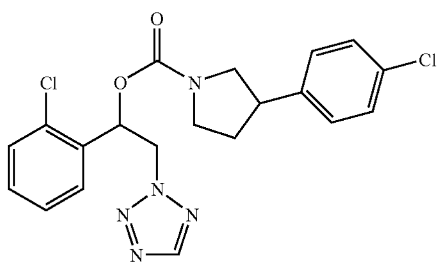 | 3-(4-Chloro-phenyl)-pyrrolidine-1-carboxylic acid 1-(2-chloro-phenyl)-2-tetrazol-2-yl-ethyl ester |
| 181 | 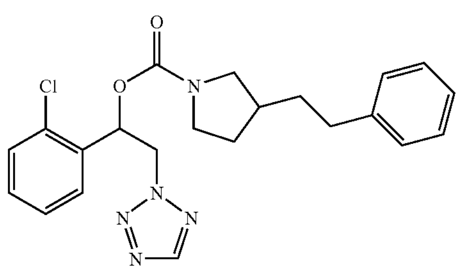 | 3-Phenethyl-pyrrolidine-1-carboxylic acid 1-(2-chloro-phenyl)-2-tetrazol-2-yl-ethyl ester |
| 182 | 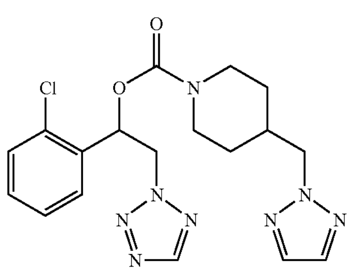 | 4-[1,2,3]Triazol-2-ylmethyl-piperidine-1-carboxylic acid 1-(2-chloro-phenyl)-2-tetrazol-2-yl-ethyl ester |

-continued

| # | Structure | IUPAC |
|---|---|---|
| 183 | 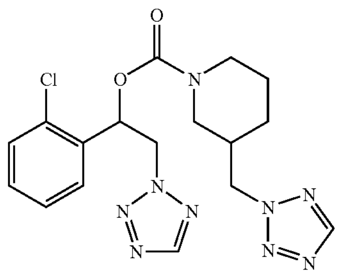 | 3-Tetrazol-2-ylmethyl-piperidine-1-carboxylic acid 1-(2-chloro-phenyl)-2-tetrazol-2-yl-ethyl ester |
| 184 | 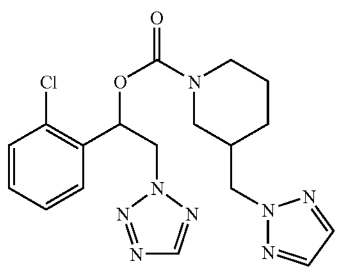 | 3-[1,2,3]Triazol-2-ylmethyl-piperidine-1-carboxylic acid 1-(2-chloro-phenyl)-2-tetrazol-2-yl-ethyl ester |
| 185 | 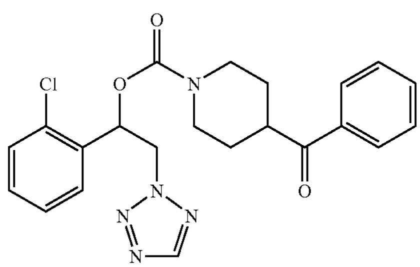 | 4-Benzoyl-piperidine-1-carboxylic acid 1-(2-chloro-phenyl)-2-tetrazol-2-yl-ethyl ester |
| 186 | 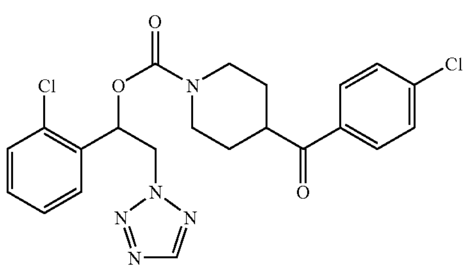 | 4-(4-Chloro-benzoyl)-piperidine-1-carboxylic acid 1-(2-chloro-phenyl)-2-tetrazol-2-yl-ethyl ester |
| 187 | 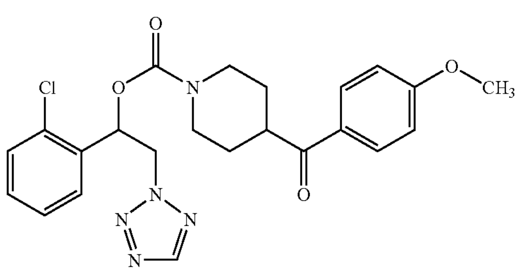 | 4-(4-Methoxy-benzoyl)-piperidine-1-carboxylic acid 1-(2-chloro-phenyl)-2-tetrazol-2-yl-ethyl ester |

-continued

| # | Structure | IUPAC |
|---|---|---|
| 188 | 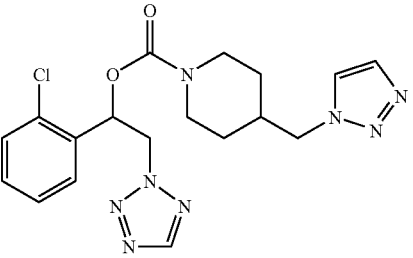 | 4-[1,2,3]Triazol-1-ylmethyl-piperidine-1-carboxylic acid 1-(2-chloro-phenyl)-2-tetrazol-2-yl-ethyl ester |
| 189 | 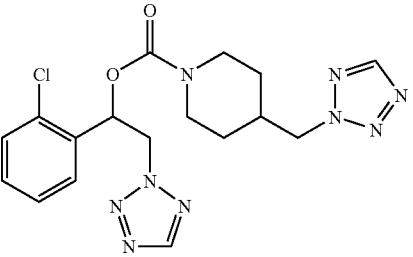 | 4-Tetrazol-2-ylmethyl-piperidine-1-carboxylic acid 1-(2-chloro-phenyl)-2-tetrazol-2-yl-ethyl ester |
| 190 | 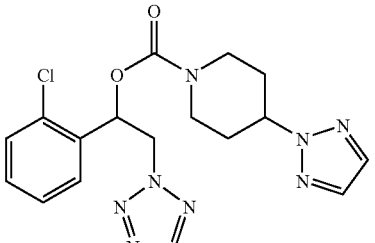 | 4-[1,2,3]Triazol-2-yl-piperidine-1-carboxylic acid 1-(2-chloro-phenyl)-2-tetrazol-2-yl-ethyl ester |
| 191 | 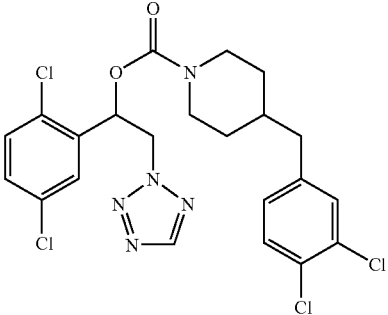 | 4-(3,4-Dichloro-benzyl)-piperidine-1-carboxylic acid 1-(2,5-dichloro-phenyl)-2-tetrazol-2-yl-ethyl ester |
| 192 | 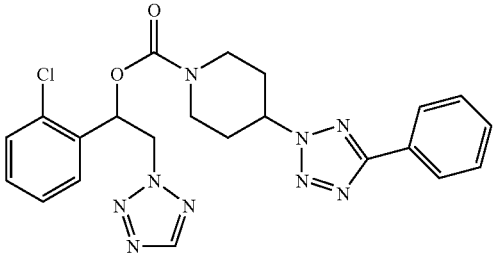 | 4-(5-Phenyl-tetrazol-2-yl)-piperidine-1-carboxylic acid 1-(2-chloro-phenyl)-2-tetrazol-2-yl-ethyl ester |

| # | Structure | IUPAC |
|---|---|---|
| 193 | 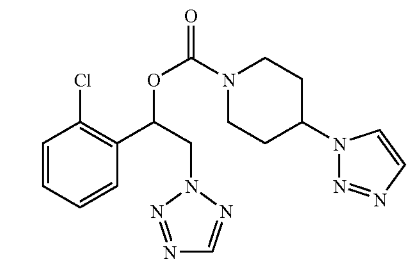 | 4-[1,2,3]Triazol-1-yl-piperidine-1-carboxylic acid 1-(2-chloro-phenyl)-2-tetrazol-2-yl-ethyl ester |
| 194 | 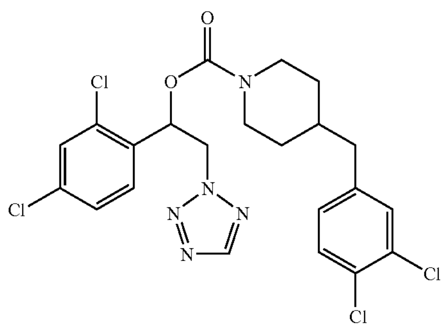 | 4-(3,4-Dichloro-benzyl)-piperidine-1-carboxylic acid 1-(2,4-dichloro-phenyl)-2-tetrazol-2-yl-ethyl ester |
| 195 | 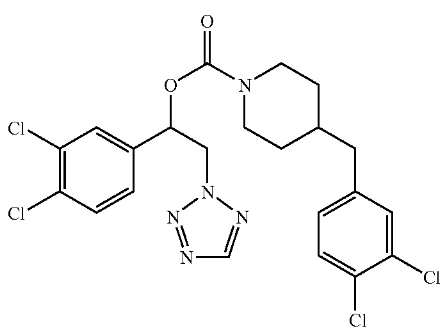 | 4-(3,4-Dichloro-benzyl)-piperidine-1-carboxylic acid 1-(3,4-dichloro-phenyl)-2-tetrazol-2-yl-ethyl ester |
| 196 | 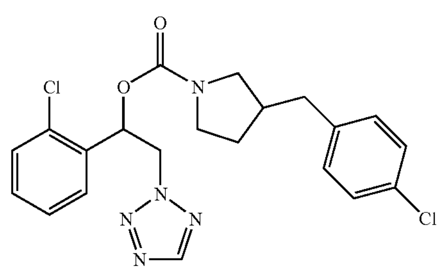 | 3-(4-Chloro-benzyl)-pyrrolidine-1-carboxylic acid 1-(2-chloro-phenyl)-2-tetrazol-2-yl-ethyl ester |
| 197 | 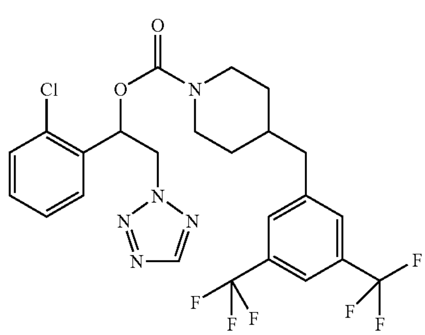 | 4-(3,5-Bis-trifluoromethyl-benzyl)-piperidine-1-carboxylic acid 1-(2-chloro-phenyl)-2-tetrazol-2-yl-ethyl ester |

-continued

| # | Structure | IUPAC |
|---|---|---|
| 198 | 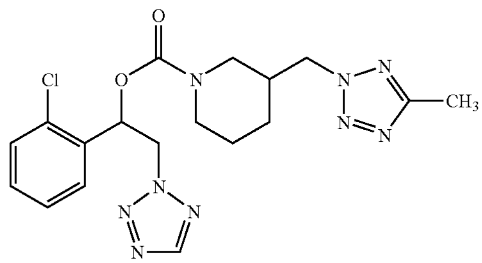 | 3-(5-Methyl-tetrazol-2-ylmethyl)-piperidine-1-carboxylic acid 1-(2-chloro-phenyl)-2-tetrazol-2-yl-ethyl ester |
| 199 | 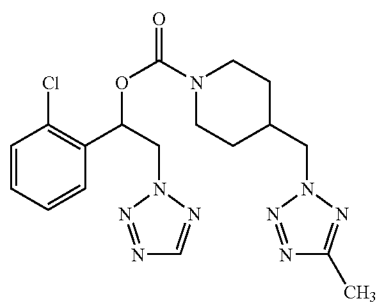 | 4-(5-Methyl-tetrazol-2-ylmethyl)-piperidine-1-carboxylic acid 1-(2-chloro-phenyl)-2-tetrazol-2-yl-ethyl ester |
| 200 | 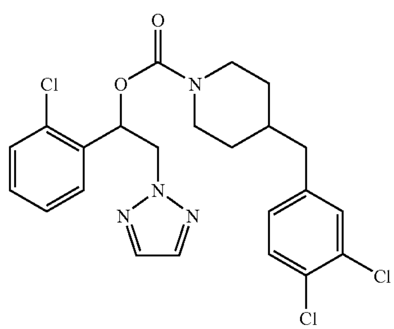 | 4-(3,4-Dichloro-benzyl)-piperidine-1-carboxylic acid 1-(2-chloro-phenyl)-2-[1,2,3]triazol-2-yl-ethyl ester |
| 201 | 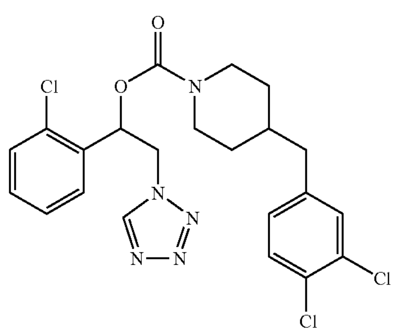 | 4-(3,4-Dichloro-benzyl)-piperidine-1-carboxylic acid 1-(2-chloro-phenyl)-2-tetrazol-1-yl-ethyl ester |
| 202 | 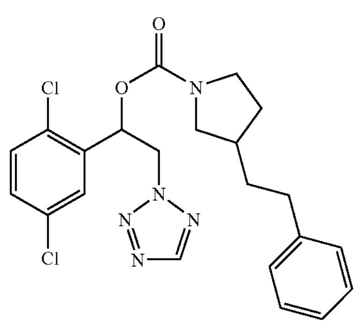 | 3-Phenethyl-pyrrolidine-1-carboxylic acid 1-(2,5-dichloro-phenyl)-2-tetrazol-2-yl-ethyl ester |

| # | Structure | IUPAC |
|---|---|---|
| 203 | 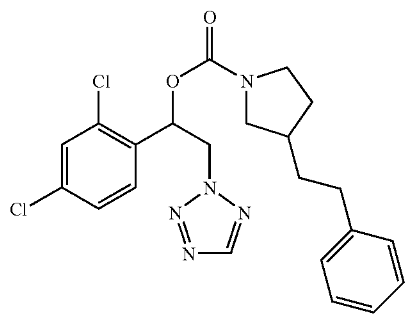 | 3-Phenethyl-pyrrolidine-1-carboxylic acid 1-(2,4-dichloro-phenyl)-2-tetrazol-2-yl-ethyl ester |
| 204 | 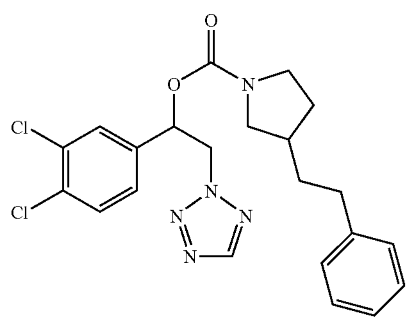 | 3-Phenethyl-pyrrolidine-1-carboxylic acid 1-(3,4-dichloro-phenyl)-2-tetrazol-2-yl-ethyl ester |
| 205 | 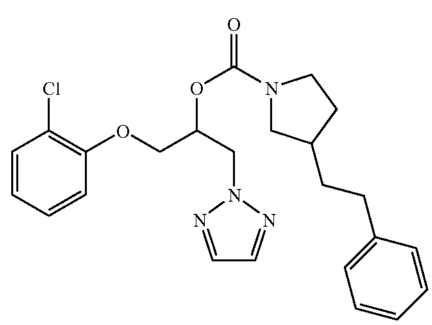 | 3-Phenethyl-pyrrolidine-1-carboxylic acid 2-(2-chloro-phenoxy)-1-[1,2,3]triazol-2-ylmethyl-ethyl ester |
| 206 | 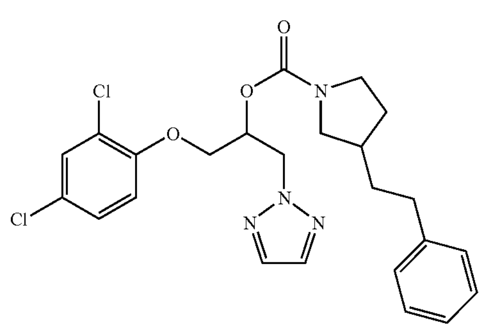 | 3-Phenethyl-pyrrolidine-1-carboxylic acid 2-(2,4-dichloro-phenoxy)-1-[1,2,3]triazol-2-ylmethyl-ethyl ester |

| # | Structure | IUPAC |
|---|---|---|
| 207 | 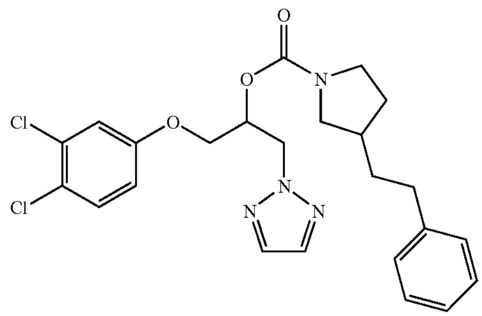 | 3-Phenethyl-pyrrolidine-1-carboxylic acid 2-(3,4-dichloro-phenoxy)-1-[1,2,3]triazol-2-ylmethyl-ethyl ester |
| 208 | 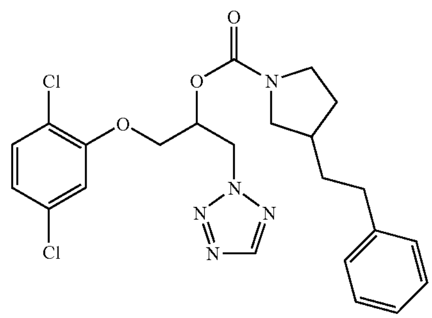 | 3-Phenethyl-pyrrolidine-1-carboxylic acid 2-(2,5-dichloro-phenoxy)-1-tetrazol-2-ylmethyl-ethyl ester |
| 209 | 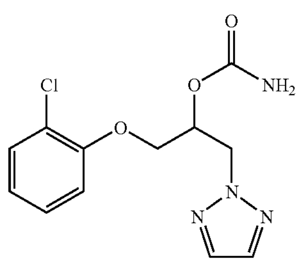 | Carbamic acid 2-(2-chloro-phenoxy)-1-[1,2,3]triazol-2-ylmethyl-ethyl ester |
| 210 | 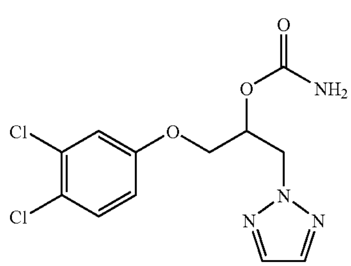 | Carbamic acid 2-(3,4-dichloro-phenoxy)-1-[1,2,3]triazol-2-ylmethyl-ethyl ester |
| 211 | 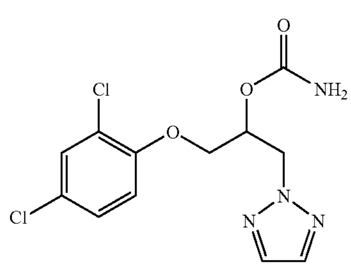 | Carbamic acid 2-(2,4-dichloro-phenoxy)-1-[1,2,3]triazol-2-ylmethyl-ethyl ester |

| # | Structure | IUPAC |
|---|---|---|
| 212 | 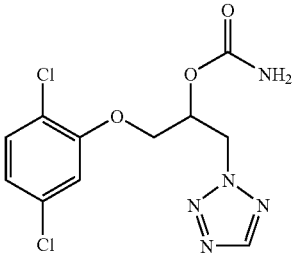 | Carbamic acid 2-(2,5-dichloro-phenoxy)-1-tetrazol-2-ylmethyl-ethyl ester |
| 213 | 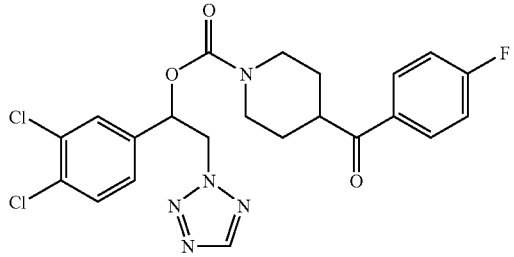 | 4-(4-Fluoro-benzoyl)-piperidine-1-carboxylic acid 1-(3,4-dichloro-phenyl)-2-tetrazol-2-yl-ethyl ester |
| 214 | 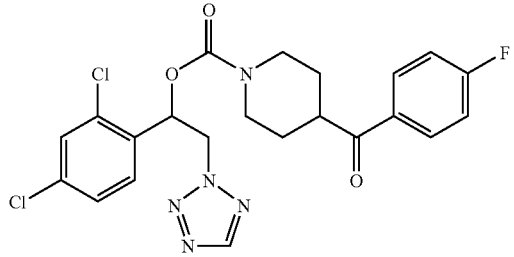 | 4-(4-Fluoro-benzoyl)-piperidine-1-carboxylic acid 1-(2,4-dichloro-phenyl)-2-tetrazol-2-yl-ethyl ester |
| 215 | 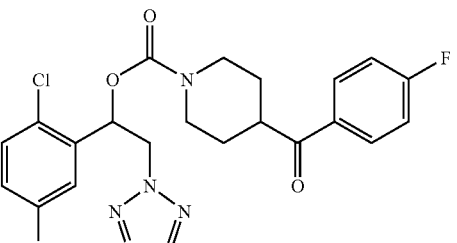 | 4-(4-Fluoro-benzoyl)-piperidine-1-carboxylic acid 1-(2,5-dichloro-phenyl)-2-tetrazol-2-yl-ethyl ester |
| 216 | 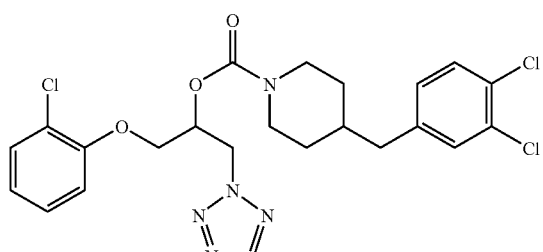 | 4-(3,4-Dichloro-benzyl)-piperidine-1-carboxylic acid 2-(2-chloro-phenoxy)-1-tetrazol-2-ylmethyl-ethyl ester |

-continued

| # | Structure | IUPAC |
|---|-----------|-------|
| 217 | 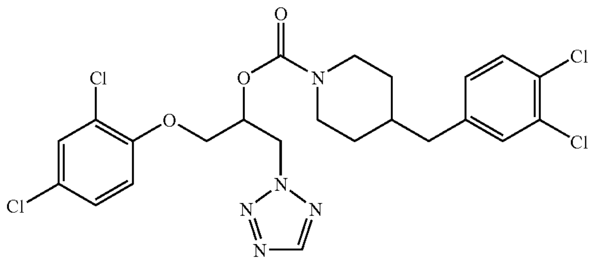 | 4-(3,4-Dichloro-benzyl)-piperidine-1-carboxylic acid 2-(2,4-dichloro-phenoxy)-1-tetrazol-2-ylmethyl-ethyl ester |
| 218 | 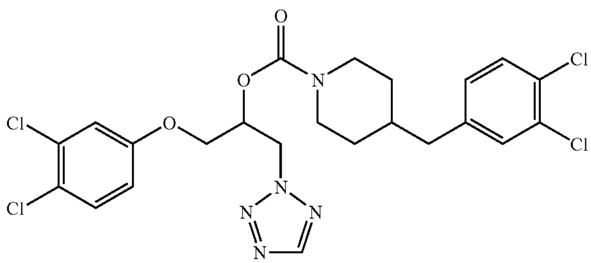 | 4-(3,4-Dichloro-benzyl)-piperidine-1-carboxylic acid 2-(3,4-dichloro-phenoxy)-1-tetrazol-2-ylmethyl-ethyl ester |
| 219 | 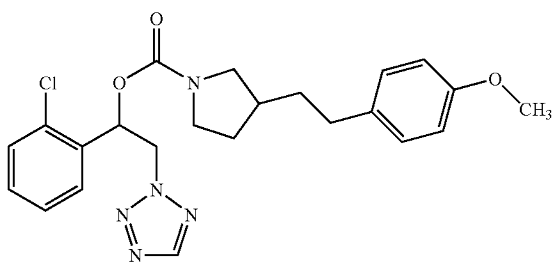 | 3-[2-(4-Methoxy-phenyl)-ethyl]-pyrrolidine-1-carboxylic acid 1-(2-chloro-phenyl)-2-tetrazol-2-yl-ethyl ester |
| 220 | 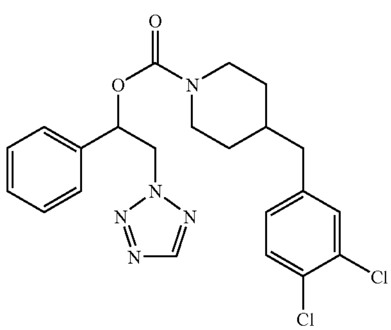 | 4-(3,4-Dichloro-benzyl)-piperidine-1-carboxylic acid 1-phenyl-2-tetrazol-2-yl-ethyl ester |
| 221 | 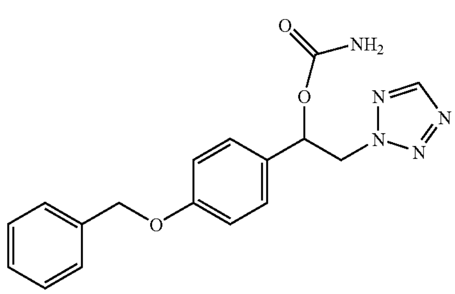 | Carbamic acid 1-(4-benzyloxy-phenyl)-2-tetrazol-2-yl-ethyl ester |

-continued

| # | Structure | IUPAC |
|---|-----------|-------|
| 222 | 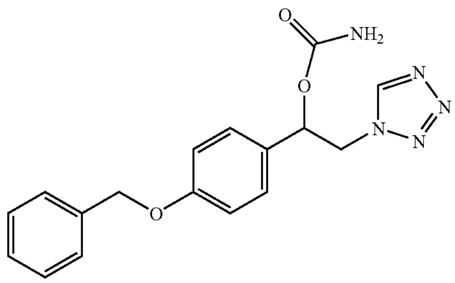 | Carbamic acid 1-(4-benzyloxy-phenyl)-2-tetrazol-1-yl-ethyl ester |
| 223 | 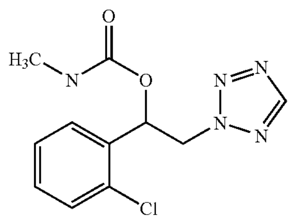 | methyl-carbamic acid -1-(2-chloro-phenyl)-2-tetrazol-2-yl-ethyl ester |
| 224 | 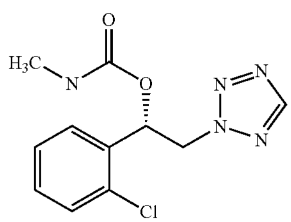 | methyl-carbamic acid (S)-1-(2-chloro-phenyl)-2-tetrazol-2-yl-ethyl ester |
| 225 | 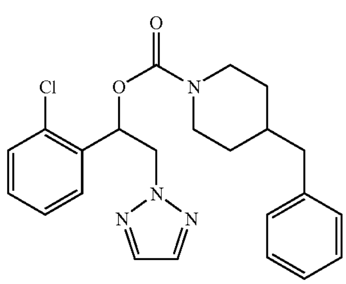 | 4-benzyl-piperidine-1-carboxylic acid-1-(2-chloro-phenyl)-2-[1,2,3]triazol-2-yl-ethyl ester |
| 226 | 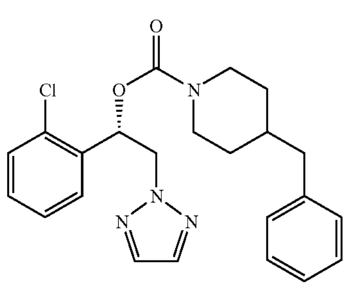 | 4-benzyl-piperidine-1-carboxylic acid (S)-1-(2-chloro-phenyl)-2-[1,2,3]triazol-2-yl-ethyl ester |

What is claimed is:

1. An azole compound of the formula:

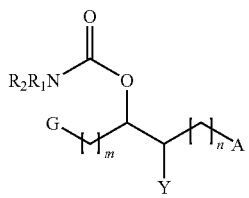

wherein, G is a ring selected from the group consisting of piperonyl, indanyl, naphtyl, phenyl and phenoxy methyl which ring may be substituted with one or more identical or different substituents selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, perfluoroalkyl, phenoxy, phenylalkyloxy of 1 to 8 carbon atoms or phenoxyalkyl of 1 to 8 carbon atoms, wherein the phenyl moiety of phenoxy, phenoxyalkyl and phenylalkyloxy is unsubstituted or substituted with amino, mono- or di-substituted amino with lower alkyl of 1 to 8 carbon atoms, amido, sulfonamido, nitro, carboxyl, or perfluoroalkyl of 1 to 8 carbon atoms;

m is an integer from 0 to 6;

Y is selected from the group consisting of hydrogen, halogen, and lower alkyl of 1 to 8 carbon atoms;

n is an integer from 0 to 6;

A is azole group represented by the following structural formula (X-1) or (X-2):

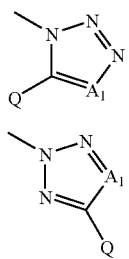

wherein, $A_1$ is selected from the group consisting of nitrogen atom and CH;

Q is selected from the group consisting of hydrogen, perfluoroalkyl, halogen, amino, mono- or di-substituted alkyl amino with alkyl of 1 to 8 carbon atoms, amido, linear or branched alkyl of 1 to 8 carbon atoms, cycloalkyl of 3 to 8 carbon atoms, arylalkyl, morpholino, piperidino, pyrrolidino, thioalkoxy of 1 to 8 carbon atoms, benzylthio, thienyl, aminoalkyl, hydroxyalkyl, styryl, carboxylic, pyridyl, unsubstituted phenyl and phenyl substituted with one or more identical or different substituents selected from the group consisting of hydrogen, lower alkyl of 1 to 8 carbon atoms, arylalkyl, halogen, alkoxy containing 1 to 8 carbon atoms, phenoxy, amino, mono- or di-substituted amino with alkyl of 1 to 8 carbon atoms, nitro, hydroxy, thioalkoxy, furanyl, sulfonamido, or perfluoroalkyl;

$R_1$ and $R_2$ are independently selected from the group consisting of hydrogen, C(=O)NH$_2$, lower alkyl of 1 to 8 carbon atoms, non-substituted or substituted phenyl, and non-substituted or substituted phenylalkyl of 1 to 8 carbon atoms, or taken together with attached nitrogen form a imidazole, piperazine or phenyl piperazine ring or cyclic amine ring represented by the following structural formula (XI):

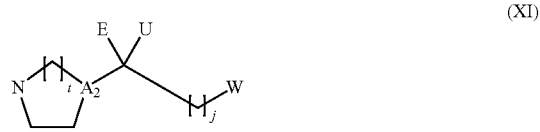

wherein, $A_2$ is selected from the group consisting of nitrogen atom and carbon atom;

E and U are independently selected from the group consisting of hydrogen, hydroxy and O-carbamoyl or taken together form oxo;

W is selected from a ring consisting of piperonyl, indanyl, naphtyl, tetrazolyl, triazolyl, pyridyl and phenyl which ring may be substituted with one or more identical or different substituents selected from the group consisting of hydrogen, lower alkyl of 1 to 8 carbon atoms, halogen, alkoxy containing 1 to 8 carbon atoms, thioalkoxy containing 1 to 8 carbon atoms, phenoxy, phenylalkyloxy of 1 to 8 carbon atoms, phenyloxyalkyl of 1 to 8 carbon atoms, where the phenyl moiety of phenoxy, phenylalkyloxy and phenoxyalkyl is unsubstituted or substituted with amino, mono- or di-substituted amino with alkyl of 1 to 8 carbon atoms, amido, sulfonamido, nitro, carboxyl, hydroxy, or perfluoroalkyl of 1 to 8 carbon atoms;

j is an integer from 0 to 4; and t is an integer from 0 to 4;

or a pharmaceutically acceptable salt thereof.

2. The azole of claim 1, wherein said compound has the formula:

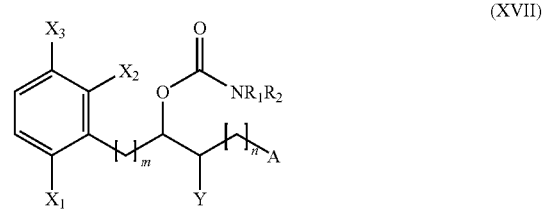

wherein, $X_1$ is selected from the group consisting of lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, phenoxyalkyl of 1 to 8 carbon atoms wherein the phenyl moiety of phenoxy, phenylalkyloxy and phenoxyalkyl is unsubstituted or substituted with amino, mono- or di-substituted amino with lower alkyl of 1 to 8 carbon atoms, amido, sulfonamido, nitro, carboxyl, or perfluoroalkyl of 1 to 8 carbon atoms;

$X_2$ and $X_3$ may be the same with or different from each other and are independently selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, phenoxyalkyl of 1 to 8 carbon atoms wherein the phenyl moiety of phenoxy, phenylalkyloxy and phenoxyalkyl is unsubstituted or substituted with amino, mono- or disubstituted amino with lower alkyl of 1 to 8 carbon atoms, amido, sulfonamido, nitro, carboxyl, or perfluoroalkyl of 1 to 8 carbon atoms;
m is an integer from 0 to 6;
Y is selected from the group consisting of hydrogen and lower alkyl of 1 to 8 carbon atoms;
n is an integer from 0 to 6;
A is azole group represented by the following structural formula (X-1) or (X-2):

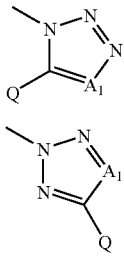

(X-1)

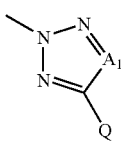

(X-2)

wherein, $A_1$ is selected from the group consisting of nitrogen atom and CH;
Q is as above; and
$R_1$ and $R_2$ are as above; or
a pharmaceutically acceptable salt thereof.

3. The azole of claim 1, wherein said compound has the formula:

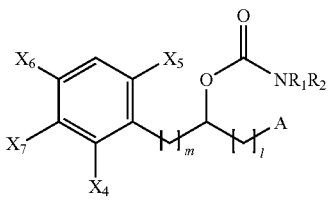

(XVIII)

wherein, $X_4$ and $X_6$ are independently selected from the group consisting of lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, phenoxyalkyl of 1 to 8 carbon atoms wherein the phenyl moiety of phenoxy, phenylalkyloxy and phenoxyalkyl is unsubstituted or substituted with amino, mono- or di-substituted alkyl amino with alkyl of 1 to 8 carbon atoms, amido, sulfonamido, nitro, carboxyl, or perfluoroalkyl of 1 to 8 carbon atoms;
$X_5$ and $X_7$ may the same with or different from each other and are independently selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy of 1 to 8 carbon atoms, phenoxyalkyl of 1 to 8 carbon atoms wherein the phenyl moiety of phenoxy, phenylalkyloxy and phenoxyalkyl is unsubstituted or substituted with amino, mono- or di-substituted alkyl amino with alkyl of 1 to 8 carbon atoms, amido, sulfonamido, nitro, carboxyl, or perfluoroalkyl of 1 to 8 carbon atoms;
m is an integer from 0 to 6;
l is an integer from 1 to 6;
A is azole group represented by the following structural formula (X-1) or (X-2):

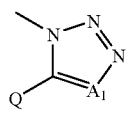

(X-1)

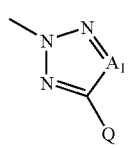

(X-2)

wherein, $A_1$ is selected from the group consisting of nitrogen atom and CH; and
Q, $R_1$ and $R_2$ are as above.

4. The azole of claim 1, wherein said compound has the formula:

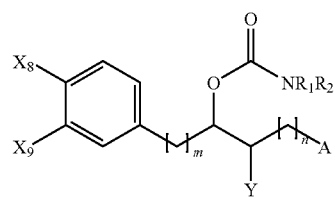

(XIX)

wherein, $X_8$ and $X_9$ are independently selected from the group consisting of hydrogen, lower alkyl of 1 to 8 carbon atoms, halogen, alkoxy containing 1 to 8 carbon atoms, thioalkoxy containing 1 to 8 carbon atoms, hydroxy, phenoxy, phenylalkyloxy, phenoxyalkyl wherein the phenyl moiety of phenoxy, phenylalkyloxy and phenoxyalkyl is unsubstituted or substituted with amino, mono- or di-substituted amino with alkyl of 1 to 8 carbon atoms, amido, sulfonamido, nitro, carboxyl, and perfluoroalkyl of 1 to 8 carbon atoms;
m is an integer from 0 to 6;
Y is selected from the group consisting of hydrogen and lower alkyl of 1 to 8 carbon atoms;
n is an integer from 0 to 6; and
A, $R_1$ and $R_2$ are as above.

5. The azole of claim 1, wherein said compound has the formula:

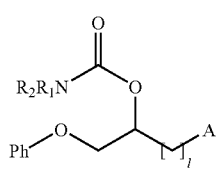

(XX)

wherein, Ph is phenyl, piperonyl, indanyl or naphtyl which maybe substituted with one or more identical or different substituents selected from the group consisting of hydrogen, lower alkyl of 1 to 8 carbon atoms, halogen, alkoxy containing 1 to 8 carbon atoms, thioalkoxy containing 1 to 8 carbon atoms, phenoxy, phenylalkyloxy of 1 to 8 carbon atoms, phenoxyalkyl of 1 to 8 carbon atoms, wherein the phenyl moiety of phenoxy, phenylalkyloxy and phenoxyalkyl is unsubstituted or substituted with amino, mono- or di-substituted amino with alkyl of 1 to 8 carbon atoms, amido, sulfonamido, nitro, carboxyl, hydroxy, or perfluoroalkyl of 1 to 8 carbon atoms;
l is an integer from 1 to 6; and
A, $R_1$ and $R_2$ are as above.

6. The azole of claim 1, wherein said compound has the formula:

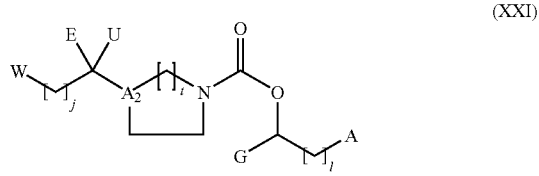

(XXI)

wherein, E, U, W, $A_2$, A, G, j and t are as above and
l is an integer from 1 to 4;
or a pharmaceutically acceptable salt thereof.

7. The azole of claim 1, wherein said compound has the formula:

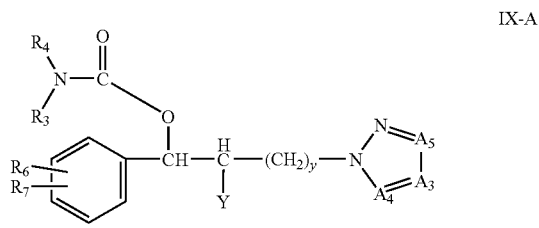

IX-A wherein Y is as above;
$A_3$, $A_4$ and $A_5$ are independently selected from the group consisting of CH or N, with at least one of $A_3$, $A_4$ and $A_5$ being CH and at least one of the other of $A_3$, $A_4$ and $A_5$ being N;
$R_6$ and $R_7$ being selected from the group consisting of hydrogen, halogen, perfluoroalkyl, alkyl of from 1 to 8 carbon atoms, lower alkoxy, thioalkoxy;
$R_3$ and $R_4$ are alkyl or hydrogen,

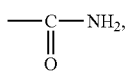

or taken together with the attached nitrogen atom forms an imidazole, or phenyl piperazine ring; or
y is an integer of from 0 to 4.

8. The azole of claim 7, wherein one of $A_3$, $A_4$ and $A_5$ are CH and the others are N.

9. The azole of claim 8, wherein $R_6$ and $R_7$ are independently hydrogen, halogen or perfluoroalkyl.

10. The azole of claim 9, wherein said compound is carbamic acid 1-(2-chloro-phenyl)-2tetrazol-2-yl-ethyl ester.

11. The azole of claim 10, wherein said compound is carbamic acid (R)-(+)-1-(2-chloro-phenyl)-2-tetrazol-2-yl-ethyl ester substantially free of its (S)enantiomer and said (R)-enantiomer is present to the extent of at least about 95%.

12. The azole of claim 10, wherein said compound is carbamic acid (S)-(−)-1-(2-chloro-phenyl)-2-tetrazol-2-yl-ethyl ester substantially; free of its (R)-enantiomer and said (S)-enantiomer is present to the extent of at least about 95%.

13. The azole of claim 9, wherein said compound is methyl-carbamic acid-1-(2-chloro-phenyl)-2-tetrazol-2-yl-ethyl ester.

14. The azole of claim 13, wherein said compound is methyl-carbamic acid (R)-1-(2-chloro-phenyl)-2-tetrazol-2-yl-ethyl ester substantially free of its (S)-enantiomer and said (R)-enantiomer is present to the extent of at least about 95%.

15. The azole of claim 13, wherein said compound is methyl-carbamic acid (S)-1-(2-chloro-phenyl)-2-tetrazol-2-yl-ethyl ester substantially free of its (R)-enantiomer and said (S)-enantiomer is present to the extent of at least about 95%.

16. The azole of claim 9, wherein said compound is carbamic acid -1-(2,4-dichloro-phenyl)2-tetrazol-2-yl-ethyl ester.

17. The azole of claim 16, wherein said compound is carbamic acid (R)-1-(2,4-dichloro-phenyl)-2-tetrazol-2-yl-ethyl ester substantially free of its (S)-enantiomer and said (R)-enantiomer is present to the extent of at least about 95%.

18. The azole of claim 16, wherein said compound is carbamic acid (S)-1-(2,4-dichloro-phenyl)-2-tetrazol-2-yl-ethyl ester substantially free of its (R)-enantiomer and said (S)-enantiomer is present to the extent of at least about 95%.

19. The azole of claim 9, wherein said compound is carbamic acid 1-(3,4-dichloro-phenyl)-2-tetrazol-2-yl-ethyl ester.

20. The azole of claim 19, wherein said compound is carbamic acid (R)-1-(3,4-dichloro-phenyl)-2-tetrazol-2-yl-ethyl ester substantially free of its (S)-enantiomer and said (R)-enantiomer is present to the extent of at least about 95%.

21. The azole of claim 19, wherein said compound is carbamic acid (S)-1-(3,4-dichloro-phenyl)-2-tetrazol-2-yl-ethyl ester substantially free of its (R)-enantiomer and said (S)-enantiomer is present to the extent of at least about 95%.

22. The azole of claim 9, wherein said compound is carbamic acid-1-(2,6-dichloro-phenyl)-2-tetrazol-2-yl-ethyl ester.

23. The azole of claim 9, wherein said compound is carbamic acid 1-(3,4-dichloro-phenyl)-2-tetrazol-2-yl-propyl ester.

24. The azole of claim 7, wherein one of $A_3$, $A_4$ and $A_5$ is N and the others are CH.

25. The azole of claim 24, wherein $R_6$ and $R_7$ are independently hydrogen, halogen or perfluoroalkyl.

26. The azole of claim 25, wherein said compound is carbamic acid-1-(2-chloro-phenyl)-2-[1,2,3]triazol-2-yl-ethyl ester.

27. The azole in accordance with claim 26 wherein said compound is Carbamic acid (R)-1-(2-chloro-phenyl)-2-[1,2,3]triazol-2-yl-ethyl ester substantially free of its (S)-enantiomer and said (R)-enantiomer is present to the extent of at least about 95%.

28. The azole in accordance with claim 26 wherein said compound is Carbamic acid (S)-1-(2-chloro-phenyl)-2-[1,2,3]triazol-2-yl-ethyl ester substantially free of its (R)-enantiomer and said (S)-enantiomer is present to the extent of at least about 95%.

29. The azole of claim 25, wherein said compound is carbamic acid-1-(2,4-dichloro-phenyl)-2-[1,2,3]triazol-1-yl-ethyl ester.

30. The azole in accordance with claim 29 wherein said compound is Carbamic acid (R)-1-(2,4-dichloro-phenyl)-2-[1,2,3]triazol-2-yl-ethyl ester substantially free of its (S)-enantiomer and said (R)-enantiomer is present to the extent of at least about 95%.

31. The azole in accordance with claim 29 wherein said compound is Carbamic acid (S)-1-(2,4-dichloro-phenyl)-2-[1,2,3]triazol-2-yl-ethyl ester substantially free of its (R)-enantiomer and said (S)-enantiomer is present to the extent of at least about 95%.

32. The azole of claim 25, wherein said compound is carbamic acid 1-(3,4-dichloro-phenyl)-2-[1,2,3]triazol-2-yl-ethyl ester.

33. The azole in accordance with claim 32 wherein said compound is Carbamic acid (R)-1-(3,4-dichloro-phenyl)-2-[1,2,3]triazol-2-yl-ethyl ester substantially free of its (S)-enantiomer and said (R)-enantiomer is present to the extent of at least about 95%.

34. The azole in accordance with claim 32 wherein said compound is Carbamic acid (S)-1-(3,4-dichloro-phenyl)-2-[1,2,3]triazol-2-yl-ethyl ester substantially free of its (R)-enantiomer and said (S)-enantiomer is present to the extent of at least about 95%.

35. The azole of claim 1 wherein said compound has the formula:

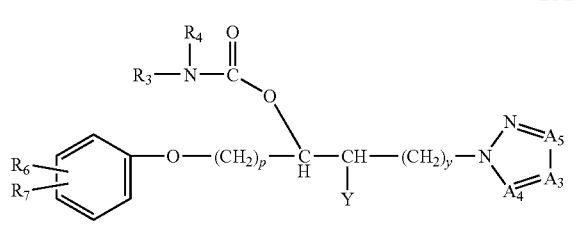

IX-B wherein Y is as above;
$A_3, A_4$ and $A_5$ are independently selected from the group consisting of CH or N, with at least one of $A_3, A_4$ and $A_5$ being CH and at least one of the other of $A_3, A_4$ and $A_5$ being N;
$R_6$ and $R_7$ being selected from the group consisting of hydrogen, halogen, perfluoroalkyl, alkyl of from 1 to 8 carbon atoms, thioalkoxy;
$R_3$ and $R_4$ are alkyl or hydrogen,

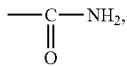

or taken together with the attached nitrogen atom form an imidazole, or phenyl piperazine ring;
y is an integer of from 0 to 4; and
p is an integer from 0 to 1.

36. The azole of claim 35, wherein $R_6$ and $R_7$ are independently hydrogen, halogen or perfluoroalkyl.

37. The azole of claim 36, wherein said compound is carbamic acid 2-(3,4-dichloro-phenoxy)-1-tetrazol-2-ylmethyl-ethyl ester.

38. The azole of claim 36, wherein said compound is carbamic acid 2-(2-chloro-phenoxy)-1-tetrazol-2-ylmethyl-ethyl ester.

39. The azole of claim 35, wherein one of $A_3, A_4$ and $A_5$ is N and the others are CH.

40. The azole of claim 39, wherein $R_6$ and $R_7$ are independently hydrogen, halogen or perfluoroalkyl.

41. The azole of claim 40, wherein said compound is carbamic acid 2-(2,4-dichloro-phenoxy)-1-[1,2,3]triazol-2-yl-methyl-ethyl ester.

42. The azole of claim 1, wherein said compound is:

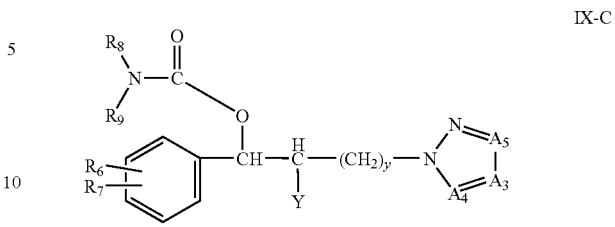

IX-C wherein $R_8$ and $R_9$ taken together with the attached nitrogen atom form a substituent of the formula:

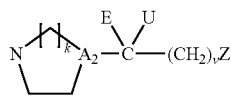

wherein E, U and $A_2$ are as above;
k and v are an integer from 0 to 1;
Z is a phenyl, phenoxy, alkyl or phenylalkyloxy substitued where the phenyl moiety of said substitutent is unsubstituted or substituted with from one to three substituents selected from the group consisting of halogen, alkyl, perfluoroalkyl or alkoxy;
$A_3, A_4$ and $A_5$ are independently selected from the group consisting of CH or N, with at least one of $A_3, A_4$ and $A_5$ being CH and at least one of the other of $A_3, A_4$ and $A_5$ being N;
Y is a hydrogen, halogen or alkyl;
y is an integer of from 0 to 1;
$R_6$ and $R_7$ are selected from the group consisting of hydrogen, halogen, perfluoroalkyl, thioalkoxy, alkoxy and alkyl; or a
pharmaceutically acceptable salt thereof.

43. The azole of claim 42, wherein one of $A_3, A_4$ and $A_5$ are CH and the others are N.

44. The azole of claim 43, wherein $R_6$ and $R_7$ are independently hydrogen, halogen or perfluoroalkyl.

45. The azole of claim 44, wherein said compound is 4-(3,4-dichloro-benzyl)-piperidine-1-carboxylic acid 1-(2,4-dichloro-phenyl)-2-tetrazol-2-yl-ethyl ester.

46. The azole of claim 44, wherein said compound is 4-(3,4-dichloro-benzyl)-piperidine-1-carboxylic acid 1-(3,4-dichloro-phenyl)-2-tetrazol-2-yl-ethyl ester.

47. The azole of claim 44, wherein said compound is 4-(3,5-bis-trifluoromethyl-benzyl)-piperidine-1-carboxylic acid 1-(2-chloro-phenyl)-2-tetrazol-2-yl-ethyl ester.

48. The azole of claim 44, wherein said compound is 3-phenethyl-pyrrolidine-1-carboxylic acid 1-(2,5-dichloro-phenyl)-2-tetrazol-2-yl-ethyl ester.

49. The azole of claim 42, wherein one of $A_3, A_4$ and $A_5$ is N and the others are CH.

50. The azole of claim 49, wherein $R_6$ and $R_7$ are independently hydrogen, halogen or perfluoroalkyl.

51. The azole of claim 50, wherein said compound is 4-benzyl-piperidine-1-carboxylic acid-1-(2-chloro-phenyl)-2-[1,2,3]triazol-2-yl-ethyl ester.

52. The azole in accordance with claim 51 wherein said compound is 4-benzyl-piperidine-1-carboxylic acid (R)-1-(2-chloro-phenyl)-2-[1,2,3]triazol-2-yl-ethyl ester substantially free of its (S)-enantiomer and said (R)-enantiomer is present to the extent of at least about 95%.

53. The azole in accordance with claim 51 wherein said compound is 4-benzyl- piperidine-1-carboxylic acid (S)-1-(2-chloro-phenyl)-2-[1,2,3]triazol-2-yl-ethyl ester substantially free of its (R)-enantiomer and said (S)-enantiomer is present to the extent of at least about 95%.

54. The compound of claim 1 having the formula:

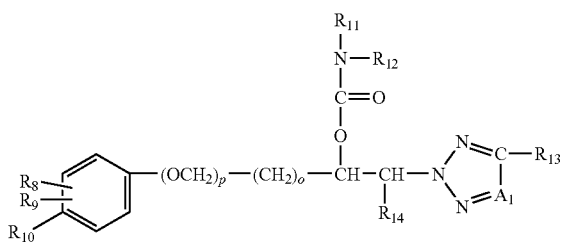

IX-D wherein $A_1$ is as above; $R_8$ and $R_9$ are hydrogen, halogen, lower alkoxy, lower alkyl, hydroxy, trifluromethyl, amino, mono or dilower alkyl amino, nitro or $R_8$ and $R_9$ when substituted on adjacent carbon atoms and when $R_{10}$ is hydrogen can be taken together to form a cyclolower alkyl, phenyl or heterocyclolower alkyl ring; $R_{10}$ is lower alkoxy, phenoxy, phenylalkoxy, hydrogen, cycloloweralkyl, halogen, hydroxy, lower alkyl, nitro, trifluoromethyl mono or lower dikalkyl amino or amino; $R_{11}$ is hydrogen, lower alkyl, phenyl or phenyl lower alkyl wherein the phenyl group can be unsubstituted or mono or disubstituted with a lower alkyl, hydroxy, lower alkoxy, or halo; $R_{12}$ is hydrogen or lower alkyl or $R_{12}$ taken together with $R_{11}$ and their attached nitrogen atom form a 4 to 6 membered heteroarmatic ring containing at most 3 additional hetero nitrogen atoms; $R_{14}$ is hydrogen, amino carbonyl, or lower alkyl: $R_{13}$ is hydrogen, lower alkyl, amino, mono or dilower alkylamino hetero aromatic, amino carbonyl or phenyl where the phenyl group can be unsubstituted or mono or disubstituted with a lower alkyl, hydroxy, lower alkoxy, or halo; and 0 and p are integers from 0-1.

55. The compound of claim 54 wherein p is 0 and o is 1.
56. The compound of claim 54 wherein o is 0 and p is 1.
57. The compound of claim 1 wherein said compound has the formula:

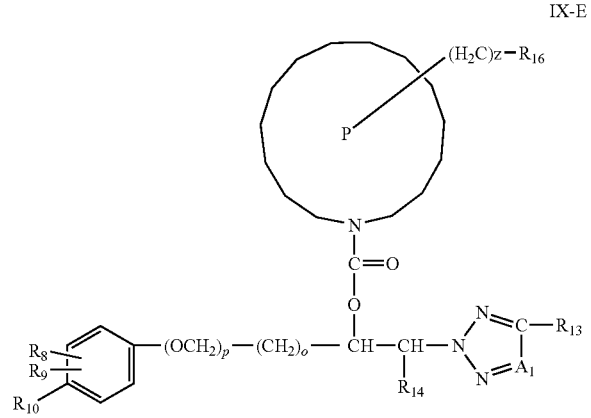

IX-E wherein

is a 4 to 6 membered a heterocycloalkyl ring containing at most 1 additional hetero nitrogen atom; $A_1$ is as above; $R_8$ and $R_9$ are hydrogen, halogen, lower alkoxy, lower alkyl, hydroxy, trifluromethyl, amino, mono or dilower alkyl amino, nitro or $R_8$ and $R_9$ when substituted on adjacent carbon atoms and when $R_{10}$ is hydrogen can be taken together to form a cyclolower alkyl, phenyl or heterocyclolower alkyl ring; $R_{10}$ is lower alkoxy, phenyoxy, phenylalkoxy, hydrogen, halogen, hydroxy lower alkyl, nitro, trifluoromethyl, mono or lower dikalkyl amino or amino; $R_{14}$ is hydrogen, amino carbonyl, or lower alkyl; $R_{13}$ is hydrogen, lower alkyl, amino, mono or dilower alkylamino hetero aromatic, amino carbonyl or phenyl where the phenyl group can be unsubstituted or mono or disubstituted with a lower alkyl, hydroxy, lower alkoxy, or halo; and 0, z and p are integers from 0-1; $R_{16}$ is phenyl, phenyl carbonyl, a five or six membered hetero aromatic ring containing from 1 to 4 nitro heteroatoms, wherein said phenyl and heteroaromatic rings can be unsubstituted or mono or di-substituted with hydroxy, hydroxy lower alkyl, lower alkoxy, halogen, phenyl or trifloromethyl.

58. The compound of claim 57 wherein o is 0 and p equals 1.
59. The compound of claim 57 wherein p is 0 and o is 0.
60. An azole compound of the formula:

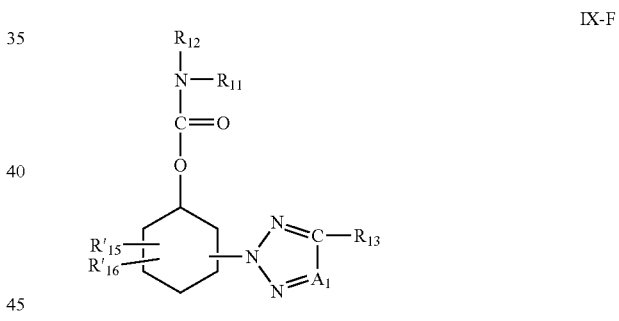

IX-F wherein $A_1$ is selected from the group consisting of a nitrogen atom and CH; $R_{11}$ is hydrogen, lower alkyl, amino carbonyl, phenyl or phenyl lower alkyl wherein the phenyl group can be unsubstituted or mono or disubstituted with a lower alkyl, hydroxy, lower alkoxy, halo, cyclo lower alkyl; $R_{12}$ is hydrogen or lower alkyl; or $R_{12}$ taken together with $R_{11}$ and their attached nitrogen atom form a 4 to 6 membered heteroarmatic ring containing at most 3 additional hetero nitrogen atoms; $R_{13}$ is hydrogen, amino, mono or dilower lower alkylamino hetero aromatic, amino carbonyl or phenyl where the phenyl group can be unsubstituted or mono or disubstituted with a lower alkyl, hydroxy, lower alkoxy, or halo; and $R'_{15}$ and $R'_{16}$ when taken together with their attached carbon atoms form a cycloalkyl or phenyl ring which can be unsubstituted or substituted with halo, lower alkyl, lower alkoxy, hydroxy, halogen or trifluoromethyl.

* * * * *